United States Patent
Gellman et al.

(10) Patent No.: US 6,683,154 B1
(45) Date of Patent: *Jan. 27, 2004

(54) ANTIMICROBIAL COMPOSITIONS CONTAINING β-AMINO ACID OLIGOMERS

(75) Inventors: Samuel Helmer Gellman, Madison, WI (US); Bernard Weisblum, Madison, WI (US); Emilie Ann Porter, Madison, WI (US); Xifang Wang, Acton, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,829

(22) Filed: Feb. 11, 2000

Related U.S. Application Data

(63) Continuation-in-part of application No. 09/034,509, filed on Mar. 4, 1998, now Pat. No. 6,060,585.
(60) Provisional application No. 60/039,905, filed on Mar. 4, 1997.

(51) Int. Cl.$^7$ .......................... C07K 7/00; C07K 17/00; A61K 38/00
(52) U.S. Cl. .......................... 530/323; 514/17; 514/18; 514/19; 514/20; 530/324; 530/329; 530/330; 530/331; 530/332; 530/333; 530/350
(58) Field of Search ...................... 514/17–20; 530/350, 530/328, 324, 323, 331, 332, 333

(56) References Cited

U.S. PATENT DOCUMENTS

| | | | | |
|---|---|---|---|---|
| 5,424,186 A | * | 6/1995 | Fodor et al. ................. | 435/6 |
| 5,631,291 A | * | 5/1997 | Mittendorf et al. .......... | 514/561 |
| 5,739,160 A | | 4/1998 | Mittendorf et al. | |
| 6,060,585 A | * | 5/2000 | Gellman et al. ............. | 530/323 |

FOREIGN PATENT DOCUMENTS

| | | |
|---|---|---|
| WO | WO 97/47593 | 12/1997 |
| WO | WO 00/76974 | 12/2000 |

OTHER PUBLICATIONS

Appella et al. J. Am. Chem. Soc. Dec. 1996, vol. 118, No. 51, pp. 13071–13072.*

Kricheldorf, H.R., et al., "13C–NMR sequence analysis XVIII tacticity of poly(D.L-beta-amino acids)" *Journal of Macromolecular Science: Part A—Chemistry*, Marcel Dekker, New York, NY, US, vol. A14, No. 7, 1980, pp. 977–990.

McReynolds, K.D., et al., "Examining the secondary structures of unnatural peptides and carbohydrate-based compounds utilizing circular dichroism" *Tetradheron: Asymmetry*, Elsevier Science Publishers, Amsterdam, NL, vol. 11, No. 3, Feb. 2000, pp.337–362.

Porter, E., et al., "Non-haemolytic beta-amino acid oligomers" *Nature*, vol. 404, 2000, p. 565.

Zanuy, D., et al., "On the structure of the phase A of comb-like poly(alpha-alkyl-beta, 1-aspartate)s: a molecular modelling study" *Polymer*, Elsevier Science Publishers, B.V., GB, vol. 42, No. 1, 2001, pp. 281–287.

Breithaupt, Holger,*Nature Biotechnology* (1999), 17: 1165–1169.

Bothner-By, A. A.; Stephens, R. L.; Lee, J.; Warren, C. D.; Jeanloz R. W. (1984) *J. Am. Chem. Soc.* (1984) 106:811.

Braunschweiler, L.; Ernst, R. R. (1983) *J. Magn. Reson.* 553:521.

Dado and Gellman (1994) *J. Am. Chem. Soc.* 116:1054–1062.

Hamuro et al. (1999) *J. Am. Chem. Soc.* 121:12200–12201.

Herradon and Seebach (1998) *Helv. Chim. Acta* 72:690–714.

Jefford and McNulty (1994), *J. Helv. Chim. Acta* 77:2142.

Kobayashi et al. (1990) *Chem. Pharm. Bull.* (1990) 38:350.

Macura, S.; Ernst, R. R. (1980) *Mol. Phys.* 41:95.

Nicus et al., Characterization of cancomucin resistance *Enterococcus faecium* and *Enterococcus faecalis, Antimicrob. Agents Chemother.* 33: 11121–24 (1989).

Nohira et al. (1970) *Bull. Chem. Soc. Jpn.* 43:2230.

Podlech and Seebach (1995), *Liebigs Ann.* 1217.

Seebach et al. (1996) *Helv. Chim. Acta.* 79:913–941.

Seebach et al. (1996) *Helv. Chim. Acta.* 79:2043–2066.

Suhara et al. (1996) *Tetrahedron Lett.* 37(10):1575–1578.

Tilley et al. (1992) *J. Med. Chem.* 35:3774–3783.

Weisblum et al., Erythromycin-inducible resistance in *Staphylococcus aurens*: survey of antibiotic cases involved, *J. Bacteriol.*, 98:447–52 (1969).

Yanisch-Perron et al., Improved M13 phage cloning vectors and host strains: nucleotide sequences of the M13mp18 and pUC19 vectors, *Gene* 33:103–19 (1985).

Young et al., Chromosomal location of genes regulating resistance to bacteriophage in *Bacillus subtilis, J. Bacteriol.*, 98:2087–97 (1969.

* cited by examiner

*Primary Examiner*—Maurie Garcia Baker
(74) *Attorney, Agent, or Firm*—Joseph T. Leone, Esq.; DeWitt Ross & Stevens S.C.

(57) ABSTRACT

Disclosed are antimicrobial compositions containing β-peptides and methods of inhibiting microbial growth in mammals using the compositions. The β-peptides present in the compositions contain ring structures in the peptide backbone which limit the conformational flexibility of the peptide backbone.

22 Claims, 20 Drawing Sheets n = 0, 1 or 2 n = 0, 1 or 2

SEQUENCE LISTING

<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: synthetic
     magainin derivative

<400> SEQUENCE: 1

Gly Ile Gly Lys Phe Leu His Ala Ala Lys Lys Phe Ala Lys Ala Phe
 1               5                  10                  15

Val Ala Glu Ile Met Asn Ser
             20

ANTIMICROBIAL COMPOSITIONS CONTAINING β-AMINO ACID OLIGOMERS

This is a Continuation-In-Part of application Ser. No. 09/034,509, now U.S. Pat. No. 6,060,585, filed Mar. 4, 1998, which claims priority U.S. provisional patent application Serial No. 60/039,905, filed Mar. 4, 1997, the contents of which are incorporated herein by reference.

This invention was made with United States government support awarded by the following agency: National Institutes of Health: 5 R01 GM56414-03. The United States government has certain rights in this invention.

FIELD OF THE INVENTION

The present invention is directed to antimicrobial compositions containing active ingredients which are oligomers and/or polymers of β-amino acids.

DESCRIPTION OF THE PRIOR ART

Chemists have long sought to extrapolate the power of biological catalysis and recognition to synthetic systems. These efforts have focused largely on low molecular weight catalysts and receptors. Most biological systems, however, rely almost exclusively on large polymers such as proteins and RNA to perform complex chemical functions.

Proteins and RNA are unique in their ability to adopt compact, well-ordered conformations. These two biopolymers are unique also because they can perform complex chemical operations (e.g., catalysis, highly selective recognition, etc.). Folding is linked to function in both proteins and RNA because the creation of an "active site" requires proper positioning of reactive groups. Consequently, there has been a long-felt need to identify synthetic polymer backbones which display discrete and predictable folding propensities (hereinafter referred to as "foldamers") to mimic natural biological systems. Such backbones will provide molecular "tools" to probe the functionality of large-molecule interactions (e.g. protein-protein and protein-RNA interactions).

Much work on β-amino acids and peptides synthesized therefrom has been performed by a group led by Dieter Seebach in Zurich, Switzerland. See, for example, Seebach et al. (1996) *Helv. Chim. Acta.* 79:913–941; and Seebach et al. (1996) *Helv. Chim. Acta.* 79:2043–2066. In the first of these two papers Seebach et al. describe the synthesis and characterization of a β-hexapeptide, namely (H-β-HVal-β-HAla-β-HLeu)$_2$-OH. Interestingly, this paper specifically notes that prior art reports on the structure of β-peptides have been contradictory and "partially controversial." In the second paper, Seebach et al. explore the secondary structure of the above-noted β-hexapeptide and the effects of residue variation on the secondary structure.

Dado and Gellman (1994) *J. Am. Chem. Soc.* 116:1054–1062 describe intramolecular hydrogen bonding in derivatives of β-alanine and γ-amino butyric acid. This paper postulates that β-peptides will fold in manners similar to α-amino acid polymers if intramolecular hydrogen bonding between nearest neighbor amide groups on the polymer backbone is not favored.

Suhara et al. (1996) *Tetrahedron Lett.* 37(10):1575–1578 report a polysaccharide analog of a β-peptide in which D-glycocylamine derivatives are linked to each other via a C-1 β-carboxylate and a C-2 α-amino group. This class of compounds has been given the trivial name "carbopeptoids."

Hamuro et al. (1999) *J. Am. Chem. Soc.* 121:12200–12201, describe antibacterial compositions containing β-peptides having a repeating 3-peptide residue motif. The compounds described are: Fmoc-(β$^3$-HVal-β$^3$-HLys-β$^3$-HLeu)$_n$-OH (n=2–4); H-(β$^3$-HVal-β$^3$-HLys-β$^3$-HLeu)$_n$-OH (n=2–4); and H-(β$^3$-HLeu-β$^3$-HLys-β$^3$-HLeu)$_n$-OH (n=2–6). While these β-peptides are described as being antibacterial, they are also hemolytic at concentrations near the effective antibacterial concentrations, thus limiting their utility as medicaments.

SUMMARY OF THE INVENTION

The increasing prevalence of pathogenic bacteria that are resistant to common chemotherapies has prompted an intensive search for new antibiotics. Cationic peptides that adopt amphiphilic secondary structures (e.g., magainins) constitute a widespread host defense against microbial invasions, and mimicry of these natural antibiotics led the present inventors on a search for new synthetic antimicrobial agents. Many of the cationic antimicrobial peptides appear to act by disrupting bacterial membranes, a mechanism that may not be conducive to the development of resistance. The subject invention is directed to antimicrobial compositions containing unnatural cationic oligomers that have no known natural counterpart and that display antibiotic activity comparable to that of a magainin derivative against at least four different bacterial species, including two pathogens that are resistant to common antibiotics. The oligomers are constructed from β-amino acid building blocks rather than the α-amino acid building blocks of conventional peptides. These β-peptides exhibit lower hemolytic activity than does the magainin derivative, which indicates a favorable selectivity for bacterial cells relative to mammalian cells. Because β-peptides are not expected to be subject to protease degradation, these results point toward the rational design of a promising new antibiotic class.

Specifically, the present invention is directed to compounds and to antimicrobial compositions containing the compounds, that is, compositions which inhibit the growth of microbes in general and bacteria and fungi in particular, the compositions comprising an antimicrobial-effective amount of a β-amino acid oligomer or polymer of the formula:

wherein "•••-A-B-C-•••" represents a β-amino acid oligomer or polymer chain, each of A, B, C, etc. representing individual residues of the oligomer or polymer chain and the ellipses representing adjacent N-terminal and C-terminal β-amino acid residues of the same genus, wherein each residue of the oligomer or polymer chain (that is, each A, B, C, etc.) is the same or different and is independently selected from the group consisting of:

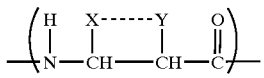

wherein X is selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —(CH$_2$)$_{n+1}$—OR, —(CH$_2$)$_{n+1}$—SR, —(CH$_2$)$_{n+1}$—S(=O)—CH$_2$—R, —(CH$_2$)$_{n+1}$—S(=O)$_2$—CH$_2$—R, —(CH$_2$)$_{n+1}$—NRR, —(CH$_2$)$_{n+1}$—NHC(=O)R, —(CH$_2$)$_{n+1}$—NHS(=O)$_2$—CH$_2$—R, —(CH$_2$)$_{n+1}$—

O—(CH)$_m$—R$^1$, —(CH$_2$)$_{n+1}$—S—(CH$_2$)$_m$—R$^1$, —(CH$_2$)$_{n+1}$—S(=O)—(CH$_2$)$_m$—R$^1$, —(CH$_2$)$_{n+1}$—S(=O)$_2$—(CH$_2$)$_m$—R$^1$, —(CH$_2$)$_{n+1}$—NH—(CH$_2$)$_m$—R$^1$, —(CH$_2$)$_{n+1}$—N—{(CH$_2$)$_m$—R$^1$}$_2$, —(CH$_2$)$_{n+1}$—NHC(=O)—(CH$_2$)$_{n+1}$—R$^1$, and —(CH$_2$)$_{n+1}$—NHS(=O)$_2$—(CH$_2$)$_m$—R$^1$;

wherein R is independently selected from the group consisting of hydrogen, C$_1$–C$_6$-alkyl, alkenyl, or alkynyl; mono- or bicyclic aryl, mono- or bicyclic heteraryl having up to 5 heteroatoms selected from N, O, and S; mono- or bicyclic aryl-C$_1$–C$_6$-alkyl, mono- or bicyclic heteroaryl-C$_1$–C$_6$-alkyl; and wherein R$^1$ is selected from the group consisting of hydroxy, C$_1$–C$_6$-alkyloxy, aryloxy, heteroaryloxy, thio, C$_1$–C$_6$-alkylthio, C$_1$–C$_6$-alkylsulfinyl, C$_1$–C$_6$-alkylsulfonyl, arylthio, arylsulfinyl, arylsulfonyl, heteroarylthio, heteroarylsulfinyl, heteroarylsulfonyl, amino, mono- or di-C$_1$–C$_6$-alkylamino, mono- or diarylamino, mono- or diheteroarylamino, N-alkyl-N-arylamino, N-alkyl-N-heteroarylamino, N-aryl-N-heteroarylamino, aryl-C$_1$–C$_6$-alkylamino, carboxylic acid, carboxamide, mono- or di-C$_1$–C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-C$_1$–C$_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of C$_1$–C$_6$-alkyl, aryl, heteroaryl; O-alkylurethane, O-arylurethane, and O-heteroarylurethane;

wherein Y is selected from the group consisting of hydrogen, linear or branched C$_1$–C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$–C$_6$-alkyl, mono- or bicyclic heteroaryl-C$_1$–C$_6$-alkyl, —(CH$_2$)$_n$—OR, —(CH$_2$)$_n$—SR, —(CH$_2$)$_n$—S(=O)—CH$_2$—R, —(CH$_2$)$_n$—S(=O)$_2$—CH$_2$—R, —(CH$_2$)$_n$—NRR, —(CH$_2$)$_n$—NHC(=O)R, —(CH$_2$)$_n$—NHS(=O)$_2$—CH$_2$—R, —(CH$_2$)$_n$—O—(CH)$_m$—R$^1$, —(CH$_2$)$_n$—S—(CH$_2$)$_m$—R$^1$, —(CH$_2$)$_n$—S(=O)—(CH$_2$)$_m$—R$^1$, —(CH$_2$)$_n$—S(=O)$_2$—(CH$_2$)$_m$—R$^1$, —(CH$_2$)$_n$—NH—(CH$_2$)$_m$—R$^1$, —(CH$_2$)$_n$—N—{(CH$_2$)$_m$—R$^1$}$_2$—(CH$_2$)$_n$—NHC(=O)—(CH$_2$)$_m$—R$^1$, and —(CH$_2$)$_n$—NHS(=O)$_2$—(CH$_2$)$_m$—R$^1$;

wherein R and R$^1$ are as defined above; or

X and Y combined, together with the carbon atoms to which they are bonded, independently define a substituted or unsubstituted C$_3$–C$_8$ cycloalkyl, cycloalkenyl or heterocyclic ring having one or more N, O or S atom(s) as the heteroatom(s);

the substituents on carbon atoms of these rings being independently selected from the group consisting of linear or branched C$_1$–C$_6$-alkyl, alkenyl, alkynyl; mono- or bicyclic aryl, mono- or bicyclic heteraryl having up to 5 heteroatoms selected from N, O, and S; mono- or bicyclic aryl-C$_1$–C$_6$-alkyl, mono- or bicyclic heteroaryl-C$_1$–C$_6$-alkyl, and the substituents listed above for X and Y when X and Y are not combined;

the substituents on nitrogen heteroatoms being independently selected from the group consisting of —S(=O)$_2$—CH$_2$—R, —C(=O)—R, —S(=O)$_2$—(CH$_2$)$_m$—R$^1$, —C(=O)—(CH$_2$)$_{n+1}$—R$^1$; wherein R and R$^1$ are as defined above;

m is an integer of from 2–6 and n is an integer of from 0–6;

W is hydrogen or an amino-terminal capping group (such as formyl, acetyl, tBoc, Fmoc, etc.); Z is hydroxy or a carboxy-terminal capping group (such as NH$_2$, NH(alkyl), N(alkyl)$_2$, etc.); and wherein the total number of residues is greater than 6; and further wherein in at least one residue, X and Y are combined in a cyclic moiety; pharmaceutically-suitable salts thereof, and combinations thereof; optionally in combination with a pharmaceutically-suitable carrier.

When X is not combined with Y, X and Y are preferably (and independently) selected from the group consisting of linear or branched C$_1$–C$_6$-alkyl, hydroxy-C$_1$–C$_6$-alkyl, amino-C$_1$–C$_6$-alkyl, aryl-C$_1$–C$_6$-alkyl, heteroaryl-C$_1$–C$_6$-alkyl, and carboxyl-C$_1$–C$_6$-alkyl. When X and Y are combined together into a cyclic substituent, together X and Y and the carbons to which they are bonded define a substituted or unsubstituted cyclopentyl, substituted or unsubstituted cyclohexyl, unsubstituted or N-substituted piperidinyl, or unsubstituted or N-substituted pyrrolidinyl.

In a another embodiment, the composition contains a β-amino acid oligomer or polymer of the above, wherein each residue (A, B, C, etc.) of the oligomer is a β-amino acid residue of formula:

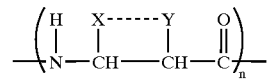

wherein X and Y combined, together with the carbon atoms to which they are bonded, independently from residue to residue define a substituted or unsubsituted C$_3$–C$_8$ cycloalkyl, cycloalkenyl or heterocyclic ring having one or more nitrogen atoms as the sole heteroatom, the substituents being selected from the group consisting of hydroxy, linear or branched C$_1$–C$_6$-alkyl, alkenyl, alkynyl; hydroxy-C$_1$–C$_6$-alkyl, amino-C$_1$–C$_6$-alkyl, C$_1$–C$_6$-alkyloxy, C$_1$–C$_6$-alkyloxy-C$_1$–C$_6$-alkyl, amino, mono- or di-C$_1$–C$_6$-alkylamino, carboxamido, carboxamido-C$_1$–C$_6$-alkyl, sulfonamido, sulfonamido-C$_1$–C$_6$-alkyl, urea, cyano, fluoro, thio, C$_1$–C$_6$-alkylthio, mono- or bicyclic aryl, mono- or bicyclic heteraryl having up to 5 heteroatoms selected from N, O, and S; mono- or bicyclic aryl-C$_1$–C$_6$-alkyl, heteroaryl-C$_1$–C$_6$-alkyl, and combinations thereof; where n is a positive integer greater than 6; and pharmaceutically-acceptable salts thereof, optionally in combination with a pharmaceutically-suitable carrier.

The invention is likewise directed to a method of inhibiting microbial growth in mammals, including humans, the method comprising administering an antimicrobial amount of a composition as recited above to a patient in need thereof.

Other aims, objects, and advantages of the invention will appear more fully from a complete reading of the following Detailed Description of the Invention and the attached claims.

DETAILED DESCRIPTION OF THE INVENTION

Overview

Figure 1:
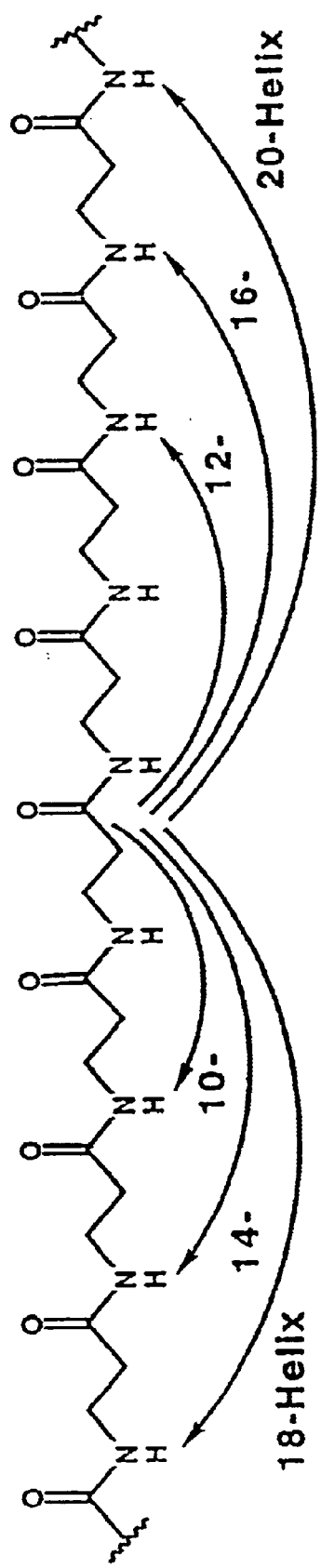
FIG. 1 shows the structure of poly-β-alanine and further depicts the hydrogen bonds that define the six narrowest helices available to poly-β-alanine. Poly-β-alanine is the simplest β-peptide polymer.

Helices in β-Peptides:

Initial molecular modeling studies indicated that β-amino acid oligomers ("β-peptides") are well suited for adoption of compact secondary structures stabilized by intramolecular hydrogen bonds. FIG. 1 shows the hydrogen bonds that define the six narrowest helices available to poly-β-alanine, the simplest β-peptide polymer. The 12-, 16-, and 20-helices (nomenclature derived from hydrogen-bonded ring size) contain hydrogen bonds from carbonyls toward NH groups in the N-terminal direction, as observed for $3_{10}$- and α-helices in proteins, while the 10-, 14-, and 18-helices contain hydrogen bonds from carbonyls to NH groups in the N-terminal direction. Molecular mechanics studies of a β-alanine decamer suggested that all six of these helices constitute local minima on the conformational energy surface. β-Alanine oligomers, however, have been shown experimentally to be unordered in solution and to adopt sheetlike packing patterns in the solid state.

Incorporation of the two backbone carbons of a β-amino acid into a small carbocycle or heterocycle provides substantial rigidity to the backbone. Computational methods were used to evaluate whether any particular helix/small ring combination would lead to enhanced conformational stability. For each of the six minimized deca-β-alanine helices shown in FIG. 1, each residue was modified by incorporation of the backbone carbons into a three-, four-, five-, and six-membered cycloalkyl ring. For each ring size, both cis and trans relationships between the amino and carboxyl substituents were examined, and for the cis rings, both of the possible ring orientations relative to the helix were examined. This process yields 72 helical starting structures (6 helices×4 cycloalkyl ring sizes×(1 trans+2 cis forms)). A combination of minimization and dynamics studies predicted that the 14-helical form of the decamer of trans-2-aminocyclohexanecarboxylic acid (trans-ACHC) (the corresponding monomer is referred to herein as trans-ACHA) and the 12-helical form of the decamer of trans-2-aminocyclopentanecarboxylic acid (trans-ACPC) (corresponding monomer referred to as trans-ACPA) would be the most stable among these hypothetical helices. These two structures are shown below:

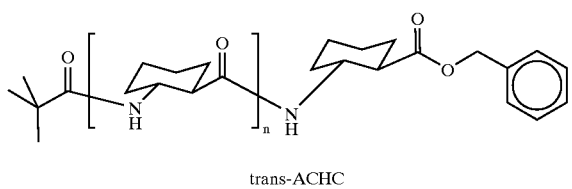

trans-ACHC

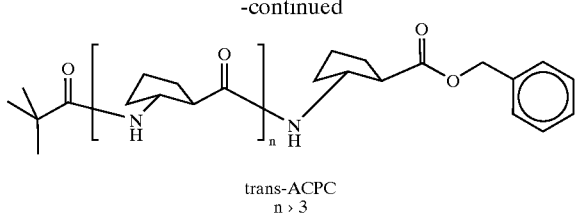

trans-ACPC
n > 3

In order to test this computational prediction, optically active trans-ACHC was prepared by the reported route, Nohira et al. (1970) *Bull. Chem. Soc. Jpn.* 43:2230, and polypeptide oligomers synthesized via standard methods (see below). The crystal structures of the trans-ACHC tetramer and the trans-ACHC hexamer reveal that these molecules adopt 14-helical conformations in the solid state. The hexamer crystal contains three independent but very similar molecules, each of which forms the four possible 14-membered ring hydrogen bonds. The regular helix revealed by the hexamer crystal structure matches the minimum energy conformation predicted for the decamer.

Figure 2A:
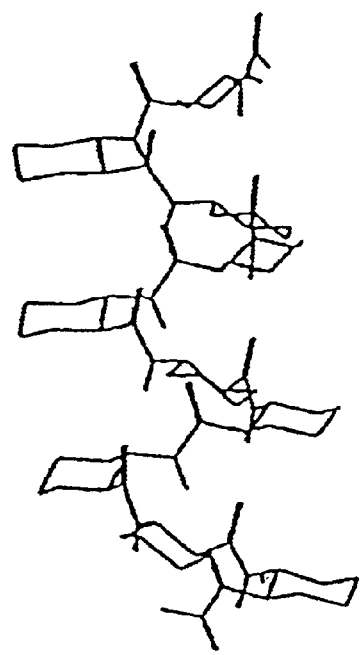
FIG. 2A depicts the crystal structure of oligomer of trans-ACHC/14-helix. The bottom depiction is the two-dimensional structure, the middle depiction is a view along the axis of the helix, and the top depiction is a view perpendicular to the axis of the helix.
Figure 2A:
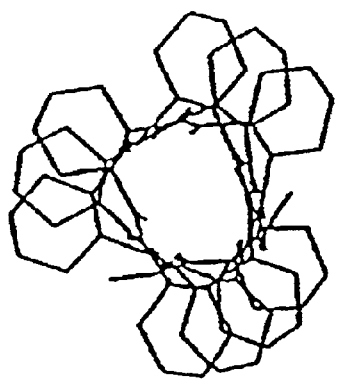
Figure 2A:
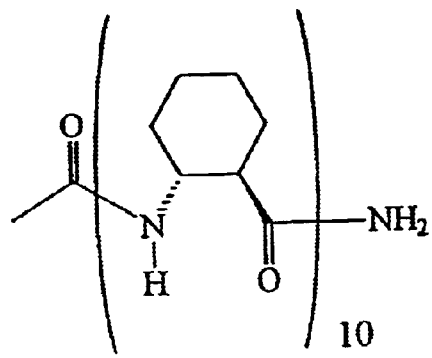
Figure 2B:
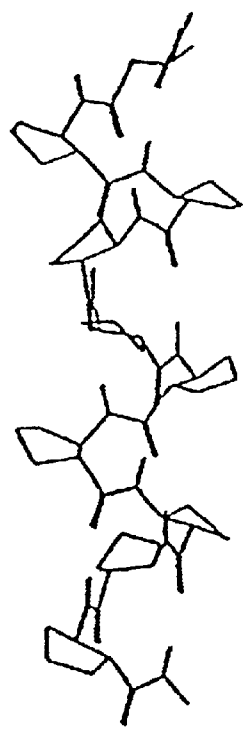
FIG. 2B depicts the crystal structure of oligomer of trans-ACPC/12-helix. The views shown are the same as in FIG. 2A.
Figure 2B:
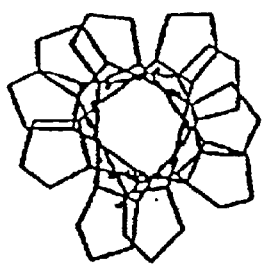
Figure 2B:
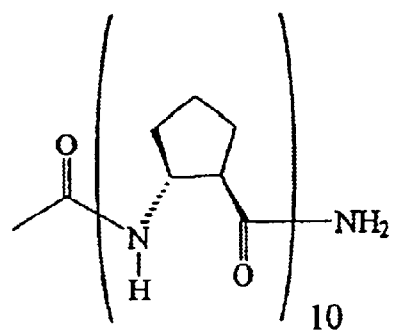
Figure 2C:
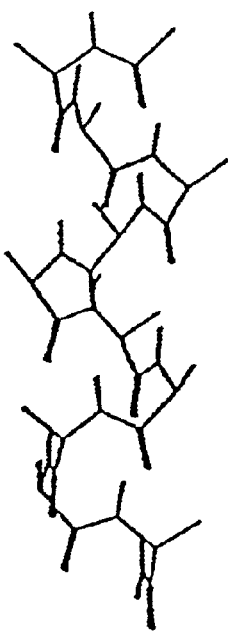
FIG. 2C depicts the crystal structure of a standard α-helix. The views shown are the same as in FIG. 2A.
Figure 2C:
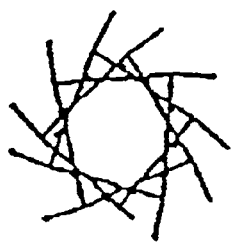
Figure 2C:
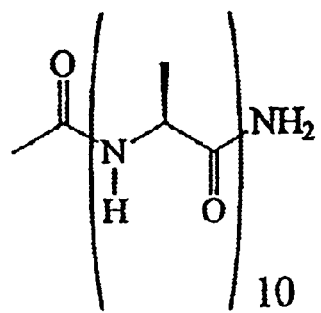

An alternatively rigidified β-amino acid, trans-2-aminocyclopentanecarboxylic acid (trans-ACPC), provides β-peptides with a dramatically altered secondary structure, the 12-helix. FIG. 2B depicts the 12-helix trans-ACPC structure, as compared to a standard α-helix (FIG. 2C) and trans-ACHC/14-helix (FIG. 2A). This finding shows that β-peptides allow profound residue-based control of peptide conformation.

Chemistry:

General. Melting points are uncorrected. $CH_2Cl_2$ was freshly distilled from $CaH_2$ under $N_2$. DMF was distilled under reduced pressure from ninhydrin and stored over 4 Å molecular sieves. Triethylamine was distilled from $CaH_2$ before use. Other solvents and reagents were used as obtained from commercial suppliers. For BOC removal, 4 M HCl in dioxane from was used. Column chromatography was carried out by using low air pressure (typically 6 psi) with 230–400 mesh silica gel 60. Routine $^1$H-NMR spectra were obtained on a Bruker AC-300 and are referenced to residual protonated NMR solvent. Routine $^{13}$C-NMR spectra were obtained on a Bruker AC-300 and are referenced to the NMR solvent. High resolution electron impact mass spectroscopy was performed on a Kratos MS-80RFA spectrometer with DS55/DS90.

Infrared Spectroscopy. Spectra were obtained on a Nicolet Model 740 FT-IR spectrometer. IR samples were prepared under anhydrous conditions; $CH_2Cl_2$ was freshly distilled from $CaH_2$, compounds and glassware were dried under vacuum for 1–2 days, and solutions were prepared under a nitrogen atmosphere. The pure solvent spectrum for a particular solution was subtracted from the sample spectrum prior to analysis. Peaks in the amide NH stretch region were baseline corrected, and analyzed without further manipulation.

NMR Spectroscopy. 1. Aggregation Studies. One-dimensional spectra for aggregation studies were obtained on a Bruker AC-300 spectrometer. Samples for aggregation studies were prepared by serial dilution from the most concentrated sample (50 mM or 27 mM). Dry compounds were dissolved in $CD_2Cl_2$ previously dried over 3 Å molecular sieves, and samples were prepared with dry glassware under a nitrogen atmosphere.

2. Conformational Analysis. NMR samples for conformational analysis were prepared by dissolving the dry compound in dry deuterated solvent under a nitrogen atmosphere. $CD_2Cl_2$ samples were then degassed by the freeze-pump-thaw method, and the NMR tubes were sealed under vacuum. Methanol samples were sealed with a close fitting cap and parafilm. COSY spectra were obtained on a Bruker AC-300 spectrometer. TOCSY (Braunschweiler, L.; Ernst, R. R. (1983) *J. Magn. Reson.* 53:521), NOESY (Macura, S.; Ernst, R. R. (1980) *Mol. Phys.* 41:95), and ROESY (Bothner-By, A. A.; Stephens, R. L.; Lee, J.; Warren, C. D.; Jeanloz R. W. (1984) *J. Am. Chem. Soc.* (1984) 106:811) spectra were squired on a Varian Unity-500 spectrometer using standard Varian pulse sequences and hypercomplex phase cycling (States-Haberkorn method), and the data were processed with Varian "VNMR" version 5.1 software. Proton signals were assigned via COSY and TOCSY spectra, and NOESY and ROESY spectra provided the data used in the conformational analyses. TOCSY spectra were recorded with 2048 points in $t_1$, 320 or 350 points in $t_2$, and 8 or 40 scans per $t_2$ increment. NOESY and ROESY spectra were recorded with a similar number of $t_1$ and $t_2$ points, and 32 and 40 scans per $t_2$ increment, depending on the sample concentration. The width of the spectral window examined was between 2000 and 4000 Hz. Sample concentrations for two-dimensional spectra were 2 mM in $CD_2Cl_2$ and 8 mM in $CD_3OD$ and $CD_3OH$.

Far UV Circular Dichroism (CD). Data were obtained on a Jasco J-715 instrument at 20° C. In all CD plots contained herein, the mean residue ellipticity is presented on the vertical axis. Presenting the mean residue ellipticity is a standard practice in peptide chemistry wherein the intensity of each CD spectrum is normalized for the number of amide chromophores in the peptide backbone. Consequently, when the intensities of the maximum (ca. 205 nm) and minimum (ca. 220 nm) peaks characteristic of helix formation increase with increasing chain length, this change represents an increase in the population of the helix structure, rather than simply an increase in the number of chromophores present in each molecule.

Synthesis. The β-amino acids used to assemble the peptides described herein can be manufactured using several different literature methods, as well as new methods described below. For unsubstituted β-amino acids and β-amino acids containing one or two acyclic substituents on the carbon adjacent to the amino group in the product β-peptide, the Arndt-Eisterdt homologation reaction can be used, see Reaction 1. See also Seebach et al. (1996) *Helv. Chim. Acta* 79:913. This route has advantages and disadvantages. A distinct advantage is that the starting materials, α-amino acids, are readily available commercially in enantiomerically pure form. The Arndt-Eisterdt homologation also results in the simultaneous coupling of two β-amino residues. A distinct disadvantage is that the reaction cannot be used to synthesize β-amino acids having rings in the backbone or α-carbon substituents. The reaction proceeds via a Wolff rearrangement of a diazoketone with subsequent trapping of the reactive intermediate with an amino moiety, as shown in Reaction 1:

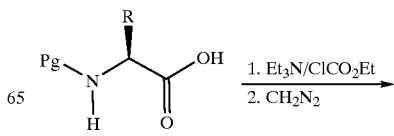

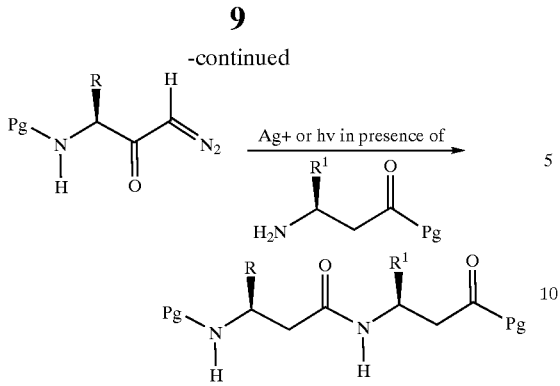

(Pg designates a protecting group such as (t-butoxy)carbonyl (Boc) or an adjacent β-amino residue, $R^1$ and $R^2$ are aliphatic substituents.

β-Amino acids containing an unsubstituted cycloalkyl moiety involving the α and β carbons were synthesized using literature methods. See, for example, Nohira et al. (1970) *Bull. Chem. Soc. Jpn.* 43:2230; Herradon and Seebach (1989) *Helv. Chim. Acta* 72:690–714; and Tilley et al. (1992) *J. Med. Chem.* 35:3774–3783, all three of which are incorporated herein by reference.

In particular, the cyclohexyl-containing β-amino acids can be synthesized via Reaction 2:

REACTION 2

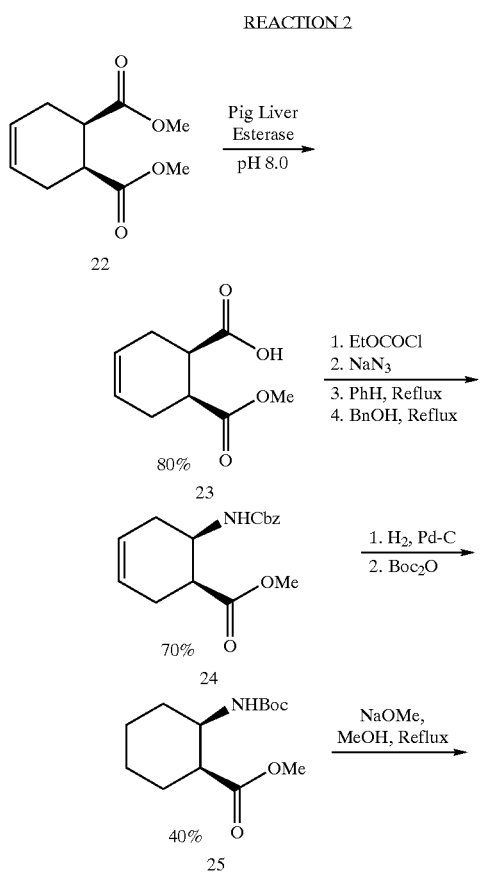

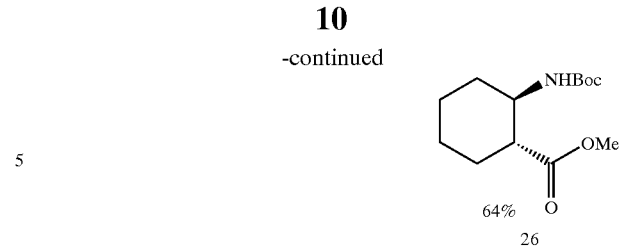

(1R,6S)-6-Methoxycarbonyl-3-cyclohexene-1-carboxylic acid (23): 4600 u of PLE was suspended in pH 8.01 aqueous buffer solution (0.17 M $KH_2PO_4$). The diester 22 (10.1 g, 0.05 mol) was dissolved in 30 mL of acetone and added to the buffer solution. Reaction was allowed to stir at rt overnight. The enzyme was filtered off through a well-packed celite pad, the solution was then acidified to pH 1 with 1M HCl and the product was extracted with ethyl acetate (5×400 mL). The combined organic extracts were dried over anhydrous magnesium sulfate and concentrated to yield 9.00 g yellow oil. Product taken on without further purification.

Methyl (1S,6R)-6-benzyloxycarbonylaminocyclohex-3-ene carboxylate (24): Ethylchloroforamate (4 mL, 0.042 mol) was added to a mixture of 23 (5.14 g, 0.028 mol) and triethylamine (6 mL, 0.043 mol) in acetone (100 mL) at 0° C. and vigorously stirred for 10 min. An aqueous solution of $NaN_3$ (3.04 g, 0.047 mol, in 25 mL water) was added in one portion. The resulting mixture was stirred for 30 min at 0° C. The reaction mixture was diluted with water and extracted with diethyl ether. The organic extracts were dried over anhydrous magnesium sulfate and concentrated without heat to yield a viscous yellow liquid. The liquid was dissolved in 100 mL of benzene and refluxed under nitrogen atmosphere for 30 min. Benzyl alcohol (12 mL, 0.116 mol) was added and solution was refluxed for an additional 16 h. The reaction was cooled to rt and concentrated to yield 17.12 g of a yellow liquid (mixture of benzyl alcohol and desired product in a 5.4:1 ratio, respectively by $^1$H NMR, ~5.67 g product). Mixture taken on without further purification.

Methyl (1S,6R)-6-tert-butoxycarbonylaminocyclohexane carboxylate (25): The yellow oil from the previous reaction, which contains compound 24 (5.6 g, 0.020 mol) and benzyl alcohol, was dissolved in methanol. 0.525 g of 10% Pd on carbon was added to the methanol solution, and the heterogenous mixture was placed under 50 psi $H_2$ and shaken at rt for 24 h. The mixture was filtered through celite, and the filtrate was concentrated to yield 13.74 g of dark golden yellow liquid. 25 mL of 1M HCl was added to the filtrate, and the benzyl alcohol was extracted with diethyl ether (3×25 mL). The pH of the aqueous solution was adjusted to 9 using $K_2CO_3$. 25 mL of dioxane and $Boc_2O$ (5 g, 0.023 mol) were added to the solution, and the reaction was stirred at rt for 20 h. 15 mL of water was added and the solution was extracted with ethyl acetate (3×50 mL). The combined organic extracts were dried over anhydrous magnesium sulfate and concentrated. Residue was purified via column chromatography ($SiO_2$, eluting with 6:1 Hex:EtOAc), to yield 2.00 g viscous clear oil.

Methyl (1R,6R)-6-tert-butoxycarbonylaminocyclohexane carboxylate (26): Sodium metal (0.14 g, 6.1 mmol) was placed into a flame dried flask under nitrogen atmosphere and cooled to 0° C. 10 mL of freshly distilled methanol was added and the mixture stirred until all the sodium dissolved. An amount of 25 (2.00 g, 7.7 mmol) was dissolved in 10 mL of freshly distilled methanol and transferred to NaOMe solution via cannula. The solution was refluxed under nitrogen for 5.5 h, cooled to rt and acidified with 0.5 M aqueous 0.5 M ammonium chloride (18 mL, 9 mmol). The methanol was removed under reduced pressure, and the resulting solid collected by filtration to yield 1.27 g of desired product.

β-Amino acids containing a substituted cycloalkyl moiety were synthesized using the following illustrative protocol, the first four steps of which are described in Kobayashi et al. (1990) *Chem. Pharm. Bull.* (1990) 38:350. The remaining steps to yield a cyclohexyl ring having two differentially protected amino substituents were developed in furtherance of the present invention and have not heretofore been described in the literature and are shown in Reaction 3:

REACTION 3

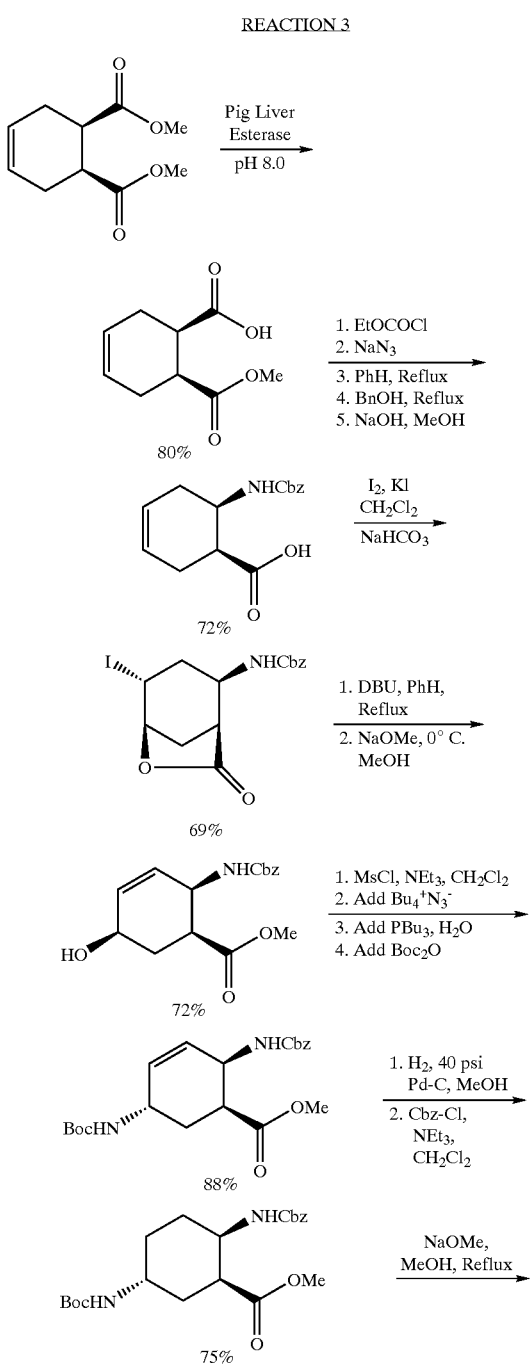

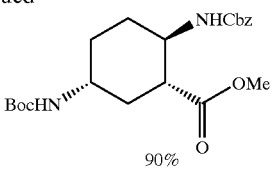

As depicted in Reaction 3, the 4-position amino substituent is protected by a Boc group and the 1-position amino substituent is protected by a Cbz group. The starting material is available commercially (Aldrich Chemical Co., Milwaukee, Wis.).

Synthesis of β-amino acids containing a heterocylic ring moiety encompassing the α and β carbons were synthesized using Reactions 4 and 5, below. Reaction 4 details an illustrative synthesis of a β-proline wherein the exocyclic amino substituent is in the 3-position relative to the ring nitrogen.

Compound 42: Tap water (200 ml) and baker's yeast (25 g) were mixed, and were shaken on an orbital shaker for 1 hour. Compound 41 (1.0 g) was then added. The mixture was shaken at room temperature for 24 hours. The mixture was filtered through a bed of Celite. The Celite was washed with water (20 ml). The filtrate was extracted with diethyl ether (5×100 ml). The extracts were washed with water (2×50 ml), dried over $MgSO_4$, and concentrated to yield a slightly yellow oil. The crude product was purified by column chromatography with ethyl acetate/hexane (1/1, v/v) as eluent to give a colorless oil (0.5 g) in 50% yield.

Compound 43: Compound 42 (228 mg) and $Ph_3P$ (346 mg) were dissolved in benzene (anhydrous, 4 ml) under nitrogen. $HN_3$ (1.64 M in benzene, 0.8 ml) was then added. A solution of diethyl azodicarboxylate (0.18 ml) in benzene (1.0 ml) was subsequently introduced via syringe over 5 minutes. The reaction mixture turned cloudy towards the end of the addition. The reaction mixture was stirred under nitrogen at room temperature for 3.0 hours. The reaction mixture was then taken up in ethyl acetate (50 ml), washed with 1N NaOH (10 ml), saturated $NaHCO_3$ (10 ml), and finally dilute brine (5 ml). The organic was dried over $MgSO_4$, and concentrated to give a slightly yellow oil. The crude oil was purified by column chromatography with ethyl acetate/hexane (1/1, v/v) as eluent to afford a colorless oil (190 mg) in 76% yield.

Compound 44: Compound 43 (1.1 g) was dissolved in methanol (50 ml). $SnCl_2$ (2.2 g) was then added. The mixture was stirred at room temperature for 30 hours. The methanol was then removed under reduced pressure. The residue was dissolved in

REACTION 4

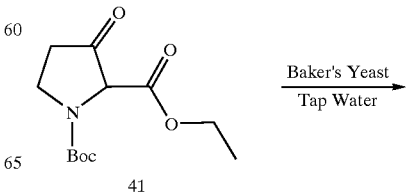

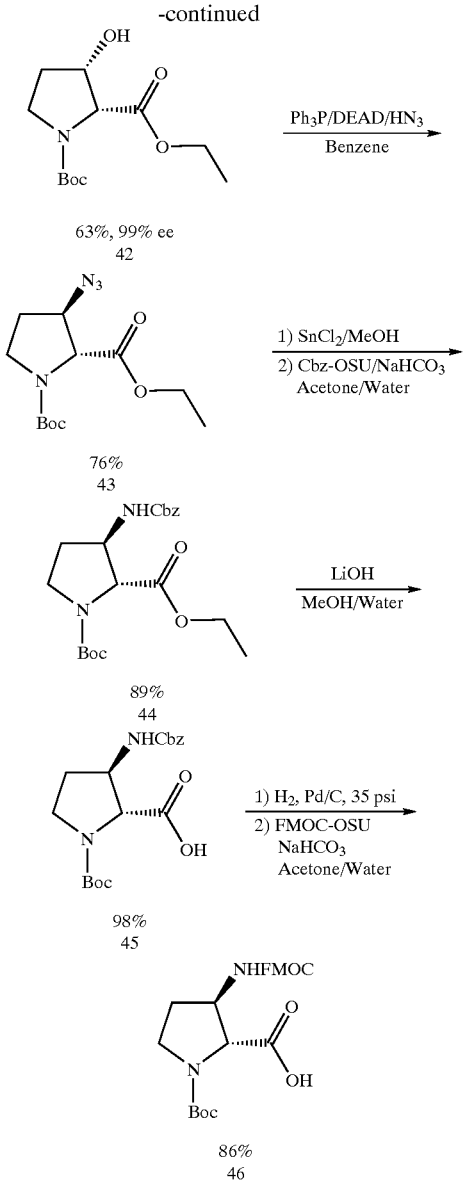

DEAD = Diethyl azodicarboxylate
Cbz-OSU = N-(Benzyloxycarbonyloxy)succinimide
Fmoc-OSU = 9-Fluorenylmethyloxycarbonyl-N-hydroxysuccinimide
Starting material: Blake, J. et al. J. Am. Chem. Soc. 1964,86, 5293.
Yeast reduction: Cooper, J. et al. J. Am. Chem. Soc. Perkin Trans. 1 1993, 1313.

methylene chloride (50 ml). The resulting cloudy solution was filtered through Celite. The methylene chloride was then removed under reduced pressure. The residual white solid was dissolved in acetone/water (2/1, v/v, 50 ml). NaHCO$_3$ (3.3 g) was added, followed by Cbz-OSU (1.16 g). The reaction mixture was stirred at room temperature for 24 hours. Water (50 ml) was added. The acetone was removed under reduced pressure. The aqueous mixture was extracted with ethyl acetate (3×100 ml). The extracts were washed with dilute brine (30 ml), dried over MgSO$_4$, and concentrated to give a colorless oil. The crude product was purified by column chromatography with ethyl acetate/hexane (3/7, v/v) as eluent to give the clean product as a colorless oil (1.35 g) in 89% yield.

Compound 45: Compound 44 (1.35 g) was dissolved in methanol/water (3/1, v/v, 80 ml), cooled to 0° C. LiOH.H2O (1.68 g) was added. The mixture was stirred at 0° C. for 24 hours, by which time TLC indicated that the hydrolysis was complete. Saturated ammonium hydroxide (20 ml) was added. The methanol was removed under reduced pressure. The aqueous was washed with diethyl ether (50 ml), acidified with 1N HCl to pH 3, extracted with methylene chloride (3×150 ml). The extracts were washed with dilute brine (50 ml), dried over MgSO$_4$, concentrated to give a sticky colorless residue (1.25 g, 99%), which was used directly without further purification.

Compound 46: Compound 45 (1.25 g) was dissolved in methanol (50 ml) in a hydrogenation flask. 5% Palladium on activated carbon (190 mg) was added. The flask was pressurized with hydrogen to 35 psi, rocked at room temperature for 7 hours, by which time TLC indicated that the hydrogenolysis was complete. The Pd/C was removed by filtration. The filtrate was concentrated to give a white solid. The white solid was dissolved in acetone/water (2/1, v/v, 70 ml), cooled to 0° C. NaHCO$_3$ (1.7 g) was added, followed by FMOC-OSU (1.39 g). The reaction mixture was stirred at room temperature for 16 hours. Water (50 ml) was added. The acetone was removed under reduced pressure. The aqueous was washed with diethyl ether (50 ml), acidified with 1N HCl to pH 3, extracted with methylene chloride (3×150 ml). The extracts were washed with dilute brine (50 ml), dried over MgSO$_4$, concentrated to give a foamy white solid. The crude white solid was purified by column chromatography with methanol/ethyl acetate (3/7, v/v) as eluent to give the clean product as a white solid (1.3 g) in 86% yield.

Reaction 5 illustrates the synthesis of a β-amino acid wherein the exocyclic amino substituent the nitrogen heteroatom is in the 4-position relative to the ring nitrogen.

Compound 52: Compound 51 (2.0 g) and NaBH$_3$CN (0.54 g) were dissolved in methanol (40 ml), 1N HCl (aqueous) was added dropwise to maintain pH 3–4. After 15–20 minutes, pH change slowed. The mixture was stirred for an additional 1.0 hour, while 1N HCl was added occasionally to keep pH 3–4. Water (100 ml) was added. The mixture was extracted diethyl ether (3×150 ml). The extracts were washed with IN NaHCO$_3$ (100 ml) and dilute brine (100 ml), dried over MgSO$_4$, and concentrated to give a colorless oil (1.9 g) in 95% yield. The product was used directly without further purification.

Compound 53: Compound 52 (1.9 g) and Ph$_3$P (2.8 g) were dissolved in toluene (anhydrous, 30 ml) under nitrogen. A solution of diethyl azodicarboxylate (1.5 ml) in toluene (10 ml) was subsequently introduced via syringe over 15 minutes. The reaction mixture was stirred under nitrogen at room temperature for 12 hours. The toluene was removed under reduced pressure. The residue was purified by column chromatography with ethyl acetate/hexane (3/7, v/v) as eluent to afford a colorless oil (1.6 g) in 91% yield.

Compound 54: Compound 53 (1.0 g) and R-(+)-α-methylbenzylamine (1.1 ml) were mixed with water (15 ml). The mixture was stirred at 55° C. for 67 hours. The mixture was taken up in diethyl ether (300 ml), and the aqueous layer was separated. The ether solution was washed with water (3×50 ml), dried over MgSO$_4$, and concentrated to give a slight yellow oil. The diastereometic isomers were separated by column chromatography with ethyl acetate/hexane (2/8, v/v) as eluent to give RSS (0.2 g) and RRR (0.34 g) in 51% overall yield.

Compound 55: Compound 54 (4.2 g) was dissolved in ethyl acetate (200 ml). 4N HCl in dioxane (4.35 ml) was added dropwise while stirring. A white precipitate

REACTION 5

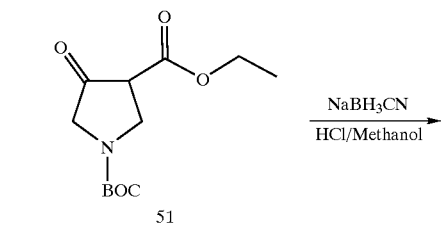
51

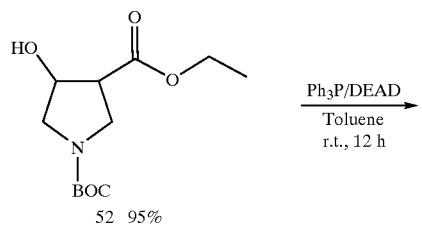
52 95%

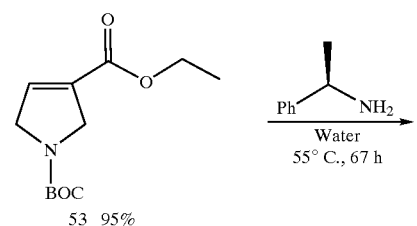
53 95%

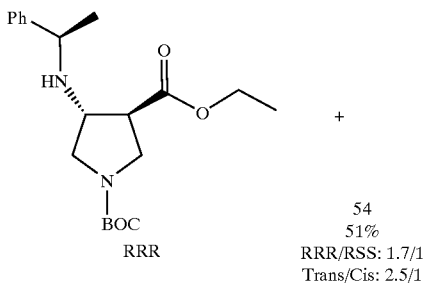
54 51%
RRR
RRR/RSS: 1.7/1
Trans/Cis: 2.5/1

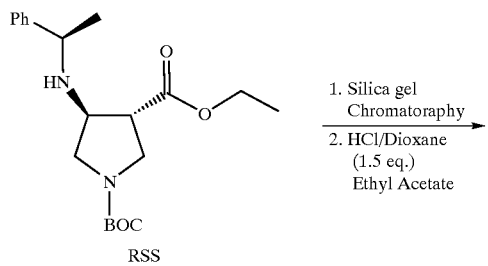
RSS

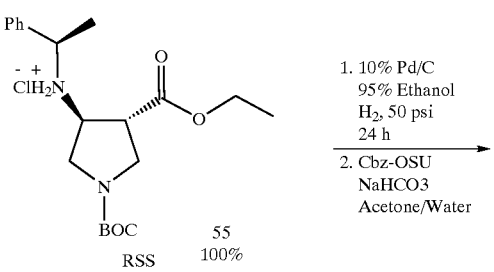
55 100%
RSS

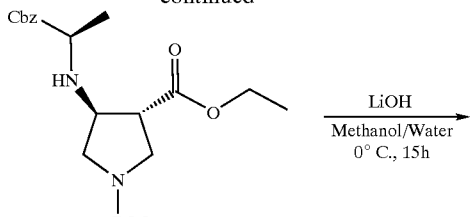
56 90%

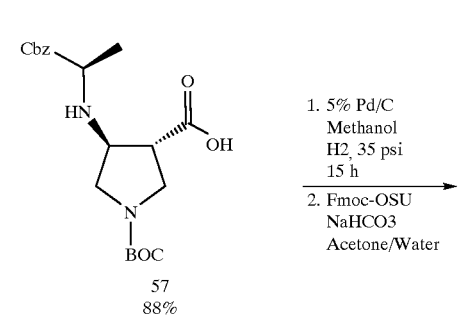
57 88%

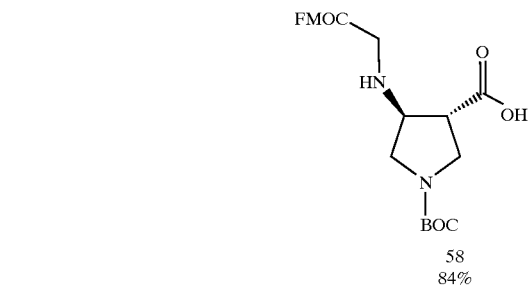
58 84%

DEAD = Diethyl azodicarboxylate
Cbz-OSU = N-(Benzyloxycarbonyloxy) succinimide
Fmoc-OSU = 9-Fluorenylmethyloxycarbonyl-N-hydroxysuccinimide
Starting material: Blake, J. et al J. Am. Chem. Soc. 1964, 86, 5293.

resulted. The ethyl acetate was removed under reduced pressure, and the resulting white solid (4.6 g, 100%) was dried in vacuo.

Compound 56: Compound 55 (4.6 g) was dissolved in 95% ethanol (150 ml) in a hydrogenation flask. 10% Palladium on activated carbon (0.5 g) was added. The flask was pressurized with hydrogen to 50 psi, rocked at room temperature for 22 hours, by which time NMR spectroscopy indicated that the hydrogenolysis was complete. The Pd/C was removed by filtration. The filtrate was concentrated to give a white solid. The white solid was dissolved in acetone/water (2/1, v/v, 150 ml). NaHCO$_3$ (9.7 g) was added, followed by Cbz-OSU (3.4 g). The reaction mixture was stirred at room temperature for 14 hours. Water (100 ml) was added. The acetone was removed under reduced pressure. The aqueous mixture was extracted with ethyl acetate (3×200 ml). The extracts were washed with 1N HCl (3×100 ml) and saturated NaHCO$_3$ (aqueous), dried over MgSO$_4$, and concentrated to give a colorless oil. The crude product was purified by column chromatography with ethyl acetate/hexane (3/7, v/v) as eluent lo give the clean product as a colorless sticky oil (4.0 g) in 90% yield.

Compound 57: Compound 56 (2.0 g) was dissolved in methanol/water (3/1, v/v, 115 ml), cooled to 0° C., LiOH.H2O (2.4 g) was added. The mixture was stirred at 0° C. for 15 hours, by which time TLC indicated that the hydrolysis was complete. Saturated ammonium hydroxide (aqueous, 100 ml) was added. The methanol was removed under reduced pressure. The aqueous was acidified with 1N HCl to pH 3, extracted with ethyl acetate (3×200 ml). The extracts were washed with dilute brine (100 ml), dried over MgSO$_4$, concentrated to give a foamy solid (1.63 g, 88%), which was used directly without further purification).

Compound 58: Compound 57 (1.63 g) was dissolved in methanol (70 ml) in a hydrogenation flask. 5% Palladium on activated carbon (250 mg) was added. The flask was pressurized with hydrogen to 35 psi, rocked at room temperature for 15 hours, by which time NMR spectroscopy indicated that the hydrogenolysis was complete. The Pd/C was removed by filtration. The filtrate was concentrated to ive a white solid. The white solid was dissolved in acetone/water (2/1, v/v, 90 ml), cooled to 0° C. NaHCO$_3$ (2.27 g) was added, followed by FMOC-OSU (1.83 g). The reaction mixture was stirred at 0° C. for 2 hours, then at room temperature for 28 hours. Water (50 ml) was added. The acetone was removed under reduced pressure. The aqueous was acidified with 1N HCl to pH 3, extracted with ethyl acetate (3×200 ml). The extracts were washed with dilute brine (100 ml), dried over MgSO$_4$, concentrated to give a foamy white solid. The crude white solid was purified by column chromatography with methanolfethyl acetate (3/7, v/v) as eluent to give the clean product as a white solid (1.68 g) in 84% yield.

To synthesize the nipecotic reverse turn moiety, Reaction 6 was used.

REACTION 6

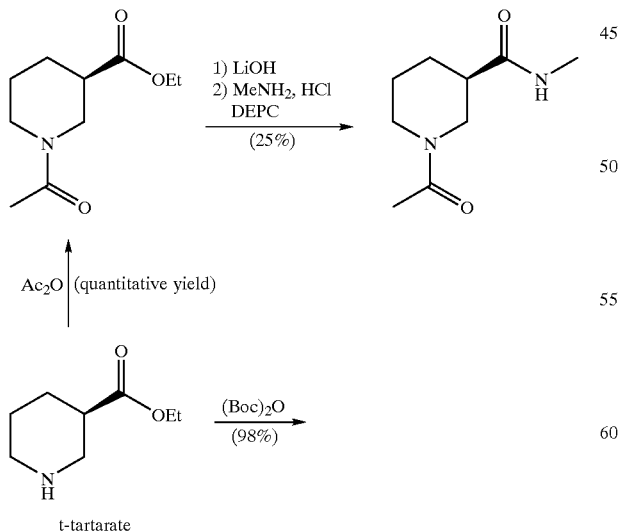

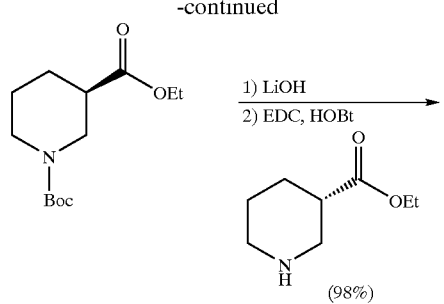

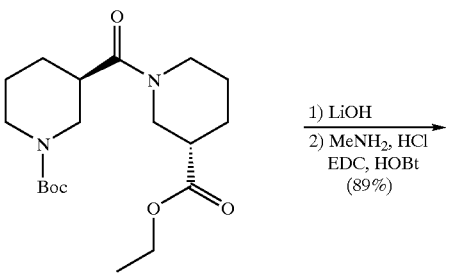

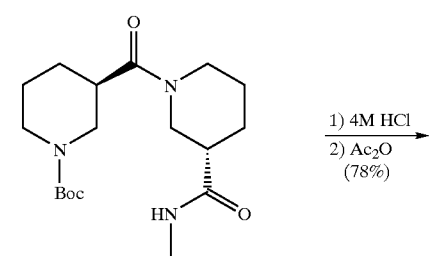

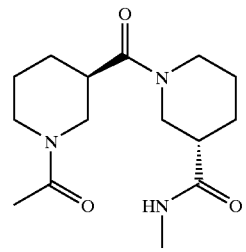

To synthesize β-peptides having reverse turn moiety which is a prolyl-glycolic acid residue, the following protocols are preferred:

(2S,3R)-3-Amino-2-methylpentanoic acid was prepared according to the procedures given by Jefford and McNulty (1994), *J. Helv. Chim. Acta* 77:2142. However, unlike the description in this paper, the synthesized (2S,3S)-2-methyl-3-(tosylamino)butano-4-lactone contained up to 8% (2R,3S)-2-methyl-3-(tosylamino)butano-4-lactone as a byproduct, which could be removed by recrystallization from toluene. (2S,3S)-3-Amino-2-benzyl-4-phenylthiobutanoic acid was prepared in a synthetic sequence derived from the one by Jefford and McNulty. This synthesis is described below. Homo-α-amino acids were prepared according to the procedures by Podlech and Seebach (1995), *Liebigs Ann.* 1217. Depsi-β-peptides were synthesized by conventional dicyclohexylcarbodiimide/N-hydroxysuccinimide (DCC/HOSu) or 1-ethyl-3-

(3'dimethylaminopropyl)carbodiimidde hydrochloride/N,N-dimethyl-4-aminopyridine (EDCI/DMAP) solution-phase coupling procedures (see, for example, Bodanszky, M.; Bodanszky, A. *The Practice of Peptide Synthesis*; Springer Verlag: New York, 1984). Illustrative procedures are given below.

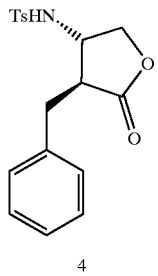

4

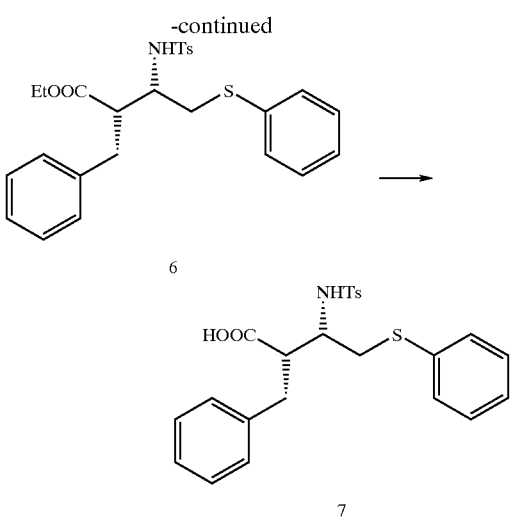

(2S,3S)-2-Benzyl-3-(tosylamino)butano-4-lactone (4). A solution of lithium diisopropylamine (LDA) in THF was generated by adding 1.5 M methyllithium in diethyl ether (30 mL, 45.0 mmol) to a solution of diisopropylamine (6.4 mL, 45.7 mmol) in 100 mL THF at 0° C. under nitrogen and stirring for 10 min. The solution was then cooled to −78° C., and a solution of (3S)-3-(tosylamino)butano-4-lactone (5.36 g, 21.1 mmol) in 30 mL THF was added dropwise. The resulting yellow solution was stirred for 1 hour at −78° C., and then benzyl bromide (10 mL, 84.1 mmol) was added rapidly. Stirring at −78° C. was continued for 2 hours, and the reaction was quenched with 20 mL sat. aq. $NH_4Cl$ solution and allowed to warm to room temperature. The mixture was acidified with 1 M HCl and extracted three times with methylene chloride. The combined organic extracts were dried over $Na_2SO_4$ and evaporated to give an orange semisolid that was purified by chromatography (silica gel, hexane/ethyl acetate 3:2) to yield 2.22 g (8.70 mmol, 41%) recovered starting material and 3.37 g (9.76 mmol; 46%) of 4. No diastereomeric addition product could be detected. For further purification 4 can be recrystallized from toluene to give colorless needles. mp. 108.5–109° C., $^1$H-NMR (300 MHz, $CDCl_3$) δ 7.58 (d, J=8.5 Hz, 2H), 7.31 (d, J=8.2 Hz, 2H), 7.20 (m, 3H), 6.92 (dd, J=7.7, 1.7 Hz, 2H), 4.97 (d, J=5.5 Hz, 1H), 4.27 (dd, J=7.2, 9.8 Hz, 1H), 3.98 (dd, J=7.2, 9.8 Hz, 1H); 3.65 (m, 1H), 3.00 (m, 1H), 2.77 (m, 2H), 2.46 (s, 3H), $^{13}$C-NMR (75.5 MHz, $CDCl_3$) δ 144.27 (C), 138.00 (C), 135.83 (C), 129.89 (CH), 128.97 (CH), 128.88 (CH), 127.10 (CH) 71.25 ($CH_2$) 53.21 (CH), 46.54 (CH), 33.54 ($CH_2$) 21.50 ($CH_3$), EI MS m/e 345.1027 calc. for $C_{18}H_{19}NO_4S$ 345.1035.

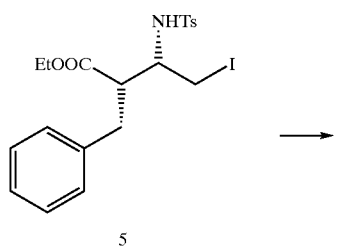

5

(2S,3S)-2-Benzyl-4-phenylthio-3-(tosylamino)butanoic acid (7). (2S,3S)-2-Benzyl-3-(tosylamino)butano-4-lactone (4) (0.91 g, 2.64 mmol) was dissolved in 10 mL methylene chloride. At 0° C. trimethylsilyliodide (1 mL, 7.03 mmol) and anhydrous ethanol (0.72 mL, 12.2 mmol) were added under nitrogen. The solution was stirred 30 min. at 0° C., allowed to warm to room temperature and stirred for 1 day. Then the addition of trimethylsilyliodide and ethanol was repeated and stirring at room temperature was continued for 12 hours. The reaction was quenched by the addition of 3 mL ethanol and stirring for 30 min. To the solution 20 mL of water were added, the layers were separated, and the aqueous layer was extracted five times with methylene chloride. The combined organic extracts were washed with 5% aq. $Na_2S_2O_3$ solution, dried over $Na_2SO_4$ and concentrated in vacuo to give 1.78 g of crude 5 as an orange solid, which was used in the next step without further purification.

At 0° C., thiophenol (0.73 ml, 7.11 mmol) was added to a suspension of NaH (289.7 mg, 7.24 mmol) in 6 mL DMF under nitrogen, warmed to room temperature and stirred for 15 min. A solution of crude 5 (1.78 g) in 10 mL DMF was added to the thiophenolate solution at 0° C. After warming to room temperature the solution was stirred for 1 hour. The reaction was quenched with 50 ml water and extracted three times with methylene chloride. The combined organic extracts were washed with brine, dried over $Na_2SO_4$ and concentrated in vacuo to give 2.43 g of 6 as a colorless oil, which was used in the next step without further purification.

To a solution of 6 (2.43 g) in 18 mL methanol a 1.5 M aq. NaOH solution was added and the mixture heated to 60° C. for 2 hours. After evaporation of methanol in vacuo, 20 mL water was added and the mixture extracted two times with diethyl ether. The aqueous layer was acidified with conc. HCl and extracted four times with diethyl ether. The organic extracts were dried over $Na_2SO_4$ and evaporated to yield 1.04 g (2.28 mmol, 86%) of 7.$^1$H-NMR (300 MHz, $CDCl_3$) δ 7.45 (d, J=8.3 Hz, 2H), 7.24–7.17 (m, 6H), 7.09–7.00 (m, 6H), 5.54 (d, J=8.3 Hz, NH), 3.46 (m, 1H), 3.28 (m, 1H), 3.00 (m, 3H), 2.67 (dd, J=7.1, 14.0 Hz, 1H), 2.34 (s, 3H).

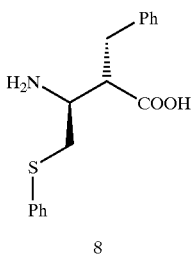

8

(2S,3S)-3-Amino-2-Benzyl-4-phenylthiobutanoic acid (8). Compound 7 and phenol (0.77 g) were dissolved in 50 mL 48% HBr and heated to reflux for 1.5 hours under nitrogen. After cooling to room temperature 150 mL water was added and the solution extracted two times with diethyl ether. The yellow aqueous layer was evaporated to give 0.58 g of (2S,3S)-3-amino-2-benzyl-4-phenylthiobutanoic acid hydrobromide as an orange solid. $^1$H-NMR (300 MHz, CDCl$_3$) δ 7.69 (b, 3NH), 7.43 (m, 2H), 7.34–7.01 (m 8H), 3.60 (m, 1H), 3.35 (m, 3H), 3.08 (dd, J=8.2, 14.2 Hz, 1H), 2.87 (dd, J=7.5, 14.2 Hz, 1H).

The hydrobromide was dissolved in 140 mL anhydrous ethanol, and 28 mL methyloxirane was added. The solution was heated to reflux for 1 hour under nitrogen. The solvent was evaporated to yield 0.45 g (1.45 mmol, 65%) of 8.

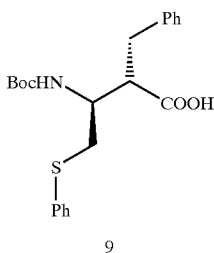

9

(2S,3S)-3-(t-Butoxycarbonylamino)-2-benzyl-4-phenylthiobutanoic acid. To a solution of 8 (0.18 g, 0.597 mmol) in 1 mL water and 2 mL dioxane was added K$_2$CO$_3$ (167.9 mg, 1.21 mmol). After cooling to 0° C., di-t-butyl-dicarbonate (153.2 mg, 0.681 mmol) was added, the solution warmed to room temperature and stirred for 1 day. The solution was concentrated in vacuo, and the residue dissolved in 20 mL water. The solution was acidified to pH 2–3 (congo red) with 1 M HCl and extracted five times with ethyl acetate. The combined organic extracts were dried over MgSO$_4$ and evaporated to give an orange oil that was purified by chromatography (silica gel, hexane/ethyl acetate 1:2) to yield 63.4 mg (0.159 mmol, 27%) of 9. $^1$H-NMR (300 MHz, CDCl$_3$) δ 7.37–7.13 (m, 10H), 5.47 (d, J=8.5 Hz, NH), 3.88 (m, 1H), 3.20 (m, 1H), 3.00 (m, 1H), 2.84 (m, 3H), 1.39 (s, 9H), $^{13}$C-NMR (75.5 MHz, CDCl$_3$) δ 174.82 (C), 156.49 (C), 140.14 (C), 136.80 (C), 130.44 (C), 130.02 (C), 129.81 (C), 129.36 (C), 127.33 (C), 127.27 (C), 79.68 (C), 52.46 (CH), 52.33 (CH), 37.37 (CH$_2$), 35.25 (CH$_2$), 28.55 (3 CH$_3$).

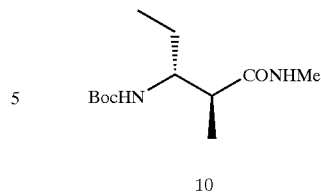

10

Methyl-(2S,3R)-3-(t-butoxycarbonylamino)-2methylpentanoic amide (10). (2S,3R)-3-(t-Butoxycarbonylamino)-2-methylpentanoic acid (149.1 mg, 0.645 mmol) was dissolved in 1 mL DMF. At 0° C. methylamine hydrochloride (88.6 mg, 1.31 mmol) and DMAP (195.7 mg, 1.60 mmol) were added, followed by EDCI (1-ethyl-3-(3'dimethylaminopropyl)carbodiimidde hydrochloride) (376.9 mg, 1.97 mmol). After stirring at room temperature for 2 days, the solvent was removed in a stream of nitrogen and the residue dried in vacuo. The residue was titurated with 1 mL 1 M HCl and 4 mL water, and the white precipitate was collected by suction filtration to yield 121.0 mg (0.495 mmol, 66%) of the amide 10 mp. 206–207° C., $^1$H-NMR (300 MHz, CDCl$_3$) δ 5.92 (b, NH), 4.72 (b, NH), 3.58 (m, 1H), 2.77 (d, J=4.8 Hz, 3H), 2.45 (m, 1H), 1.45 (m, 1H), 1.41 (s, 9H), 1.40 (m, 1H), 1.13 (d, J=7.2 Hz, 3H), 0.90 (t, J=7.4 Hz, 3H), $^{13}$C-NMR (75.5 MHz, CDCl$_3$) δ 174.83 (C), 156.15 (C), 79.35 (C), 54.62 (CH), 45.02 (CH), 28.35 (3 CH$_3$), 26.24 (CH$_3$), 25.18 (CH$_2$), 13.71 (CH$_3$), 10.85 (CH$_3$), EI MS m/e 244.1789 calc. for C$_{12}$H$_{24}$N$_2$O$_3$ 244.1787.

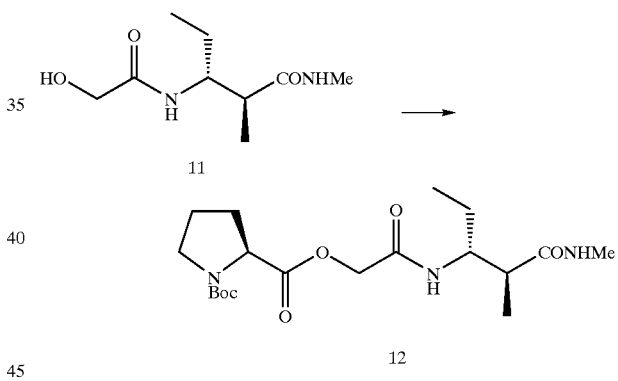

Compound 12. Compound 10 (121.0 mg, 0.495 mmol) was dissolved in 2 mL of 4 M HCl/dioxane, and the resulting solution was stirred 1 hour at room temperature. HCl/dioxane was then removed in a stream of nitrogen and the deprotected amide dried in vacuo. The activated glycolic ester was prepared by adding EDCI (188.7 mg, 0.635 mmol) to a solution of glycolic acid (45.5 mg, 0.598 mmol) and HOSu (N-hydroxysuccinimide) (72.7 mg, 0.632 mmol) in 1 mL DMF and stirring of the solution at room temperature for 2 hours. The deprotected amide and triethylamine (85 µl, 0.610 mmol) were dissolved in 1 mL DMF and transferred into the activated ester solution. After stirring the resulting solution for 2 days at room temperature, the solvent was removed in a stream of nitrogen and the residue dried in vacuo. The residue was separated by chromatography (silica gel, CHCl$_3$/MeOH 4:1) to yield impure 11 (192.7 mg), which was used in the next step without further purification.

Compound 11 (192.7 mg) and BOC-L-proline (213.3 mg, 0.991 mmol) were dissolved in 3 mL DMF. DMAP (15.6 mg, 0.128 mmol) was added, followed by DCC (dicyclohexylcarbodiimide) (248.3 mg, 1.20 mmol), and the resulting solution was stirred overnight at room temperature. The white precipitate was filtered off by suction filtration, and the filtrate was concentrated in vacuo. The residue was separated by chromatography (silica gel, CHCl₃/MeOH 19:1) to yield 145.7 mg (0.365 mmol, 74% based on 10) of 12. ¹H-NMR (300 MHz, CDCl₃) δ 7.02 (d, J=8.6 Hz, NH major rotamer 89%), 6.91 (d, J=9.0 Hz, NH minor rotamer 11%), 6.10 (m, NH), 4.78 (AB, A part, J=15.3 Hz, 1H), 4.49 (AB, B part, J=15.3 Hz, 1H) 4.26 (m, 1H), 3.90 (m, 1H), 3.44 (m, 2H), 2.74 (d, J=4.6 Hz, 3H), 2.45 (quint., J=7.0 Hz, 1H), 2.22 (m, 1H), 1.98 (m, 2H), 1.88 (m, 1H), 1.56 (m, 1H), 1.43 (s, 9H), 1.43 (m, 1H), 1.08 (d, J=7.0 Hz, 3H), 0.86 (t, J=7.4 Hz), ¹³C-NMR (75.5 MHz, CDCl₃) δ 174.80 (C), 172.24 (C), 167.47 (C), 154.78 (C), 80.33 (C), 62.79 (CH₂), 58.77 (CH), 53.74 (CH), 46.75 (CH₂), 45.58 (CH), 29.91 (CH₂), 28.26 (3 CH₃), 26.05 (CH₃), 24.97 (CH₂), 24.49 (CH₂), 14.43 (CH₃), 10.62 (CH₃).

13

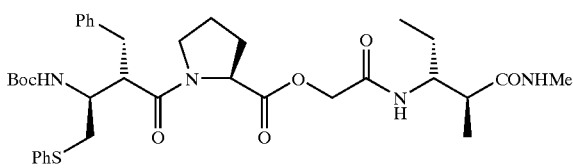

Compound 13. Compound 12 (12.3 mg, 30.8 μmol) was dissolved in 1 mmol 4 M HCl/dioxane and the solution was stirred for 1 hour at room temperature. HCl/dioxane was removed in a stream of nitrogen and the residue dried in vacuo. The deprotected depsipeptide and (2S ,3S)-2-benzyl-3-(t-butoxycarbonylamino)-4-phenylthiobutanoic acid (9) (14.3 mg, 35.6 μmol) were dissolved in 0.5 mL methylene chloride. DMAP (5.0 mg, 40.9 μmol) was added, followed by EDCI (13.7 mg, 71.5 μmol). After stirring at room temperature for 2 days, the solvent was removed in a stream of nitrogen and the residue dried in vacuo. The residue was titurated with 1 mL water, which was acidified to pH 2. The resulting solid was collected and purified by chromatography (silica gel, CHCl₃/MeOH 19:1) to yield 14.1 mg (20.6 μmol, 67%) of 13. ¹H-NMR (300 MHz, CDCl₃) δ 7.41 (d, J=10.1 Hz, NH), 7.38–7.13 (m, 10H+NH), 5.06 (AB, A part, J=15.3 Hz, 1H), 5.03 (d, J=10.5 Hz, NH), 4.45 (m, 1H), 4.32 (AB, B part, J=15.5 Hz, 1H), 4.26 (m, 1H), 4.02 (t, J=7.6 Hz, 1H), 3.31 (m, 1H), 3.08 (m, 3H), 2.97 (m, 1H), 2.83 (m, 1H), 2.78 (d, J=4.6Hz, 3H), 2.53 (m, 1H), 2.39 (dq, J=10.1 Hz, 6.9 Hz, 1H), 1.98 (m, 1H), 1.73 (m, 2H), 1.50 (m, 1H), 1.44 (m, 1H), 1.41 (s, 9H), 1.30 (m, 1H), 1.07 (d, J=6.9 Hz, 3H), 0.98 (t, J=7.4 Hz, 3H), ¹³C-NMR (75.5 MHz, CDCl₃) δ 175.44 (C), 171.63 (C), 167.03 (C), 155.54 (C), 138.29 (C), 135,46 (C), 129.43 (CH), 129.06 (CH), 128.68 (CH), 128.30 (CH), 126.60 (CH), 126.47 (CH), 80.24 (C), 62.69 (CH₂), 59.27 (CH), 52.71 (CH), 52.46 (CH), 49.39 (CH), 46.75 (CH₂), 46.66 (CH), 38.16 (CH₂), 36.32 (CH₂), 28.58 (CH₂), 28.11 (3 CH₃), 26.26 (CH₂), 25.85 (CH₃), 25.05 (CH₂), 16.22 (CH₃), 10.47 (CH₃).

1

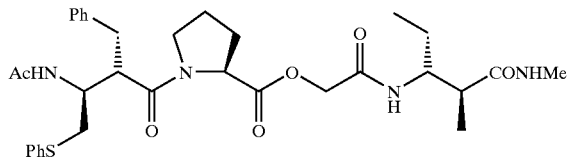

Compound 1. Compound 13 (14.1 mg, 20.6 μmol) was dissolved in 1 mL 4 M HCl/dioxane and the solution was stirred for 1 hour at room temperature. HCl/dioxane was removed in a stream of nitrogen and the residue dried in vacuo. The deprotected depsipeptide and triethylamine (5.8 μL, 41.6 μmol) were dissolved in 0.41 mL methylene chloride, and acetic anhydride (2.4 μL, 25.4 μmol) was added. After stirring the solution at room temperature overnight the solvent was removed in a stream of nitrogen and the residue dried in vacuo. The residue was purified by chromatography (silica gel, CHCl₃/MeOH 19:1) to yield 9.2 mg (14.7 μmol, 71%) of 1. mp. 196.5–197° C., ¹H-NMR (300 MHz, CDCl₃) δ 7.40 (d, J=9.0 Hz, NH), 7.39–7.11 (m, 10H+NH), 5.99 (d, J=10.1 Hz, NH), 5.03 (AB, A part, J=15.3 Hz, 1H), 4.78 (tt, J=10.3 Hz, 3.6 Hz, 1H), 4.34 (AB, B part, J=15.3 Hz, 1H), 4.25 (dq, J=10.0 Hz, 1H), 4.02 (t, J=7.4 Hz, 1H), 3.36 (m, 1H), 3.20–3.00 (m, 3H), 2.85–2.75 (m, 2H), 2.79 (d, J=4.6 Hz, 3H), 2.60 (m, 1H), 2.42 (dq, J=10.1 Hz, 6.9 Hz, 1H), 2.00 (m, 1H), 1.86 (s, 3H), 1.85–1.62 (m, 3H), 1.52 (m, 1H), 1.31 (m, 1H), 1.07 (d, J=6.8 Hz, 3H), 0.97 (t, J=7.4 Hz, 3H), ¹³C-NMR (75.5 MHz, CDCl₃) δ 175.46 (C), 171.59 (C), 170.17 (C), 167.08 (C), 138.14 (C), 136.87 (C), 135,36 (C), 129.49 (CH), 129.15 (CH), 128.60 (CH), 128.34 (CH), 126.88 (CH), 126.64 (CH), 62.69 (CH₂), 59.30 (CH), 52.80 (CH), 51.08 (CH), 48.69 (CH), 46.83 (CH₂), 46.28 (CH), 37.37 (CH₂), 36.30 (CH₂), 34.45 (CH₂), 28.59 (CH₂), 26.03 (CH₃), 25.07 (CH₂), 23.00 (CH₃), 16.09 (CH₃), 10.46 (CH₃), IR (1 mM in CH₂Cl₂) 3423, 3367, 1753, 1669, 1626 cm⁻¹, EI MS m/e 624.2989 calc. for C₃₃H₄₄N₄O₆S 624.2981.

14

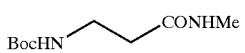

Methyl-3-(t-butoxycarbonylamino)propionic amide (14). BOC-β-alanine (0.50 g, 2.64 mmol) was dissolved in 4 mL DMF. Methylamine hydrochloride (198 mg, 2.93 mmol) and DMAP (427.2 mg, 3.50 mmol) were added, followed by EDCI (1.06 g, 5.53 mmol). After stirring at room temperature for 2 days the solvent was removed in a stream of nitrogen and the residue dried in vacuo. It was dissolved in 5 mL 1 M HCl, and the solution was extracted five times with ethyl acetate. The combined organic extracts were dried over MgSO₄ and concentrated to yield 0.43 g (2.13 mmol, 81%) of BOC-β-alanine methylamide (14) as a white solid. mp. 117–118° C., ¹H-NMR (300 MHz, CDCl₃) δ 5.78 (b, NH), 5.15 (b, NH), 3.38 (q, J=6.1 Hz, 2H), 2.78 (d, J=4.8 Hz, 3H), 2.36 (t, J=6.1 Hz, 2H), 1.40 (s, 9H) ¹³C-NMR (75.5 MHz, CDCl₃) δ 171.74(C), 79.15 (C), 36.41 (CH₂), 36.03 (CH₂), 28.17 (3 CH₃), 26.04 (CH₃).

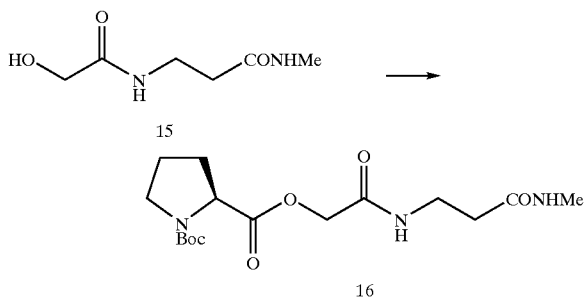

Compound 16. Compound 14 (0.33 g, 1.63 mmol) was dissolved in 5 mL of 4 M HCl/dioxane, and the solution was stirred at 12° C. for 1 hour. The HCl/dioxane was removed in a stream of nitrogen and the residue dried in vacuo. An activated ester solution was prepared by adding DCC (509.9 mg, 2.47 mmol) to a solution of glycolic acid (145.7 mg, 1.92 mmol) and HOSu (326.4 mg, 2.84 mmol) in 10 mL methylene chloride. A white precipitate formed after a few minutes. The suspension was stirred at 12° C. for 6 hours. The deprotected amide and triethylamine (0.27 mL, 1.94 mmol) were dissolved in 10 mL methylene chloride and transferred into the activated ester solution. After stirring the resulting solution overnight at room temperature, the white precipitate was filtered off by suction filtration and the filtrate concentrated to give a white solid, which was purified by chromatography (silica gel, CHCl$_3$/MEOH 19:1) to yield 0.30 g of impure 15, which was used in the next step without further purification.

Compound 15 (0.30 g) and BOC-L-proline (371.5 mg, 1.73 mmol) were dissolved in 50 mL methylene chloride. At 0° C. DMAP (25.6 mg, 0.210 mmol) was added, followed by DCC (402.9 mg, 1.95 mmol). After stirring 1 hour at 0° C. the suspension was allowed to warm to room temperature and stirred overnight. The white precipitate was filtered off by suction filtration and the filtrate concentrated. The residue was subjected to chromatography (silica gel, CHCl$_3$/MEOH 19:1) to yield 0.23 g (0.644 mmol, 40% based on 14) of 15 as a colorless glass. $^1$H-NMR (300 MHz, CDCl$_3$) δ 7.55 (b, NH major rotamer 84%), 7.05 (b, NH minor rotamer 16%), 6.25 (b, NH major rotamer 83%), 6.04 (b, NH, minor rotamer 17%), 4.59 (s, 2H), 4.25 (m, 1H), 3.59 (m, 1H), 3.42 (m, 3H), 2.73 (d, J=4.8 Hz, 3H), 2.41 (t, J=6.5 Hz, 2H), 2.22 (m, 1H), 1.96 (m, 2H), 1.88 (m, 1H), 1.42 (s, 9H).

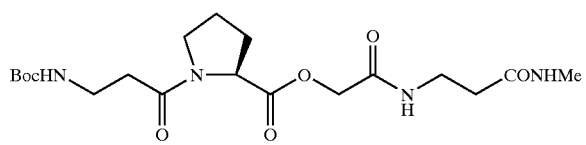

Compound 17. Compound 16 (0.23 g, 0.644 mmol) was dissolved in 2 mL 4 M HCl/dioxane, and the solution was stirred for 1 hour at room temperature. HCl/dioxane was removed in a stream of nitrogen and the residue dried in vacuo. The deprotected depsipeptide and BOC-β-alanine (133.3 mg, 0.705 mmol) were dissolved in 5 mL methylene chloride. DMAP (96.9 mg, 0.793 mmol) was added, followed by EDCI (258.7 mg, 1.349 mmol). After stirring at room temperature for 2 days the solvent was removed in a stream of nitrogen. The residue was dissolved in 0.1 M HCl and the solution was extracted four times with methylene chloride. The combined organic extracts were dried over MgSO$_4$ and concentrated to give a white solid that was purified by chromatography (silica gel, CHCl$_3$/MeOH 19:1) to yield 0.18 g (0.420 mmol, 66%) of 17 as a white solid. $^1$H-NMR (300 MHz, CDCl$_3$) δ 7.54 (b, NH), 6.30 (b, NH), 5.58 (b, NH), 4.66 (AB, A part, J=15.4 Hz, 1H), 4.47 (AB, B part, J=15.5 Hz, 1H), 4.35 (m, 1H), 3.51 (m, 4H), 3.35 (m, 2H), 2.72 (d, J=4.8 Hz, 3H), 2.51 (m, 2H), 2.41 (m, 2H), 2.20 (m, 1H), 2.10 (m, 1H), 1.98 (m, 2H), 1.37 (s, 9H).

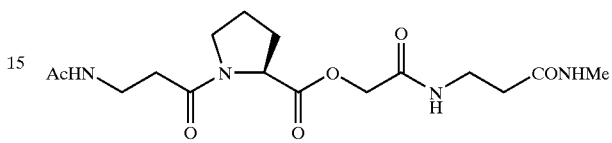

Compound 2. Compound 17 (0.18 g, 0.420 mmol) was dissolved in 2 mL 4 M HCl/dioxane and the solution was stirred for 1 hour at room temperature. HCl/dioxane was removed in a stream of nitrogen and the residue dried in vacuo. The deprotected depsipeptide and triethylamine (0.12 mL, 0.861 mmol) were dissolved in 5 mL methylene chloride. At 0° C. acetic anhydride (50 μL, 0.530 mmol) was added and the solution was stirred 1 hour at 0° C. and then allowed to warm to room temperature with stirring overnight. The solvent was removed in a stream of nitrogen and the residue dried in vacuo. The remaining white solid was purified by chromatography (silica gel, CHCl$_3$/MeOH 19:1) to yield 0.12 g (0.324 mmol, 77%) of 2 as a white solid. mp. 153.5–154° C., $^1$H-NMR (300 MHz, CDCl$_3$) 7.79 (d, J=4.4 Hz, NH), 7.32 (d, J=3.9 Hz, NH), 6.08 (b, NH), 4.75 (AB, A part, J15.4 Hz, 1H), 4.44 (AB, B part, J=15.3 Hz, 1H), 4.32 (m, 1H), 3.62–3.40 (m, 5H), 2.74 (d, J=4.8 Hz, 3H), 2.59–2.34 (m, 4H), 2.25–1.91 (m, 3H), 1.97 (s, 3H), $^{13}$C-NMR (75.5 MHz, CDCl$_3$) δ 171.57 (C), 171.30 (C), 170.63 (C), 167.42 (C), 62.78 (CH$_2$), 59.10 (CH), 47.02 (CH$_2$), 35.83 (CH$_2$), 35.54 (CH$_2$), 34.69 (CH$_2$), 33.75 (CH$_2$), 29.00 (CH$_2$), 26.17 (CH$_3$), 25.05 (CH$_2$), 22.83 (CH$_3$), IR (1 mM in CH$_2$Cl$_2$) 3452, 3334, 1757, 1669, 1635, 1539 cm$^{-1}$, EI MS m/e 370.1868 calc. for C$_{16}$H$_{26}$N$_4$O$_6$ 370.1852.

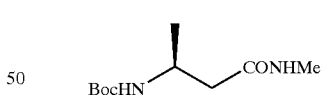

Methyl-(S)-3-(t-butoxycarbonylamino)butanoic amide (18). BOC-homoalanine (Podlech, J.; Seebach, D. (1995) *Liebigs Ann.* 1217) (0.44 g, 2.17 mmol) was dissolved in 5 mL methylene chloride. HOSu (376.4 mg, 3.27 mmol) was added and the solution cooled to 0° C. After addition of DCC (587.8 mg, 2.85 mmol) the solution was stirred 1 hour at 0° C., warmed to room temperature and stirred for an additional 2 hours. A stream of methylamine was bubbled through the suspension for 10 minutes, and stirring was continued overnight. The white precipitate was filtered off by suction filtration and the filtrate concentrated to give a pale yellow solid that was purified by chromatography (silica gel, CHCl$_3$/MeOH 19:1) to yield 0.41 g (1.90 mmol, 88%) Of BOC-homoalanine methylamide (18) as a white solid. $^1$H-NMR (300 MHz, CDCl$_3$) δ 6.11 (b, NH), 5.23 (b, NH), 3.92 (m, 1H), 2.75 (d, J=4.8 Hz, 3H), 2.35 (m, 2H), 1.39 (s, 9H), 1.17 (d, J=6.6 Hz, 3H).

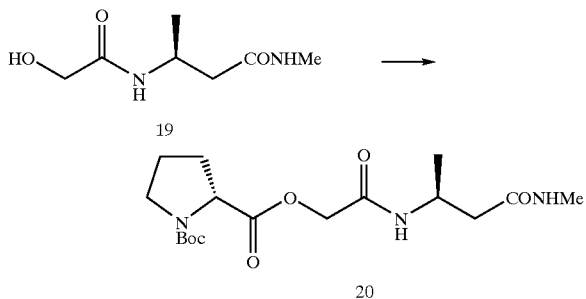

Compound 20. Compound 18 (0.41 g, 1.90 mmol) was dissolved in 2 mL of 4 M HCl/dioxane, and the solution was stirred at room temperature for 1 hour. HCl/dioxane was removed in a stream of nitrogen and the residue dried in vacuo. An activated ester solution was prepared by adding DCC (0.59 g, 2.86 mmol) to a solution of glycolic acid (175.5 mg, 2.31 mmol) and HOSu (421.9 mg, 3.67 mmol) in 5 mL DMF at 0° C. The suspension was stirred at 0° C. for 1 hour and then 2 hours at room temperature. The deprotected amide and triethylamine (0.32 mL, 2.30 mmol) were dissolved in 5 mL DMF and transferred into the activated ester solution. After stirring the resulting solution overnight at room temperature the white precipitate was filtered off by suction filtration and the filtrate concentrated to give a semisolid that was chromatographed (silica gel, CHCl$_3$/MeOH 9:1) to yield 0.42 g of impure 19, which was used in the next step without further purification.

Compound 19 (55 mg, 0.317 mmol, impure) and BOC-D-proline (148 mg, 0.688 mmol) were dissolved in 2 mL DMF. DMAP (10.0 mg, 0.082 mmol) was added, followed by DCC (171.4 mg, 0.831 mmol). After stirring the resulting suspension for 1 day at room temperature the white precipitate was filtered off by suction filtration and the filtrate concentrated. The remaining semisolid was purified by chromatography (silica gel, CHCl$_3$/MeOH 19:1) to yield 52.1 mg (0.140 mmol, 44%) of 20. $^1$H-NMR (300 MHz, CDCl$_3$) δ 7.53 (d, J=6.3 Hz, NH minor rotamer 21%), 7.30 (d, J=7.4 Hz, NH major rotamer 79%), 6.35 (b, NH major rotamer 84%), 6.13 (b, NH minor rotamer 16%), 4.74 (AB, A Part, J=15.4 Hz, 1H), 4.44 (AB, B part, J=15.4 Hz, 1H), 4.28 (m, 2H), 3.45 (m, 2H), 2.72 (d, J=4.8 Hz, 3H), 2.41 (dA-B, A part, J=7.4 Hz, 14.3 Hz, 1H), 2.31 (dAB, B part, J=5.3 Hz, 14.3 Hz, 1H), 2.23 (m, 1H), 1.98 (m, 2H), 1.88 (m, 1H), 1.43 (s, 9H), 1.25 (d, J=6.8 Hz, 3H).

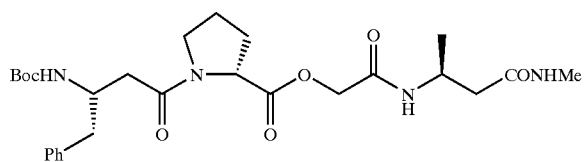

Compound 21. Compound 20 (52.1 mg, 0.140 mmol) was dissolved in 1 mL 4 M HCl/dioxane and the solution was stirred for 1 hour at room temperature. HCl/dioxane was removed in a stream of nitrogen and the residue dried in vacuo. The deprotected depsipeptide and BOC-homophenylalanine (42.5 mg, 0.152 mmol) were dissolved in 5 mL methylene chloride. DMAP (32.4 mg, 0.265 mmol) was added, followed by EDCI (59.4 mg, 0.310 mmol). After stirring at room temperature for 2 days the solvent was removed in a stream of nitrogen. The residue was dissolved in 0.1 M HCl, and the solution was extracted three times with methylene chloride. The combined organic extracts were dried over MgSO$_4$ and concentrated to give a colorless glass that was purified by chromatography (silica gel, CHCl$_3$/MeOH 19:1) to yield 62.8 mg (0.118 mmol, 84%) of 21. $^1$H-NMR (300 MHz, CDCl$_3$) δ 7.36 (b, NH), 7.31–7.12 (m, 5H), 6.43 (b, NH), 5.22 (b, NH), 4.82 (AB, A part, J=14.9 Hz, 1H), 4.49 (m, 2H), 4.41 (AB, B part, J=15.6 Hz, 1H), 4.21 (m, 1H), 3.52 (m, 1H), 3.32 (m, 1H), 2.89 (m, 1H), 2.78 (m, 1H), 2.71 (d, J=4.8 Hz, 3H), 2.46 (m, 3H), 2.40 (m, 1H), 2.24 (m, 1H), 2.12–1.89 (m, 3H), 1.38 (s, 9H), 1.25 (d, J=6.8 Hz, 3H).

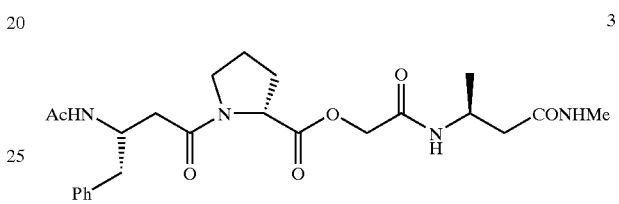

Compound 3. Compound 21 (62.8 mg, 0.118 mmol) was dissolved in 1 mL 4 M HCl/dioxane and the solution was stirred for 1 hour at room temperature. HCl/dioxane was removed in a stream of nitrogen and the residue dried in vacuo. The deprotected depsipeptide and triethylamine (90 μL, 0.646 mmol) were dissolved in 1 mL methylene chloride. At 0° C. acetic anhydride (35 μL, 0.371 mmol) was added and the solution was stirred 1 hour at 0° C. and then allowed to warm to room temperature with stirring overnight. The solvent was removed in a stream of nitrogen and the residue dried in vacuo. The residue was purified by chromatography (silica gel, CHCl$_3$/MeOH 19:1) to yield 52.1 mg (0.110 mmol, 193%) of 3. mp. 128–129° C., $^1$H-NMR (300 MHz, CDCl$_3$) δ 7.49 (d, J=8.5 Hz, NH), 7.31–7.16 (m, 5H), 6.80 (d, J=8.5 Hz, NH), 6.35 (m, NH), 4.73 (AB, A part, J=15.1 Hz, 1H), 4.49 (m, 1H), 4.45 (AB, B part, J=15.4 Hz, 1H), 4.38 (m, 2H), 3.55 (m, 1H), 3.28 (m, 1H), 2.99 (dAB, A part, J=6.2 Hz, 13.4 Hz, 1H), 2.88 (dAB, B part, J=8.5 Hz, 13.6 Hz, 1H), 2.72 (d, J=4.8 Hz, 3H), 2.55 (dAB, A part, J=5.2 Hz, 15.6 Hz, 1H), 2.43 (dAB, B part, J=5.9 Hz, 15.5 Hz, 1H), 2.45 (d, J=6.3 Hz, 2H), 2.25 (m, 1H), 2.21–1.89 (m, 3H), 1.93 (s, 3H), 1.26 (d, J=6.6 Hz, 3H), $^{13}$C-NMR (75.5 MHz CDCl$_3$) δ 170.90 (C), 170.31 (C), 169.75 (C), 128.93 (CH), 128.32 (CH), 126.40 (CH), 62.60 (CH$_2$), 58.89 (CH), 47.31 (CH$_2$), 42.44 (CH, CH$_2$) 39.57 (CH$_2$), 36.22 (CH$_2$), 28.92 (CH$_2$), 25.96 (CH$_3$), 24.94 (CH$_2$), 23.02 (CH$_3$), 20.21 (CH$_3$), IR (1 mM in CH$_2$Cl$_2$) 3452, 3433, 3346 cm$^{-1}$, EI MS m/e 474.2474 calc. for C$_{24}$H$_{34}$N$_4$O$_6$ 474.2478.

Construction of polypeptides using any type of β-amino acid can be accomplished using conventional and widely recognized solid-phase or solution-phase synthesis. Very briefly, in solid-phase synthesis, the desired C-terminal amino acid residue is linked to a polystyrene support as a benzyl ester. The amino group of each subsequent amino acid to be added to the N-terminus of the growing peptide chain is protected with Boc, Fmoc, or another suitable protecting group. Likewise, the carboxylic acid group of each subsequent amino acid to be added to the chain is activated with DCC and reacted so that the N-terminus of the growing chain always bears a removable protecting group. The process is repeated (with much rinsing of the beads between each step) until the desired polypeptide is completed. In the classic route, the N-terminus of the growing chain is protected with a Boc group, which is removed using trifluoracetic acid, leaving behind a protonated amino group. Triethylamine is used to remove the proton from the N-terminus of the chain, leaving the free amino group, which is then reacted with the activated carboxylic acid group from a new protected amino acid. When the desired chain length is reached, a strong acid, such as hydrogen bromide in trifluoracetic acid, is used to both cleave the C-terminus from the polystyrene support and to remove the N-terminus protecting group.

The preferred solid-phase synthesis used herein is shown in Reaction 7:

REACTION 7

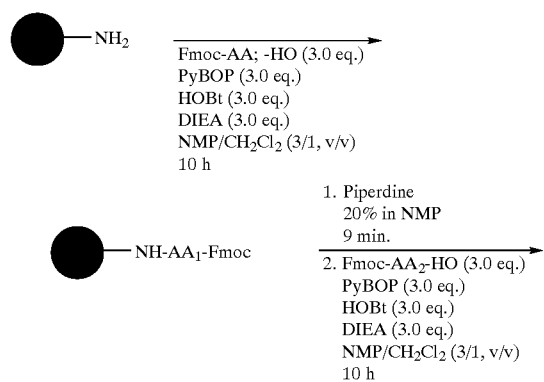

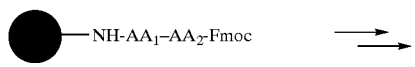

$AA_n$ = incoming amino acid to be added to chain
Fmoc =- the protecting group 9-fluorenylmethyloxycarbonyl
NMP = N-methyl pyrrolidone
EDT = Ethanedithiol
PyBOP = benzotriazol-1-yloxytripyrrolidinophosphonium hexafluorophosphate
HOBt = N-hydroxy-benzotriazole
DIEA = diisopropylethyl amine Solid-phase peptide synthesis is widely employed and well know. Consequently, it will not be described in any further detail here.

Solution phase synthesis, noted above, can also be used with equal success. For example, solution-phase synthesis of a β-peptide chain containing alternating residues of unsubstituted cyclohexane rings and amino-substituted cyclohexane rings proceeds in conventional fashion as outlined in Reaction 8:

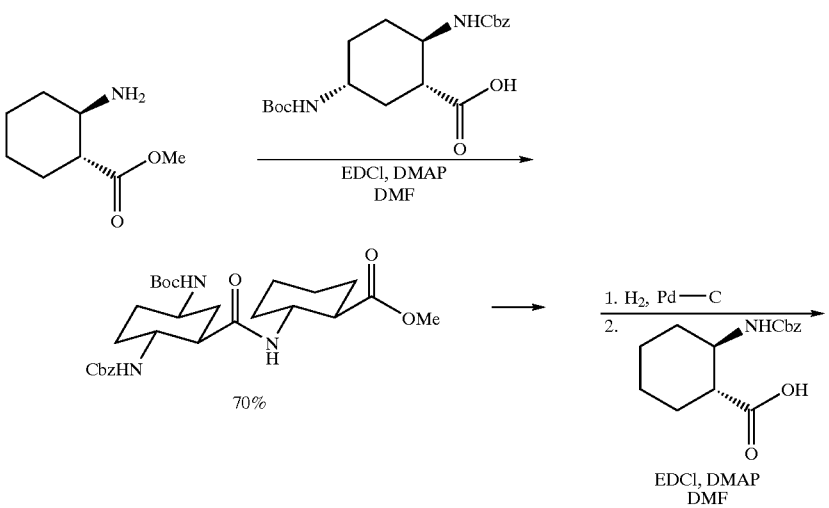

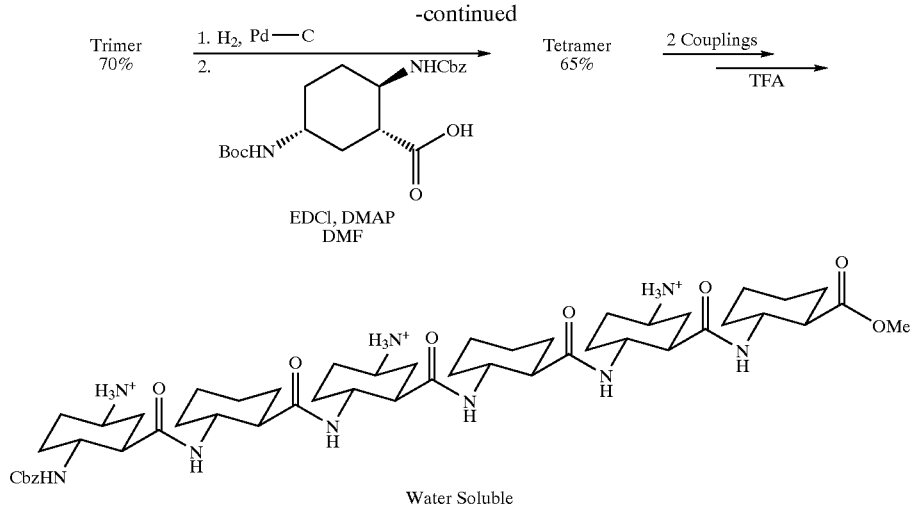

Reaction 8 works with equal success to build peptides wherein the residues are the same or different.

Reaction 9 is an illustration of a homologation reaction combined with conventional solution-phase peptide synthesis which yields a β-peptide having acyclic-substituted residues alternating with ring-constrained residues:

As noted above, the β-peptides of the present invention can be substituted with any number of substituents, including hydroxy, linear or branched $C_1$–$C_6$-alkyl, alkenyl, alkynyl; hydroxy-$C_1$–$C_6$-alkyl, amino-$C_1$–$C_6$-alkyl, $C_1$–$C_6$-alkyloxy, $C_1$–$C_6$-alkyloxy-$C_1$–$C_6$-alkyl, amino, mono- or di-$C_1$–$C_6$-alkylamino, carboxamido, carboxamido-$C_1$–$C_6$-

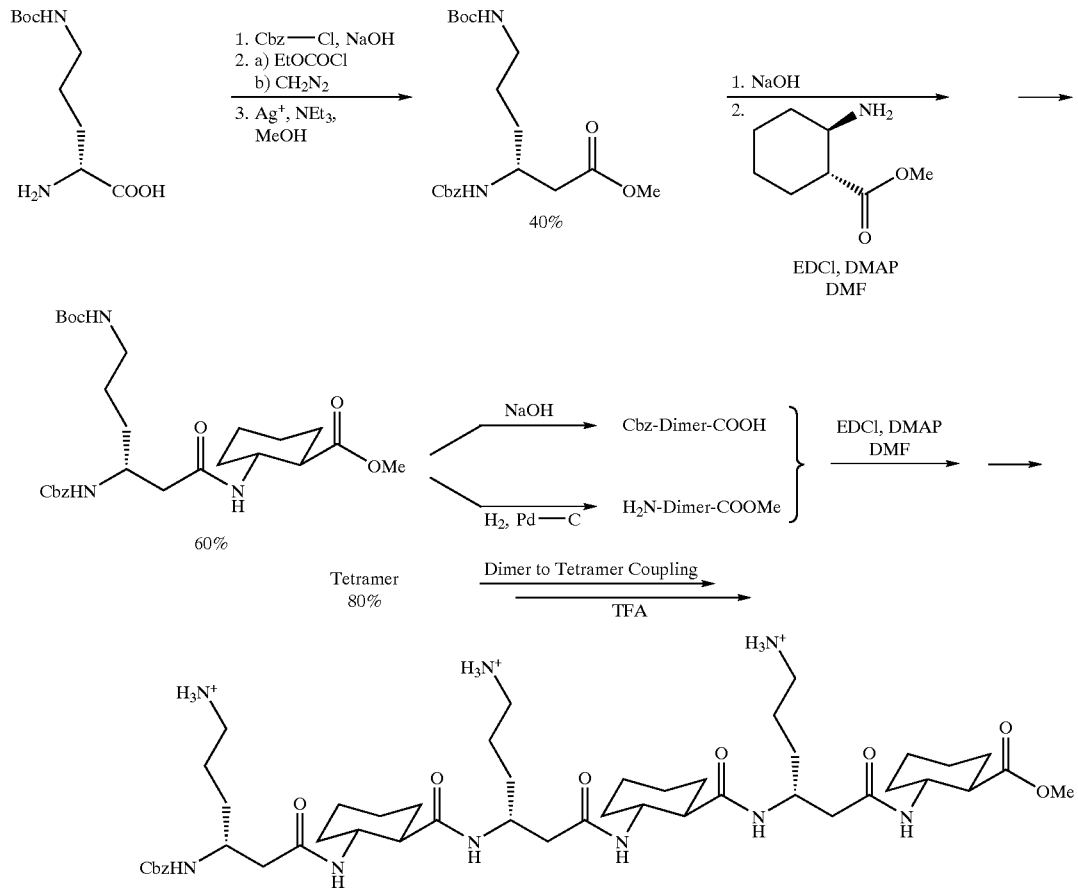

alkyl, sulfonamido, sulfonamido-$C_1$–$C_6$-alkyl, urea, cyano, fluoro, thio, $C_1$–$C_6$-alkylthio, mono- or bicyclic aryl, mono- or bicyclic heteraryl having up to 5 heteroatoms selected from N, O, and S; mono- or bicyclic aryl-$C_1$–$C_6$-alkyl, heteroaryl-$C_1$–$C_6$-alkyl, and combinations thereof. Effecting such substitutions is well within the set of skills possessed by a synthetic peptide chemist.

For example, appending a sulfonamido moiety to the cylic backbone substituent can be accomplished in conventional fashion using Reaction 10.

Compound 63: Compound 61 (90 mg) was dissolved in 4 N HCl in dioxane (2.0 ml). The reaction mixture was stirred for 1.5 hours. The dioxane was then removed in vacuo. The residue was dissolved in pyridine (2.0 ml), then cooled to 0° C. in an ice-bath.

Methanesulfonylchloride (71 μl) was added dropwise. After the addition, the reaction mixture was stirred at room temperature for 12 hours. The pyridine was then removed in vacuo. The residue was taken up in ethyl acetate (50 ml). The mixture was washed with dilute brine (2×10 ml), dried over $MgSO_4$, and concentrated to give the clean product as a colorless oil (70 mg) in 82% yield.

Compound 64: Compound 62 (30 mg) was dissolved in 4 N HCl in dioxane (2.0 ml). The reaction mixture was stirred for 1.5 hours. The dioxane was then removed in vacuo. The residue was dissolved in pyridine (1.0 ml), then cooled to 0° C. in an ice-bath. Toluenesulfonylchloride (63 mg) was added in portions. After the addition, the reaction mixture was stirred at room temperature for 12 tours. The pyridine was then removed in vacuo. The residue was taken up in methylene chloride/dithyl ether (1/1, v/v, 100 ml). The mixture was washed with dilute brine (3×20 ml), dried over $MgSO_4$, and concentrated to give a liquid residue. The crude product was purified by column chromatography with ethyl acetate/hexane (4/6, v/v).

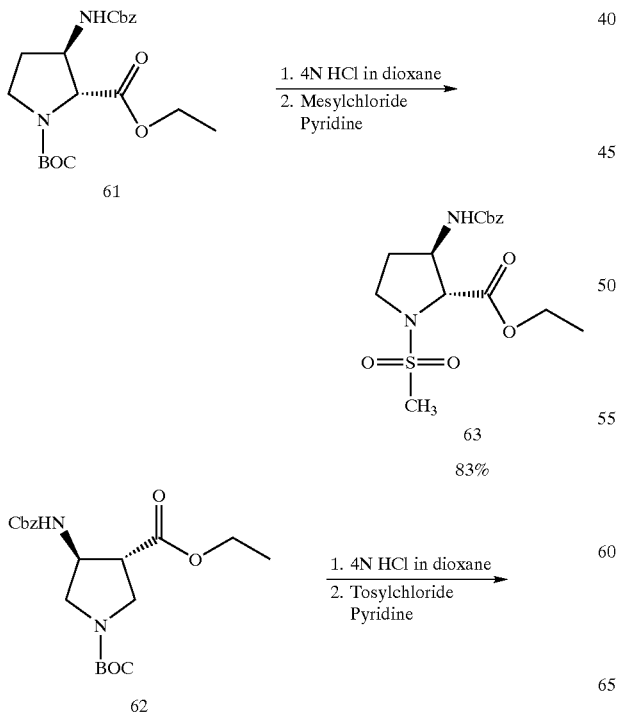

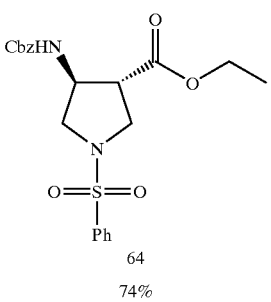

as eluent to give the clean product as a colorless oil (25 g) in 74% yield.

Analogous reactions will append a carboxyamido group.

β-peptide residues having a hydroxyalkyl substituent either trans or cis to the peptide backbone carbonyl group (and thereby providing a hydroxy group for further functionalization) can be synthesized as shown in Reactions 11 and 12, respectively:

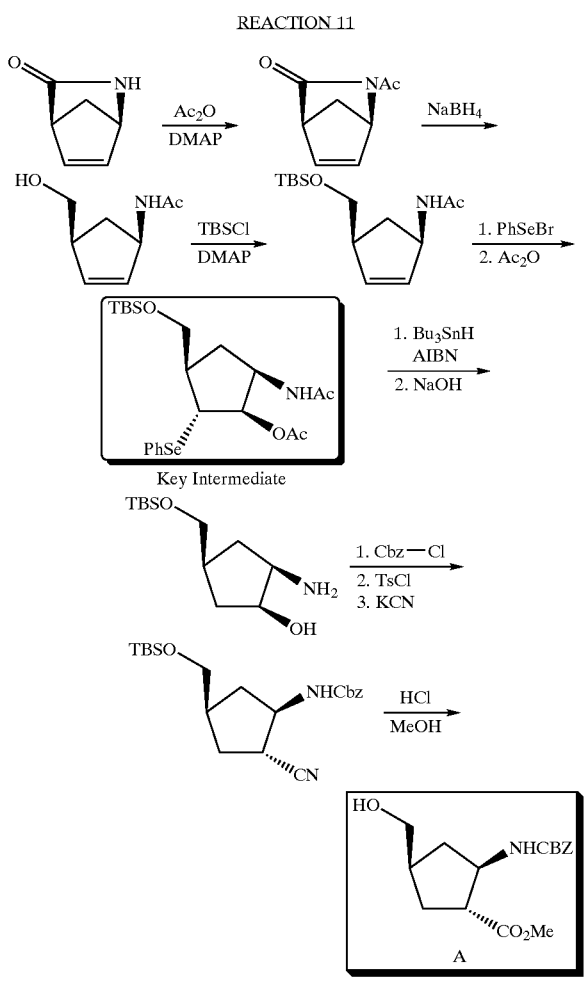

REACTION 12

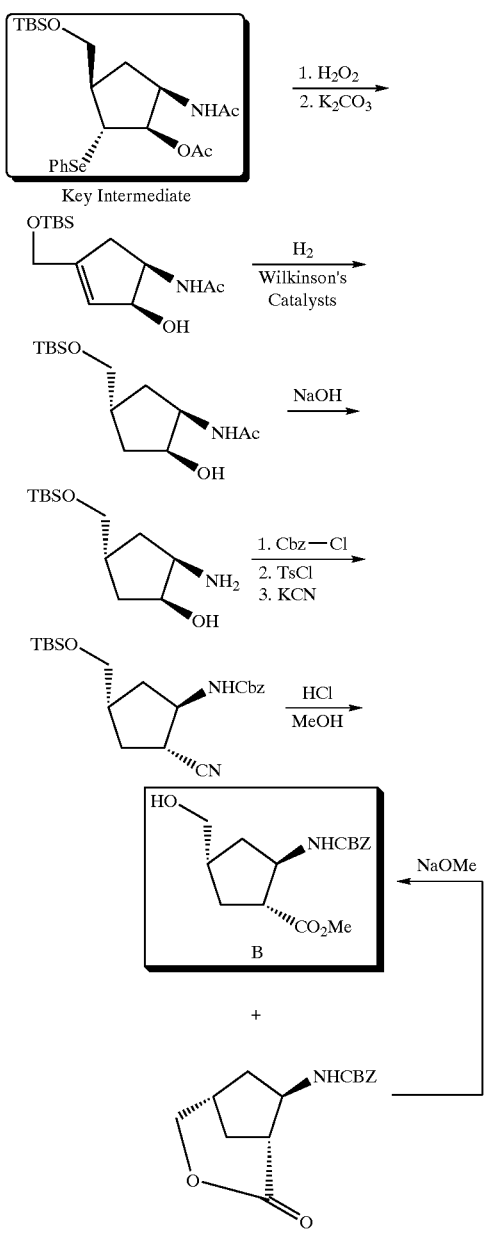

Antimicrobial Activity With Low Hemolytic Activity:

As demonstrated in the Examples, pharmaceutical compositions containing the β-peptide compounds described herein are selectively antimicrobial. In short, the compounds exhibit good antimicrobial activity, both MIC and MBC, while simultaneously exhibiting very low hemolytic activity. Consequently, the subject compounds are useful in the formulation of pharmaceutical compositions for the treatment of microbial infections because they inhibit microbial growth at low concentrations without lysing human cells.

Pharmaceutical Compositions:

Administration and Pharmaceutical Unit Dosage Forms:

The compounds described herein being effective to inhibit the growth of microbial cells, the compounds are suitable for the therapeutic treatment of microbial infestation (infection, etc.) in mammals, including humans. Microbial cell growth inhibition at pharmacologically-acceptable concentrations has been shown in four different types of bacteria (see Examples 10 and 11).

Administration of the β-peptides to a human or non-human patient can be accomplished by any means known. The preferred administration route is parenteral, including intravenous administration, intraarterial administration, intratumor administration, intramuscular administration, intraperitoneal administration, and subcutaneous administration in combination with a pharmaceutical carrier suitable for the chosen administration route. The treatment method is also amenable to oral administration.

It must be noted, as with all pharmaceuticals, the concentration or amount of the β-peptide administered will vary depending upon the severity of the ailment being treated, the mode of administration, the condition and age of the subject being treated, and the particular β-peptide or combination of β-peptides being used.

The compounds can be administered in the form of tablets, pills, powder mixtures, capsules, injectables, solutions, suppositories, emulsions, dispersions, food premixes, and in other suitable forms. The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly (vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form may also contain non-toxic auxiliary substances such as emulsifying, preserving, or wetting agents, and the like.

Solid forms, such as tablets, capsules and powders, can be fabricated using conventional tabletting and capsule-filling machinery, which is well known in the art. Solid dosage forms may contain any number of additional non-active ingredients known to the art, including excipients, lubricants, dessicants, binders, colorants, disintegrating agents, dry flow modifiers, preservatives, and the like.

Liquid forms for ingestion can be formulated using known liquid carriers, including aqueous and non-aqueous carriers, suspensions, oil-in-water and/or water-in-oil emulsions, and the like. Liquid formulation may also contain any number of additional non-active ingredients, including colorants, fragrance, flavorings, viscosity modifiers, preservatives, stabilizers, and the like.

For parenteral administration, the subject compounds may be administered as injectable dosages of a solution or suspension of the compound in a physiologically-acceptable diluent or sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers.

The pharmaceutical unit dosage chosen is preferably fabricated and administered to provide a concentration of drug at the point of contact with the microbial cell of from 1 μM to 10 mM. More preferred is a concentration of from 1 to 100 μM. This concentration will, of course, depend on the chosen route of administration and the mass of the subject being treated.

Conformational Analysis

EXAMPLES

The following Examples are included herein solely to provide a more complete understanding of the invention.

The Examples do not limit the scope of the invention disclosed and claimed herein in any fashion.

Example 1

Amide Proton Exchange in trans-ACHC Dimer and Hexamer:

Amide proton exchange is one of the most powerful methods for assessing conformational stability of peptides and proteins; adoption of a stable intramolecularly hydrogen-bonded conformation leads to diminution of the rate of exchange. NH/ND exchange behavior of the trans-ACHC hexamer relative to the corresponding dimer (which is too small to form a favorable internal hydrogen bond) shows that the hexamer adopts a very stable intramolecularly hydrogen-bonded folding pattern in methanol solution.

Figure 3:
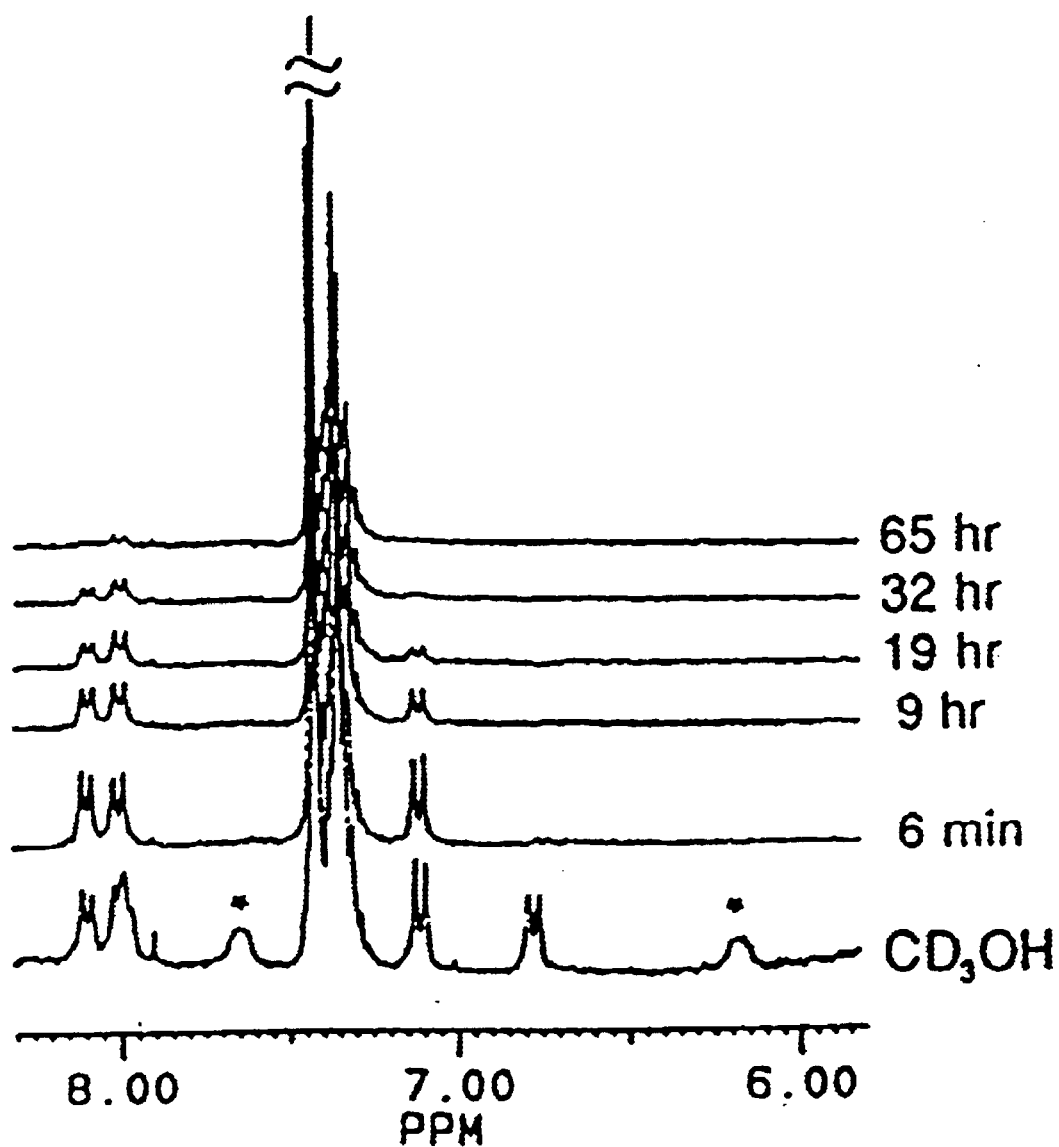
FIG. 3 depicts $^1$H NMR spectra for a solution containing 2 mM trans-ACHC dimer and 2 mM trans-ACHC hexamer. The bottom spectrum was obtained in CD$_3$OH with solvent suppression. The two NH resonances from the dimer are indicated with an asterisk (*). All other spectra were obtained in CD$_3$OD at the times indicated after dissolution of the sample. Data obtained on a Bruker 300 MHz spectrometer at 20° C.

To ensure a direct comparison, this Example was conducted with solutions containing 2 mM of the trans-ACHC dimer and 2 mM of the trans-ACHC hexamer. The $^1$H NMR results are shown in FIG. 3. Upon dissolution of the 1:1 dimer:hexamer mixture in $CD_3OD$, the amide proton and the urethane proton of the dimer (marked with asterisks) are completely exchanged within 6 min, according to $^1$H NMR (FIG. 3). In contrast, three of the six amide protons of the trans-ACHC hexamer show strong resonances at this point.

One of these protected protons exchanges within a ca. 20 h, but the other two require >2 days for complete exchange. Thus, two of the amide protons of hexamer display >100-fold protection from NH/ND exchange with $CD_3OD$, which indicates remarkable conformational stability for this six-residue foldamer in a hydrogen-bonding solvent. The two most protected protons of the hexamer are believed to be the amide groups of residues 2 and 3 (numbering from the N-terminus), although Applicants do not wish to be limited to this interpretation. The amide protons of residues 5 and 6 should exchange rapidly because they cannot be involved in 14-helical hydrogen bonds. The protons of residues 1 and 4 occur at the ends of the 14-helix in the hexamer crystal. The ends of α-helices in short α-peptides are "frayed" in solution, and similar fraying in the trans-ACHC hexamer would presumably enhance the NH/ND exchange rate. This conclusion is supported by the observation that only one of the NH resonances of the corresponding tetramer can be detected by $^1$H NMR within a few minutes of dissolution in $CD_3OD$, and this proton exchanges completely in less than an hour. Adoption of a stable folding pattern in solution requires the intrinsic rigidity of the trans-ACHC residue; dissolution of an analogous β-alanine hexamer in $CD_3OD$ causes all NH groups to exchange within 6 min. This Example shows that trans β-peptide oligomers constructed from an appropriately rigidified residue are highly predisposed to form a specific helix.

Example 2

Circular Dichroism and NOE's in trans-ACPC

As noted above, computational comparisons involving alternative cycloalkane-based β-amino acids and alternative β-peptide helices suggested that the trans-ACHC/14-helix combination would generate a stable β-peptide secondary structure. Using the same technique, the trans-ACPC/12-helix combination was predicted to be almost as favorable. This latter prediction is intriguing because there is no precedent for the 12-helix in the contradictory literature on polymers constructed from optically active β-amino acids. Among these polymers, poly(α-isobutyl-L-aspartate) has been particularly intensively studied, and proposed secondary structures include 14-, 16-, 18- and 20-helix, as well as sheet. Since the computational predictions regarding the trans-ACHC/14-helix relationship described above proved to be correct, the trans-ACPC/12-helix prediction was then explored.

Optically active trans-ACPC was prepared using the protocols described above, and β-peptides were generated via standard coupling methods. A trans-ACPC octamer displays the predicted 12-helical conformation in the solid state; all six of the possible 12-membered ring hydrogen bonds are formed. A trans-ACPC hexamer also displays the predicted 12-helical conformation in the solid state, with all four of the possible 12-membered ring hydrogen bonds formed. In both cases, the regular helix frays at the C-terminus, perhaps because the C-terminal ester group cannot serve as a hydrogen bond donor.

Figure 4:
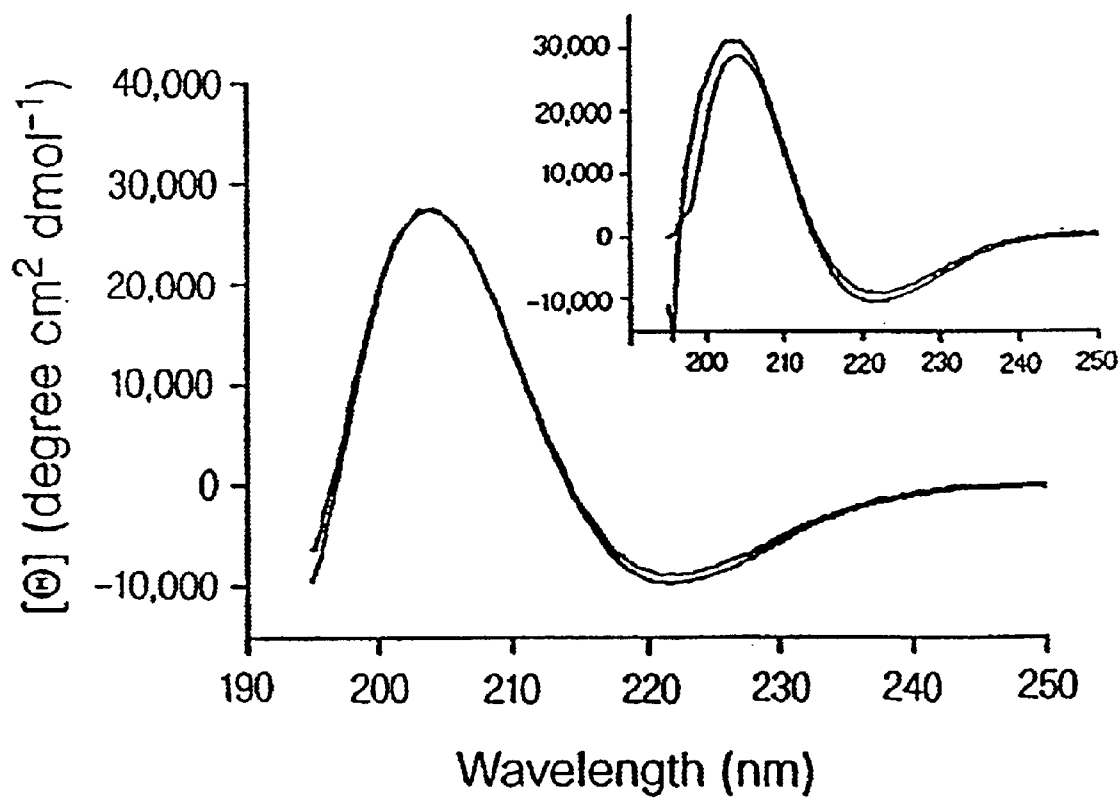
FIG. 4 is a circular dichroism (CD) plot for trans-ACPC hexamer in CH$_3$OH.

Circular dichroism data for trans-ACPC hexamer in $CH_3OH$ (FIG. 4) indicates the adoption of a distinctive secondary structure. The main graph in FIG. 4 depicts two virtually superimposable CD plots: one at a hexamer concentration of 2.0 mM, the other at hexamer concentration of 0.1 mM. Data were obtained on a Jasco J-715 instrument at 20° C. using a 1 mm pathlength. The inset graph shows the CD data at 0.1 mM and 0.02 mM using a 5 mm pathlength. The 14-helical conformation in β-peptides composed of acyclic residues has a far-UV CD signature comprising a maximum at ca. 197 nm, a zero crossing at ca. 207 nm, and minimum at ca. 215 nm. In contrast, the CD signature for the trans-ACPC hexamer is clearly different: maximum at ca. 204 nm, zero crossing at ca. 214 nm, and minimum at ca. 221 nm. Since the CD signature of trans-ACPC hexamer in $CH_3OH$ does not vary significantly between 2.0 mM and 0.02 mM, it is unlikely that aggregation occurs under these conditions.

Two-dimensional $^1$H NMR data obtained for the trans-ACPC hexamer in pyridine-$d_5$ and in $CD_3OH$ indicate that the 12-helix is highly populated in these solvents. Resonances of all NH groups, all protons at $C_\beta$ of each trans-ACPC residue, and nearly all protons at $C_\alpha$ of each residue were resolved in pyridine-$d_5$, and could be assigned via a combination of TOCSY and ROESY data. The N-terminal NH (residue 1) could be identified because it was the only one of the six amidic protons that did not show an NOE to $C_\alpha H$ of another residue (this NH also showed an NOE to the Boc methyl groups). The C-terminal residue could be identified because it had the only $C_\alpha H$ that did not show an NOE to an NH of another residue. Assignment of these terminal resonances allowed us to "walk through" the remaining backbone resonances by virtue of short-range $C_\alpha H_i \rightarrow NH_{i+1}$ NOEs.

The secondary structure of the trans-ACPC hexamer in pyridine-$d_5$ is defined by the long-range NOEs summarized in Table 1, below. $C_\beta H_i \rightarrow NH_{i+2}$ and $C_\beta H_i \rightarrow C_\alpha H_{i+2}$ NOEs are expected for the 12-helix. All four possible $C_\beta H_i \rightarrow NH_{i+2}$ NOEs were observed for the ACPC hexamer, as were two of the four $C_\alpha H_i \rightarrow C_\alpha H_{i+2}$ NOEs; NOEs consistent with the other two $C_\beta H_i \rightarrow C_\alpha H_{i+2}$ interactions were observed but could not be unambiguously assigned because of overlap of the $C_\alpha H$ resonances of residues 3 and 4. An NOE between NH of residue 3 and the Boc methyl groups provided further evidence for 12-helical folding. In $CD_3OH$, NOEs consistent with all of the long range NOEs detected in pyridine-$d_5$ were observed, and there did not appear to be any additional NOEs in $CD_3OH$. Interpretation of the $CD_3OH$ data was less definitive, however, because of greater overlap among proton resonances (especially for $C_\beta H$ of the trans-ACPC residues). The pattern of NOEs in CD$_3$OH was identical for 25 mM and 2.5 mM samples of the trans-ACPC hexamer; chemical shifts and line widths were also invariant between these two concentrations, suggesting that aggregation does not occur under these conditions.

TABLE 1

Inter-residue NOEs of hexamer 2 in pyridine-d$_5$

| Residue | H-atom | Residue | H-atom | NOE* |
|---|---|---|---|---|
| 1 | C$_\alpha$H | 2 | NH | Strong |
| 1 | C$_\beta$H | 2 | NH | Weak |
| 1 | C$_\beta$H | 3 | NH | Medium |
| 1 | C$_\beta$H | 3 | C$_\alpha$H | Medium† |
| 1 | CH$_3$(Boc) | 3 | NH | Strong |
| 1 | C$_\beta$H | 4 | NH | Weak |
| 2 | C$_\alpha$H | 3 | NH | Strong |
| 2 | C$_\beta$H | 4 | NH | Medium |
| 2 | C$_\beta$H | 4 | C$_\alpha$H | Medium† |
| 3 | C$_\alpha$H | 4 | NH | Strong |
| 3 | C$_\beta$H | 5 | NH | Medium |
| 3 | C$_\beta$H | 5 | C$_\alpha$H | Medium |
| 4 | C$_\alpha$H | 5 | NH | Strong |
| 4 | C$_\beta$H | 6 | NH | Medium |
| 4 | C$_\beta$H | 6 | C$_\alpha$H | Weak |
| 5 | C$_\alpha$H | 6 | NH | Strong |
| 5 | C$_\beta$H | 6 | NH | Weak |

*Strong, 2.3Å; medium 3.0Å; weak, 4.0Å.
†NOE present, but overlap of C$_\alpha$H of residues 3 and 4 prevents definite assignment.

NOE-restrained molecular dynamics simulations of the trans-ACPC hexamer generated 10 low-energy conformations. Superposition of these conformers shows a high degree of order (RMSD of backbone atoms <0.2 Å), with fraying at the C-terminus). The conformer from this set that is closest to the average agrees quite well with the crystal structure of the hexamer, although there is variation at the C-terminus and in individual cyclopentane ring conformations.

Figure 5:
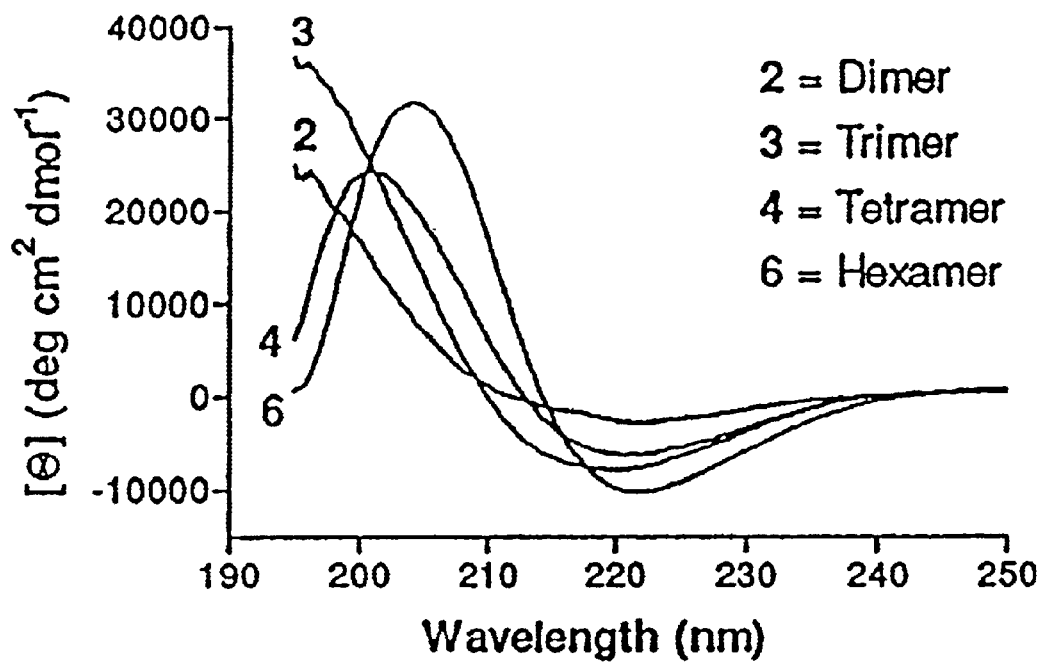
FIG. 5 is a CD plot comparing trans-ACPC dimer, trimer, tetramer and hexamer.
Figure 5:
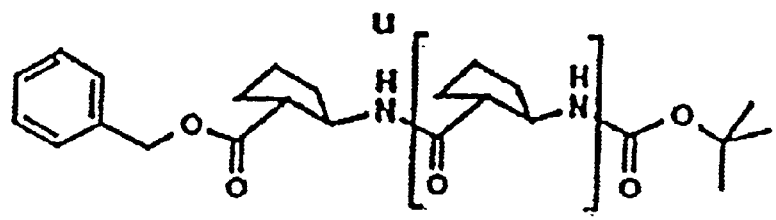

FIG. 5 shows CD data for the dimer, trimer, tetramer, and hexamer of trans-ACPC in methanol. A comparison between the dimer and the hexamer indicates the profound change in secondary structure which takes place as the peptide chain increases in length. The dimer is essentially unstructured. However, the tetramer clearly displays a CD curve indicative of 12-helical secondary structure.

This Example shows that short β-peptides of trans-ACPC have a high propensity to adopt the 12-helical folding pattern. In combination with the 14-helix formation by short oligomers of trans-ACHC, the present results indicate that β-peptide secondary structure can be profoundly and rationally altered by manipulating torsional preferences about the C$_\alpha$—C$_\beta$ bonds of individual residues.

Example 3

Amide Proton Exchange in Amino-substituted trans-ACHA/trans ACHA Dimers and Hexamers In this Example, amino-substituted-trans-ACHA (i.e., ACHA containing an exocyclic amino substituent) was synthesized according to Reaction 3, above. The amino-substituted-trans-ACHA was then coupled with unsubstituted trans-ACHA as shown in Reaction 7 to yield β-peptides wherein the residues alternate between unsubstituted-trans-ACHA and amino-substituted-trans-ACHA. These molecules were synthesized because it was anticipated that the amino group would be protonated in water and that the resulting positive charge would render these β-peptides water-soluble. They are indeed water-soluble.

Figure 6:
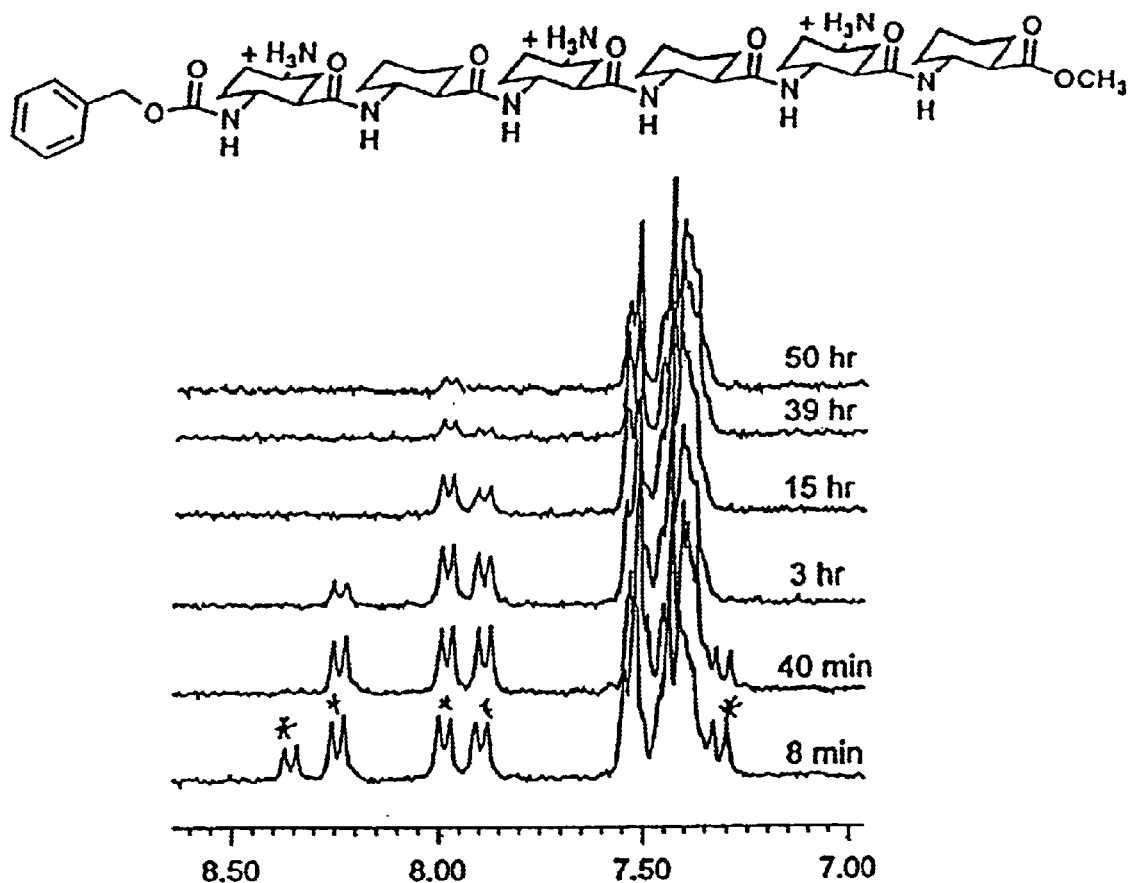
FIG. 6 depicts $^1$H NMR spectra for a solution containing 2 mM of a hexamer of alternating amino-substituted-trans-ACHA and trans-ACHA. All spectra were obtained in D$_2$O, 100 mM deuteroacetate buffer, pD 3.9, at the times indicated after dissolution of the sample. Data obtained on a Bruker 300 MHz spectrometer at 20° C.

The amide exchange of the dimer and the hexamer were then compared in the same fashion as described in Example 1 in order to probe for 14-helix formation in water. FIG. 6 depicts the two-dimensional $^1$H NMR data obtained for the alternating unsubstituted-trans-ACHA/amino-substituted-trans-ACHA hexamer in D$_2$O, 100 mM deuteroacetate buffer, pD 3.9. Hydrogen/deuterium exchange can be examined at five of the six backbone NH groups in this acidic D$_2$O solution. The spectra were taken at room temperature. Five NH peaks are observed (marked with asterisks) in the 8 minute plot. Each peak disappears at a different rate over the course of two days as the NH groups become ND groups. The protons slowest to exchange are those hydrogen bonded and buried in a folded secondary conformation.

Figure 7:
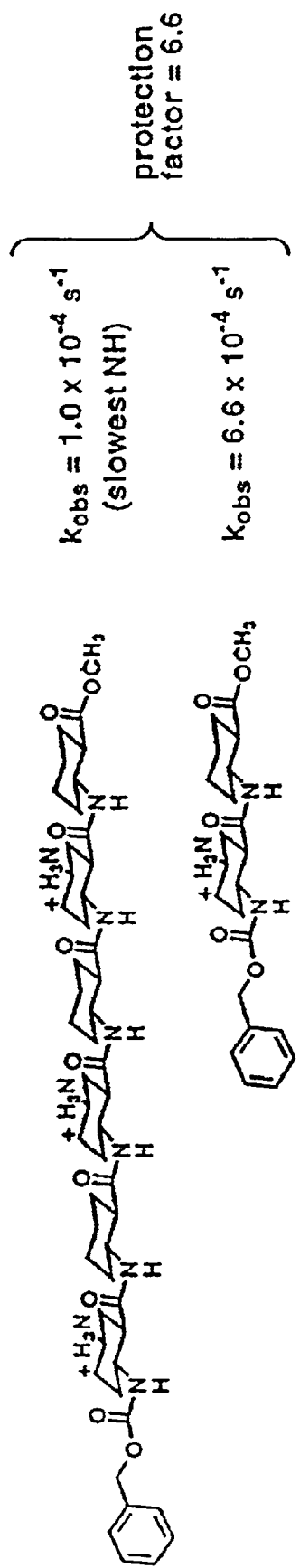
FIG. 7 is a comparison between the $k_{obs}$ for amide proton exchange in a hexamer of alternating amino-substituted-trans-ACHA and trans-ACHA and a dimer of alternating amino-substituted-trans-ACHA and trans-ACHA.

As shown in FIG. 7, the rate of amide proton exchange in the dimer had a k$_{obs}$ of 6.6×10$^{-4}$/sec. In contrast, the slowest amide proton exchange in the hexamer had a k$_{obs}$ of 1×10$^{-4}$/sec, more than 6-fold slower (protection factor=6.6). In other words, the slowest exchanging NH of the hexamer takes 6.6 times longer to exchange than the NH of the dimer (which is too small to adopt a folded conformation). This Example shows that there is substantial peptide folding of the alternating unsubstituted-trans-ACHA/amino-substituted-trans-ACHA hexamer in aqueous solution. The data strongly suggest that the hexamer is forming a 14-helix.

Example 4

Figure 8:
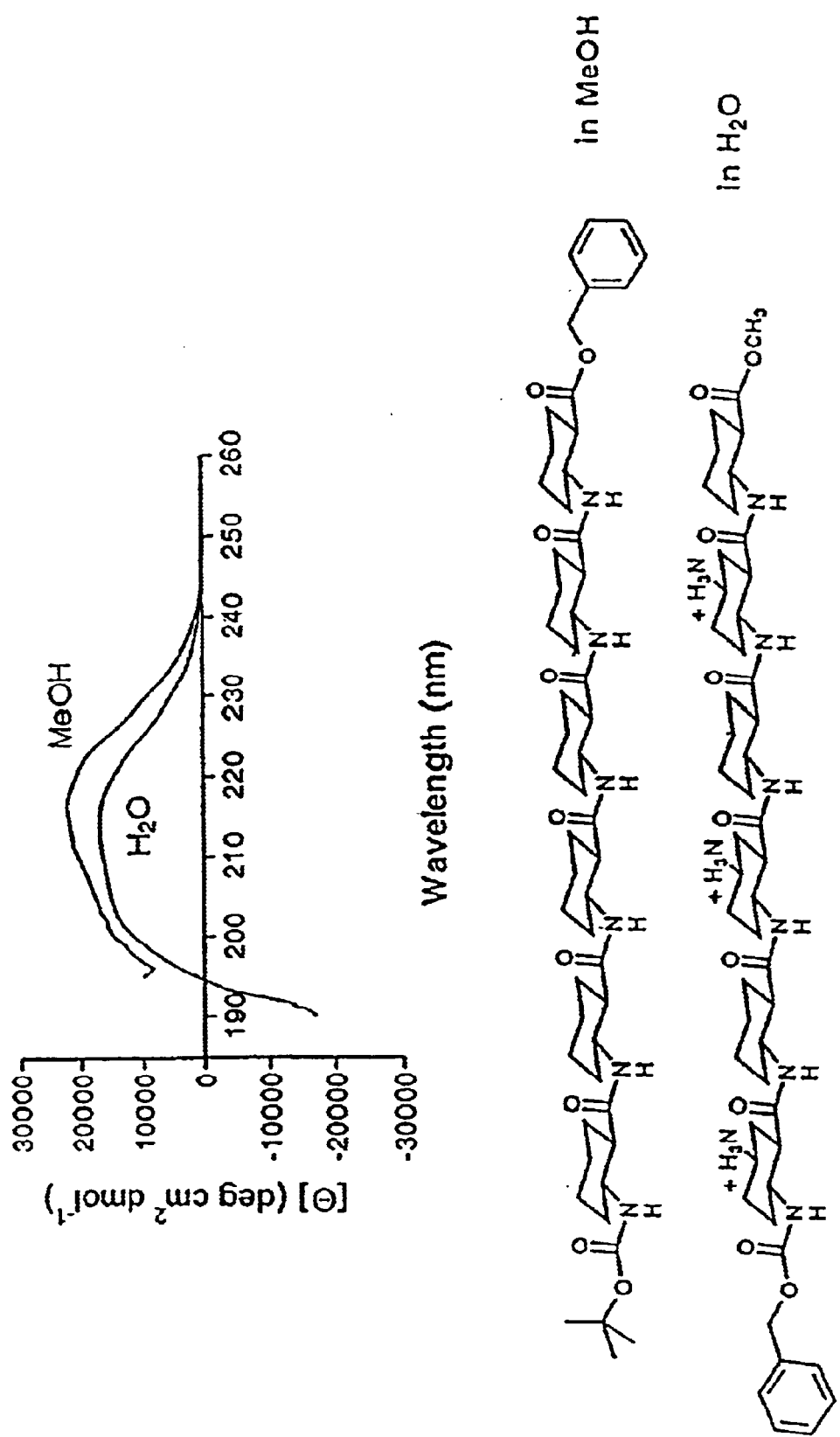
FIG. 8 is a comparison between the CD plot of a hexamer of alternating amino-substituted-trans-ACHA and trans-ACHA in water and the CD plot of a hexamer of trans-ACHC in methanol.

Comparison of CD Data From Amino-substituted trans-ACHA/trans-ACHA Hexamers and trans-ACHC In this Example, the CD data from the alternating hexamer described in Example 3 was compared with a hexamer of unsubstituted trans-ACHC. The trans-ACHC hexamer adopts a 14-helical conformation in methanol solution. Therefore, the CD plot for trans-ACHC should be representational of the 14-helix structure and can serve as a means of comparison for other peptides. FIG. 8 compares the CD data of trans-ACHC hexamer in methanol with the CD data of the alternating unsubstituted-trans-ACHA/amino-substituted-trans-ACHA described in Example 3. The similarity of the two plots provides strong evidence that the alternating hexamer adopts a 14-helical conformation in aqueous solution. In contrast, conventional peptides made from α-amino acids never show evidence of α-helicity where there are fewer than 10 residues.

Examples 3 and 4 in combination show that in addition to the substantial peptide folding indicated by the slow amide proton exchange rate of the alternating hexamer, the CD data strongly indicates that the alternating hexamer adopts a 14-helix secondary structure in aqueous solution.

Example 5

Figure 9:
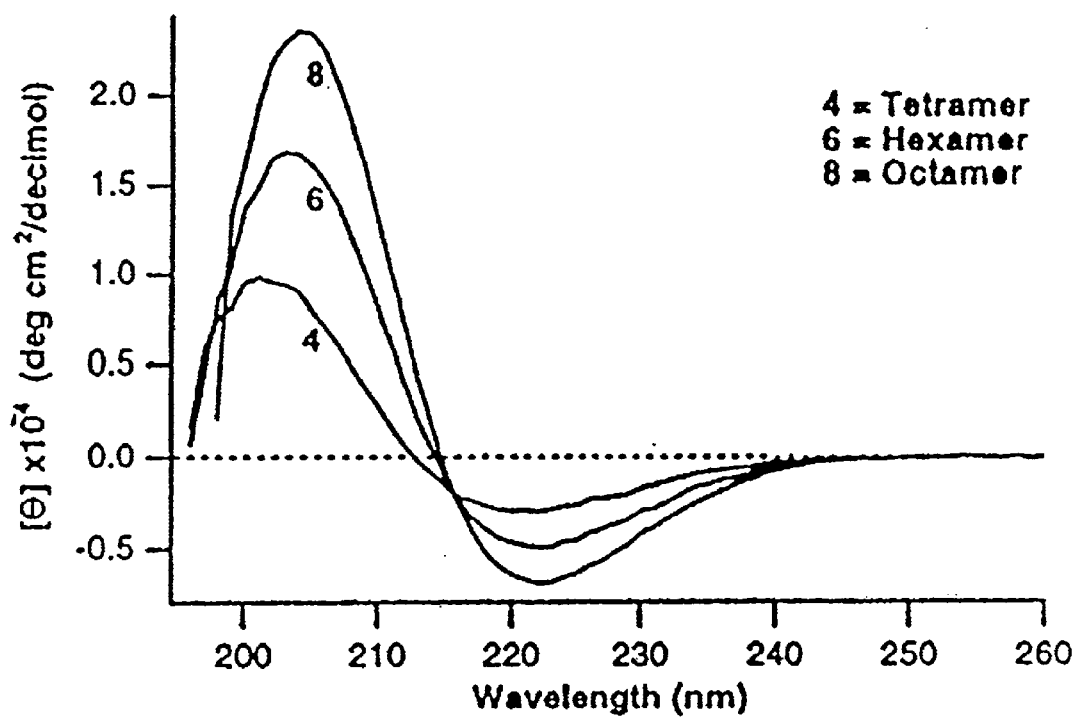
FIG. 9 is a comparison of CD data in methanol for a β-peptide tetramer, hexamer, and octamer containing alternating trans-ACPA residues and 4-pyrrolidinyl residues.
Figure 9:
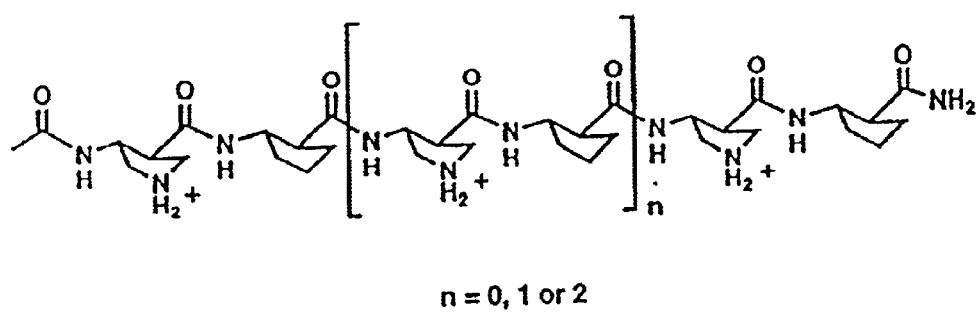

CD Data of β-Peptides Containing Alternating trans-ACPA Residues and 3-Amino-4-carboxy-pyrrolidinyl Residues In this Example, a β-amino acid containing a 3-amino-4-carboxy-pyrrolidinyl residue was synthesized according to Reaction 5, and coupled into a series of peptides with alternating trans-ACPA residues using conventional coupling methods (Reaction 7). CD data for the tetramer, hexamer, and octamer in this series were then gathered. The results, in methanol, are shown in FIG. 9. Note the distinct and increasing intensity of the characteristic maximum at about 205 nm and minimum at about 221 nm as the chain length increases.

Figure 10:
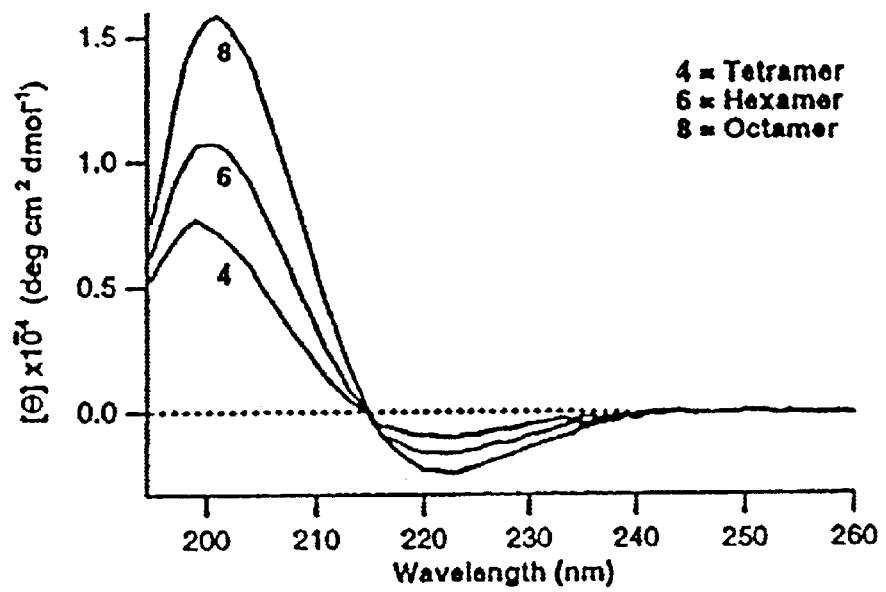
FIG. 10 is a comparison of CD data in water for a β-peptide tetramer, hexamer, and octamer containing alternating trans-ACPA residues and 4-pyrrolidinyl residues.
Figure 10:
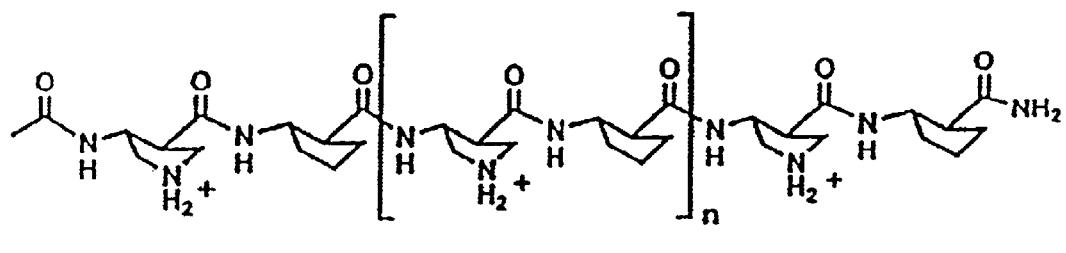

FIG. 10 shows another plot of CD data, in this instance using water as the solvent. Again, the maximum and minimum characteristic peaks increase in intensity with increasing chain length.

Figure 11:
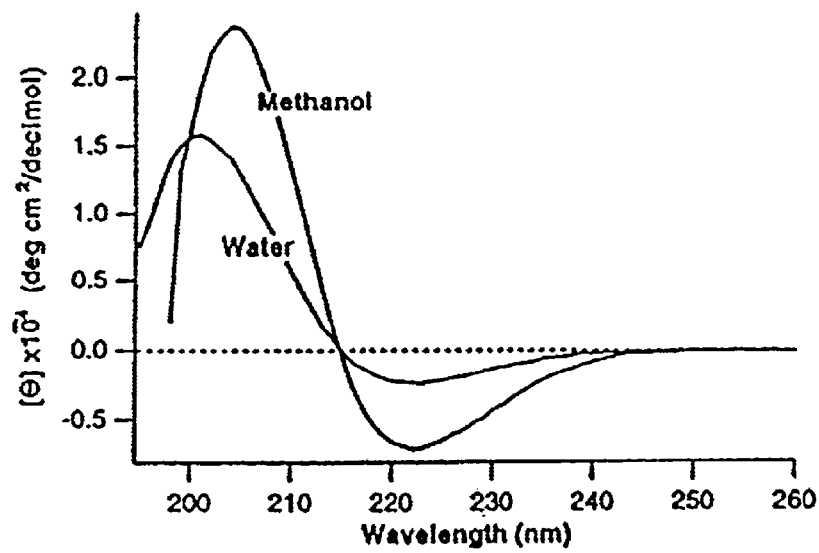
FIG. 11 is a superimposed plot of the CD data in water and the CD data in methanol for the octamer containing alternating trans-ACPA residues and 4-pyrrolidinyl residues.
Figure 11:
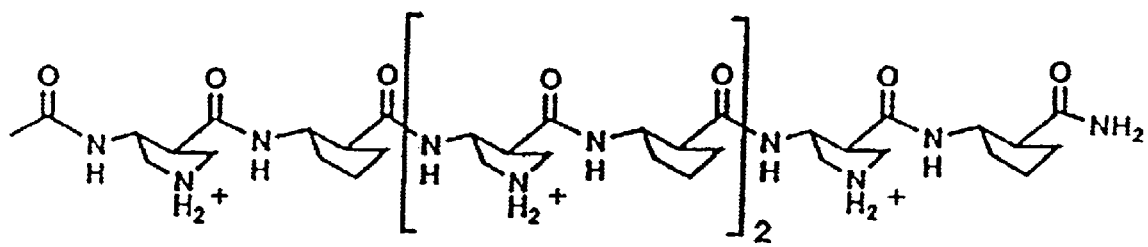

FIG. 11 is a direct comparison of the CD data in water versus the CD data in methanol for the alternating 4-pyrrolidinyl/trans-ACPA octamer. These data indicate that the 12-helix formation is only slightly less stable in water than it is in methanol.

Taken together, the CD data presented in this Example strongly indicate that the pyrrolidinyl β-peptides assume a 12-helix conformation in both methanol and aqueous solutions.

Example 6

Figure 12:
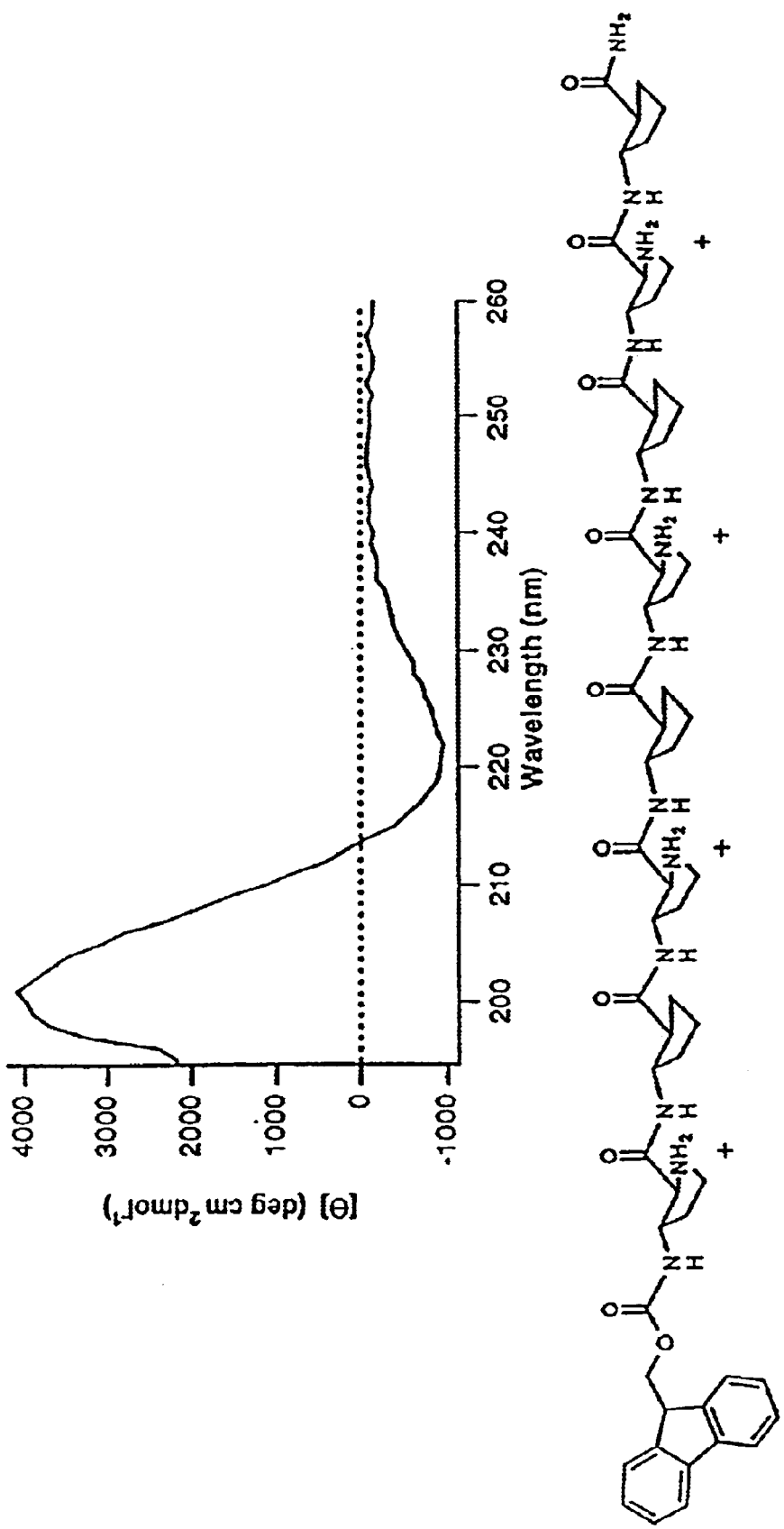
FIG. 12 is a CD spectrum in water of an octamer containing alternating trans-ACPA residues and 3-pyrrolidinyl residues.

CD Data of Octamer Containing Alternating trans-ACPA Residues and 3-Amino-2-carboxy-pyrrolidinyl Residues In this Example, a β-amino acid containing a 3-amino-2-carboxy-pyrrolidinyl residue was synthesized according to Reaction 4, and coupled into a peptide with alternating trans-ACPA residues using conventional coupling methods (Reaction 7). CD data for the octamer of this peptide was then gathered. The results, in aqueous solution, are shown in FIG. 12. This β-peptide clearly adopts the 12-helix conformation in water as evidenced by the characteristic maximum at about 205 nm and the characteristic minimum at about 221 nm.

This Example shows that the nitrogen heteroatom introduced in the pyrrolidinyl moiety can be located in different positions along the heterocyclic ring without adversely affecting the formation of the 12-helical structure in solution.

Example 7

Comparison of Secondary Structure in Amino-subsituted-trans-ACHC and β-Peptides Containing Aliphatic-substituted Residues In this Example, the CD spectrum of a β-peptide containing alternating residues of trans-ACHA and amino-substituted-trans-ACHA was compared to the CD spectrum of a "mixed" β-peptide comprising alternating residues of trans-ACHA and an acyclic β-amino acid bearing an aminopropyl substituent on the β-carbon of the backbone. The acyclic β-amino acid was synthesized and coupled to the trans-ACHA residue as detailed in Reaction 9, described above.

Figure 13:
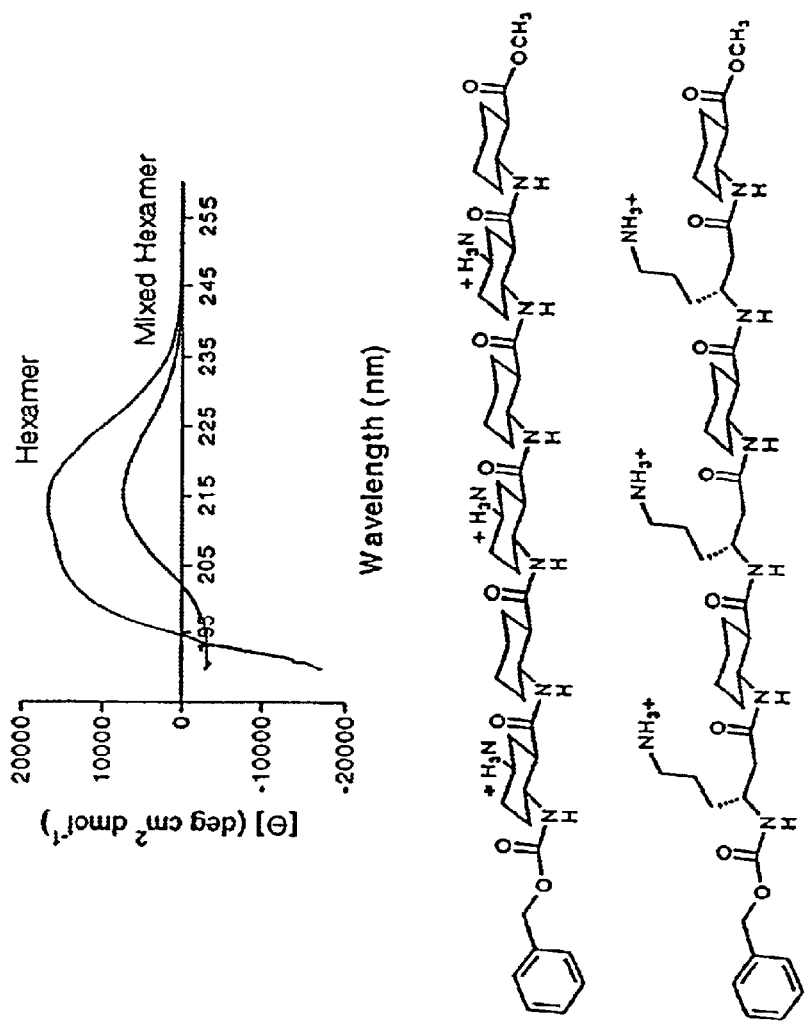
FIG. 13 is a comparison of CD spectra for a hexamer containing alternating residues of trans-ACHA and amino-substituted-trans-ACHA and for a "mixed" β-peptide hexamer comprising alternating residues of trans-ACHA and an acyclic β-amino acid bearing an aminopropyl substituent on the β-carbon of the backbone.

The CD data are presented in FIG. 13. While the removal of 3 cyclohexyl units clearly diminishes the extent of helix formation, the extent of helix formation in the mixed β-peptide is still significant. The data presented here indicate that β-peptides which include acyclic residues along with ring-constrained residues will adopt moderately stable secondary structures in solution.

Example 8

Infrared Analysis of Reverse Turn Using Linked Nipecotic Acid Moieties

Figure 14A:
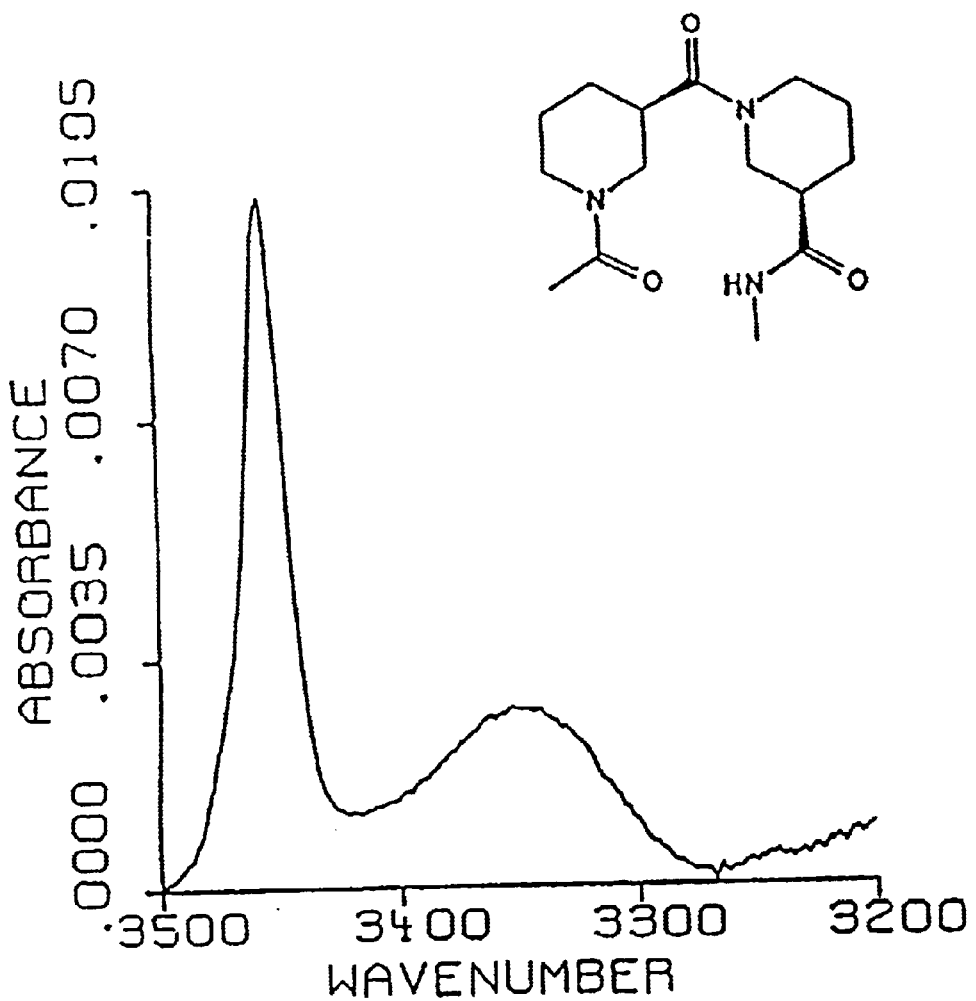
FIG. 14A shows the infrared spectrum of two linked nipecotic acid residues wherein the two residues have the same absolute configuration.
Figure 14B:
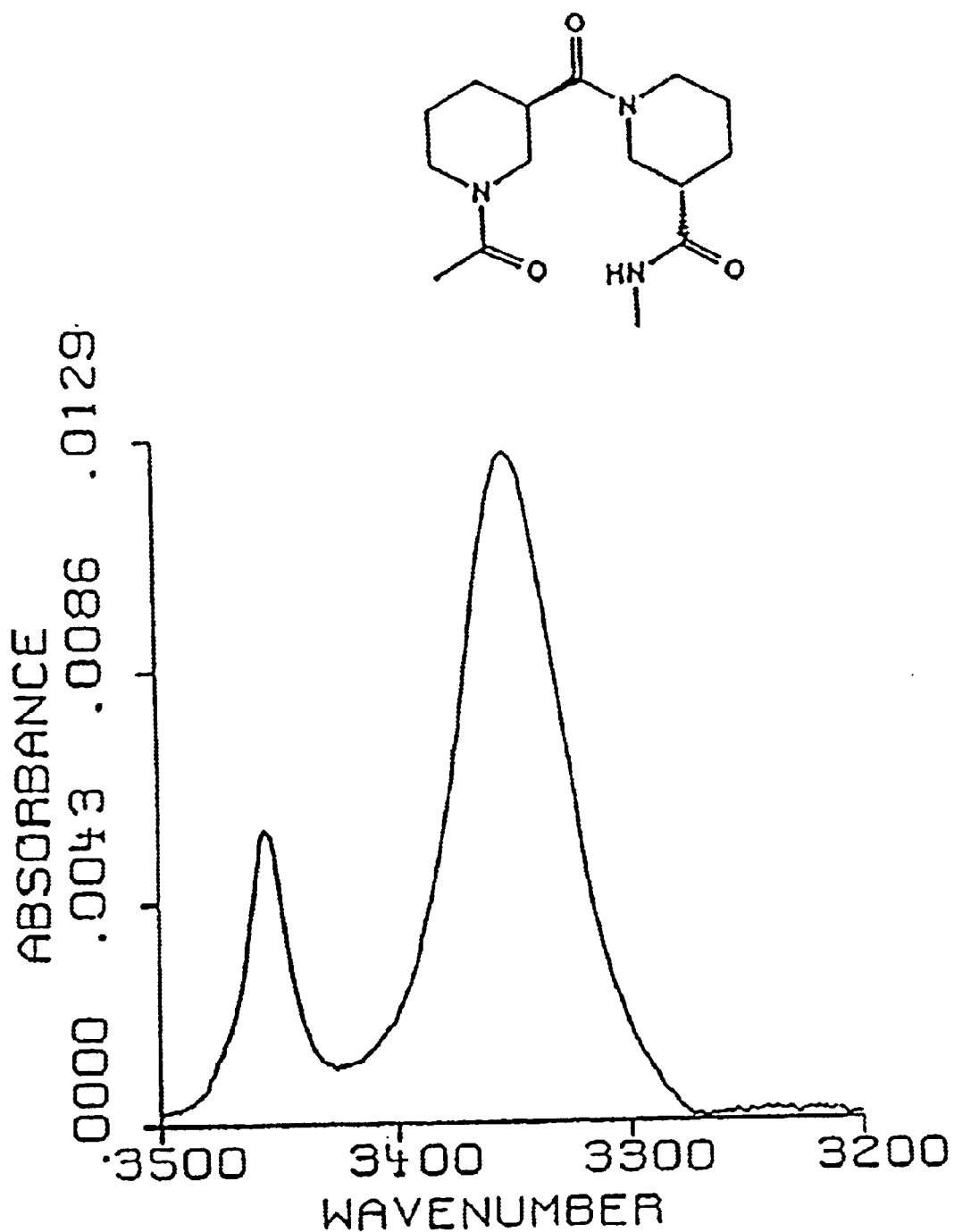
FIG. 14B shows the infrared spectrum of two linked nipecotic acid residues wherein the two residues have the opposite absolute configuration. This diastereomer acts as a reverse turn in β-peptides which adopt a sheet structure.

In this Example, two nipecotic acid residues were linked to each other to act as a reverse turn moiety. This was done using Reaction 6. FIG. 14A shows the IR spectrum for the diastereomer in which the two nipecotic acid residues have the same absolute configuration and FIG. 14B shows the IR spectrum for the diastereomer in which the two nipecotic acid residues have opposite absolute configuration. Both samples were taken in dilute solution (to minimize intermolecular hydrogen bonding) with solvent subtraction. As is clear from the diastereomer shown in FIG. 14A, there is little intramolecular hydrogen bonding as evidenced by the large peak at 3454 cm$^{-1}$ which is due to N—H units not involved in hydrogen bonding. This was as predicted from computer modeling studies.

In contrast, the spectrum shown in FIG. 14B for the heterochiral diastereomer exhibits a very large peak at 3350 cm$^{-1}$, indicative of hydrogen-bonded N—H groups.

This Example shows that synthetic reverse turn moieties can be constructed from two nipecotic β-amino acid residues having opposite configuration.

Example 9

X-Ray Crystallography of Synthetic Reverse Turn

Figure 16:
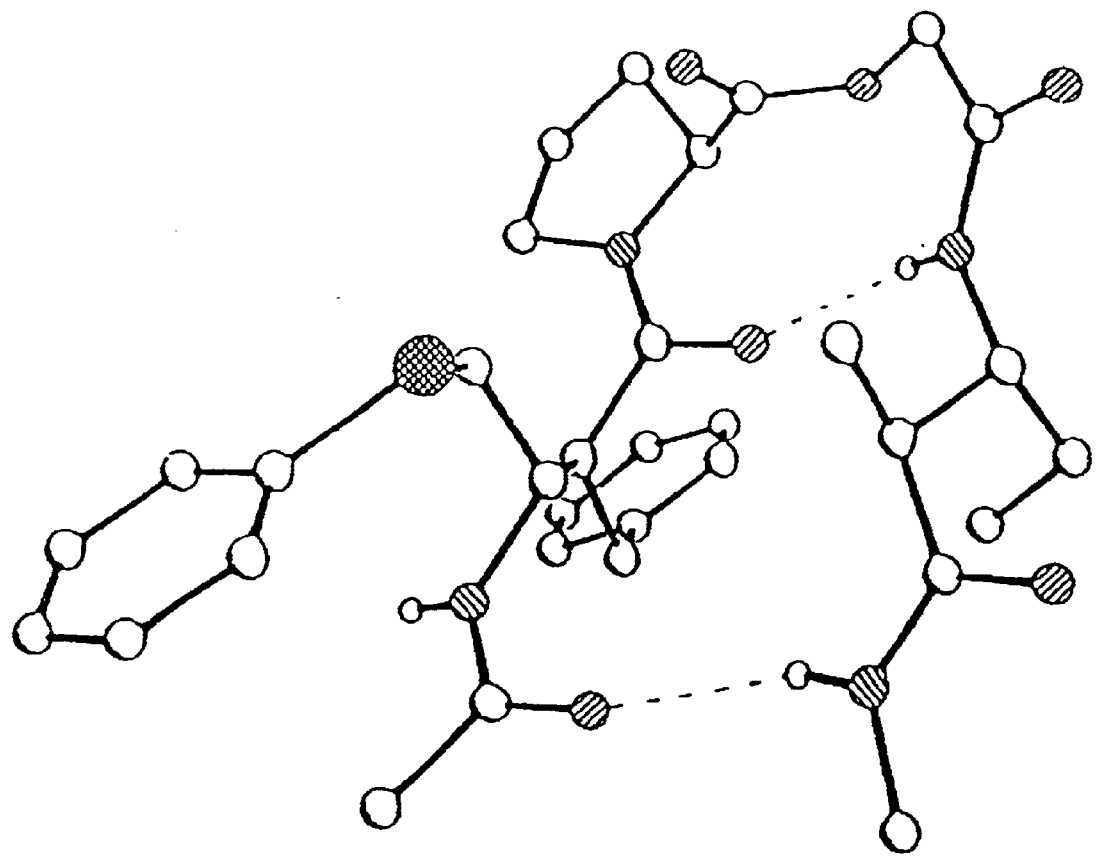
FIG. 16 is a ball and stick representation of the solid state conformation of compound 1 described below. For clarity, all hydrogen atoms, except for those attached to nitogen, have been omitted. Hydrogen bonds are indicated with dotted lines.

Compound 1 was synthesized as described above. Crystals of compound 1 suitable for X-ray analysis were obtained by vapor diffusion (over 2 weeks) of n-heptane into a solution of the sample in ethyl acetate. The data were collected on a Siemens P4/CCD diffractometer running software provided by the manufacturer. The ball and stick schematic of the crystal structure in the solid state is presented in FIG. 16. All hydrogens except those bonded to nitrogen have been removed for clarity. Hydrogen bonds are shown in dotted lines.

Combinatorial Chemistry:

The defined conformation conferred by the β-polypeptides described herein makes these polyamide compounds highly useful for constructing large libraries of potentially useful compounds via combinatorial chemistry. Combinatorial exploration of functionalized oligomers of, for instance, trans-ACHC, trans-ACPC, or β-peptides wherein the α and β carbons are part of a cycloalkenyl ring or a heterocyclic ring such a pyrrolidinyl or piperidinyl moiety, or "mixed" β-peptides containing acyclic residues in addition to cyclic residues, has a potential yield of literally millions of novel polypeptide molecules, all of which display a well-defined helical or sheet secondary structure.

Of particular note here is that the equatorial positions of the cyclohexyl β-peptides can be substituted with virtually any substituent, including very large substituents, without disrupting the helical secondary structure. At least in helical structures, this is because any equatorial substituent extends essentially perpendicular from the axis of rotation of the helix, thereby leaving the hydrogen bonds of the helix undisturbed.

The amino acids which comprise the finished peptides can be functionalized prior to being incorporated into a polypeptide, or an unfunctionalized polypeptie can be constructed and then the entire oligomer functionalized. Neither method is preferred over the other as they are complementary depending upon the types of compounds which are desired.

Combinatorial libraries utilizing the present compounds may be constructed using any means now known to the art or developed in the future. The preferred methods, however, are the "split and pool" method using solid-phase polypeptide synthesis on inert solid substrates and parallel synthesis, also referred to as multipin synthesis.

The "split and pool" concept is based on the fact that combinatorial bead libraries contain single beads which display only one type of compound, although there may be up to 10$^{13}$ copies of the same compound on a single 100 μm diameter bead. The process proceeds as follows, utilizing standard solid-phase peptide synthesis as described above:

Several suitable solid substrates are available commercially. The substrates are generally small diameter beads, e.g. about 100 μm, formed from inert polymeric materials such as polyoxyethylene-grafted polystyrene or polydimethylacrylamide. An illustrative substrate, marketed under the trademark "ARGOGEL" is available from Argonaut Technologies, Washington, D.C.

Figure 15:
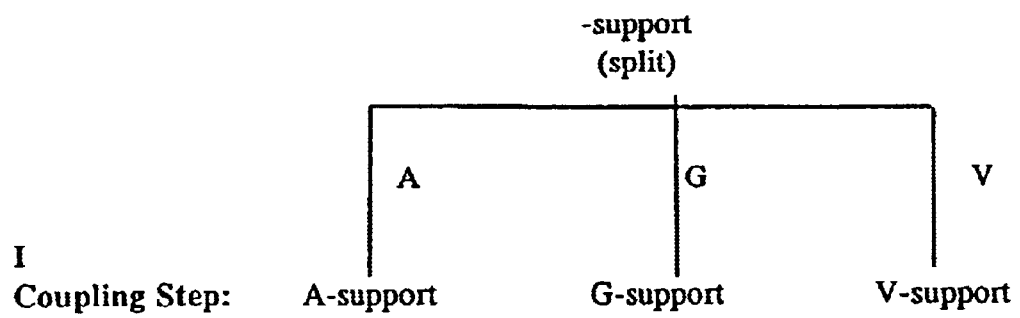
FIG. 15 is a schematic representation of the "split and pool" method of generating combinatorial libraries.
Figure 15:
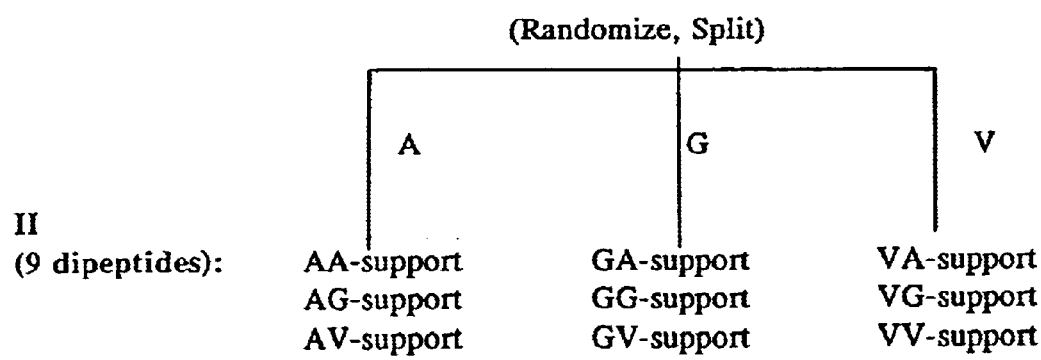
Figure 15:
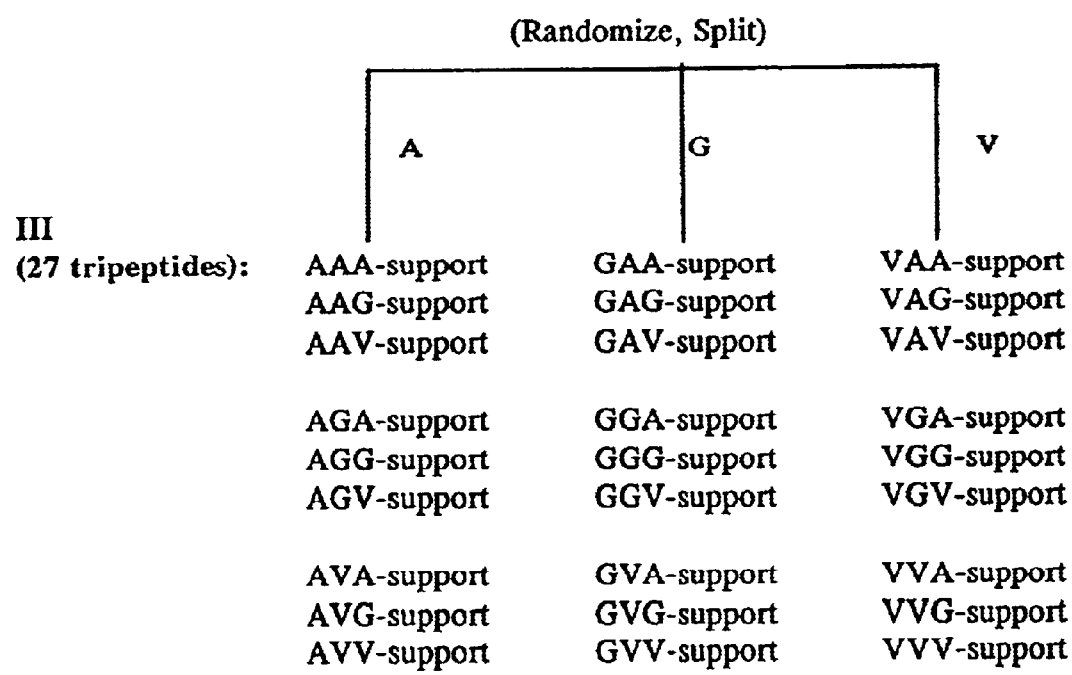

Referring now to FIG. 15, which is a schematic depicting the split and pool method, a plurality of inert substrates are divided into two or more groups and then a first set of subunits is covalently linked to the inert support. As depicted in FIG. 15, the initial plurality of substrates is divided into three subgroups. The appearance of the three groups of beads after the first round of coupling is shown at I of FIG. 15. The three groups of beads are then pooled together to randomize the beads. The beads are then again split into a number of subgroups. Another round of coupling then takes place wherein a second subunit is bonded to the first subunit already present on each bead. The process is then repeated (theoretically ad infinitum) until the desired chain length is attained.

The split and pool process is highly flexible and has the capability of generating literally millions of different compounds which, in certain applications, can be assayed for activity while still attached to the inert substrate.

A critical aspect of the split and pool methodology is that each reaction be driven to completion to prior to initiating a subsequent round of coupling. So long as each coupling reaction is driven to completion, each substrate bead will only display a single compound. Because the rate of reaction will differ from bead to bead as the library construction progresses, the beads can be monitored using conventional dyes to ensure that coupling is completed prior to initiating another round of synthesis. The presence of only a single compound per bead comes about because each individual bead encounters only one amino acid at each coupling cycle. So long as the coupling cycle is driven to completion, all available coupling sites on each bead will be reacted during each cycle and therefore only one type of peptide will be displayed on each bead.

The resulting combinatorial library is comprised of a plurality of inert substrates, each having covalently linked thereto a different β-polypeptide. The polypeptides can be screened for activity while still attached to the inert support, if so desired and feasible for the activity being investigated. Beads which display the desired activity are then isolated and the polypeptide contained thereon characterized via conventional peptide chemistry, such as the Edman degradation. Where a solution-phase assay is to be used to screen the library, the polypeptides are cleaved from the solid substrate and tested in solution.

As applied in the present invention, one or more of the subunits coupled to the inert substrate are selected from the β-amino acids described herein. In this fashion, large libraries of β-polypeptides can be assembled, all of compounds contained therein which display predictable secondary structure.

An alternative approach to generating combinatorial libraries uses parallel synthesis. In this approach, a known set of first subunits is covalently linked to a known location on a inert substrate, one subunit type to each location. The substrate may be a series of spots on a suitable divisible substrate such as filter paper or cotton. A substrate commonly used is an array of pins, each pin being manufactured from a suitable resin, described above.

After the initial round of coupling, each pin of the array bears a first subunit covalently linked thereto. The array is then reacted with a known set of second subunits, generally different from the first, followed by reactions with a third set of subunits, and so on. During each reiteration, each individual pin (or location) is coupled with a incoming subunit selected from a distinct set of subunits, with the order of the subunits being recorded at each step. The final result is an array of polypeptides, with a different polypeptide bonded to each solid substrate. Because the ordering of the subunits is recorded, the identity of the primary sequence of the polypeptide at any given location on the substrate (i.e., any given pin) is known. As in the split and pool method, each coupling reaction must be driven to completion in order to ensure that each location on the substrate contains only a single type of polypeptide.

Large Molecule Interactions:

Another use for the present compounds is as molecular probes to investigate the interactions between biological macromolecules to identify antagonists, agonists, and inhibitors of selected biological reactions. As noted above, many biological reactions take place between very large macromolecules. The surface areas in which these reactions take place are thought by many to be far too large to be disrupted, altered, or mimicked by a small molecule. Until the present invention, it has been difficult, if not impossible, to manufacture molecular probes of modest size that display a well-defined conformation. Because the compounds described herein assume a highly predictable helical or sheet conformation, even when functionalized, they find use as reagents to probe the interaction between large biomolecules.

Employing the combinatorial methods described herein greatly expands the medicinal application of the compounds as vast libraries of compounds can be screened for specific activities, such as inhibitory and antagonist activity in a selected biological reaction.

Antimicrobial Activity/Non-hemolytic Activity

Examples 10 and 11

Example 10: Oligomers of (R,R)-trans-2-aminocyclopentanecarboxylic acid (ACPC) adopt a helix defined by 12-membered ring having "C=O—H—N" hydrogen bonds between each backbone carbonyl and the amide proton of the third residue in the C-terminal direction. This secondary structure is referred to herein as the "12-helix." (For comparison, the familiar α-helix in conventional peptides is defined by 13-membered ring with C=O—H—N hydrogen bonds between each backbone carbonyl and the amide proton of the fourth residue in the C-terminal direction.) The β-peptide 12-helix has approximately 2.5 residues per turn.

A protected version of (R,R)-trans-4-aminopyrrolidine-3-carboxylic acid (APC) was prepared from the known β-ketoester as shown in Reaction 5 (compound 58). After incorporation into a β-peptide and removal of the Boc protecting group from the ring nitrogen atom, the APC residue should be cationic at pH≦8. The APC derivative shown in Reaction 5 and Fmoc-protected ACPC were used for solid-phase synthesis of oligomers β-7, β-12 and β-17:

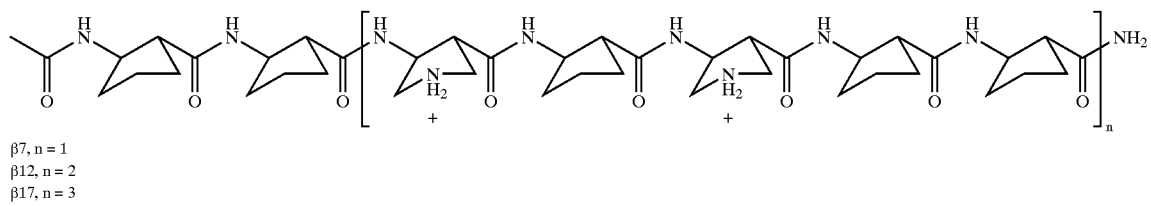

β7, n = 1
β12, n = 2
β17, n = 3

Each β-peptide bears an acetyl capping group at the N-terminus and a primary amide at the C-terminus. These β-peptides were designed with the intent that they would form amphiphilic 12-helices in aqueous solution, with all cationic APC residues on one side of the helix and all hydrophobic ACPC residues on the other side.

The activities of β-7, β-12 and β-17 against four bacteria were assessed in liquid medium. Also examined, as a positive control, was a synthetic magainin derivative (GIGKFLHAAKKFAKAFVAEIMNS-NH$_2$) (SEQ. ID. NO. 1) that displays enhanced antimicrobial activity relative to the natural magainins. *Enterococcus faecium* A436 (Nicus et al., Characterization of vancomucin resistance *Enterococcus faecium* and *Enterococcus faecalis*, Antimicrob. Agents Chemother. 33:11121–24 (1989)) and *Staphylococcus aureus* 1206 (Weisblum et al., Erythromycin-inducible resistance in *Staphylococcus aurens*: survey of antibiotic cases involved, J. Bacteriol., 98:447–52 (1969)) are clinical isolates, while *Bacillus subtilis* BR151 (Young et al., Chromosomal location of genes regulating resistance to bacteriophage in *Bacillus subtilis*, J. Bacteriol., 98:2087–97 (1969)) and *Escherichia coli* JM109 (Yanisch-Perron et al., Improved M13 phage cloning vectors and host strains: nucleotide sequences of the M13mp18 and pUC19 vectors, Gene 33:103–19 (1985)) are non-pathogenic strains commonly used in the laboratory for genetic constructions. (Pathogenic strains of *E. coli* are well known; while *B. subtilis* itself shows little tendency to colonize humans, a related species, *B. anthracis*, causes anthrax.)

Preliminary studies showed that the antibacterial activity of the β-peptides against all four bacteria improves steadily as the length increases, with β-17 comparable to the magainin. β-7 showed some, albeit very small, activity against all of the four bacteria, but β-12 was moderately active against *B. subtilis* and *E. faecium*, and showed detectable activity against *E. coli* and *S. aureus*. Table 2 provides minimum inhibitory concentration (MIC) and minimum bactericidal concentration (MBC) data for β-17 and the magainin.

As shown in Table 2, β-17 is potent against all four bacteria, and this β-peptide matches or exceeds the magainin in all four cases. The sizes of β-17 and the magainin are similar: there are 64 carbon and nitrogen atoms in the backbone of β-17 and 72 carbon and nitrogen atoms in the backbone of the magainin. If the 23-residue magainin were fully folded into an α-helix (3.6 residues per turn), this molecule would form roughly 6.4 helical turns and have a length of roughly 34 Å. If the 17-residue β-peptide were fully folded into a 12-helix, the molecule would form roughly 6.8 helical turns and have a length of roughly 37 Å.

In this example, the β-7, β-12 and β-17 were used in the trifluoroacetate salt forms (trifluoroacetic acid was a component of the eluent used for HPLC purification). Therefore, control experiments were run to determine whether trifluoroacetate exerts any antibacterial effect. Addition of up to 50 mM sodium trifluoroacetate to the growth media had no effect on the growth of any of the four bacteria used in this Example. The conclusion, therefore, is that the activities summarized in Table 2 result from the β-peptides themselves rather than their counterions.

Figure 17:
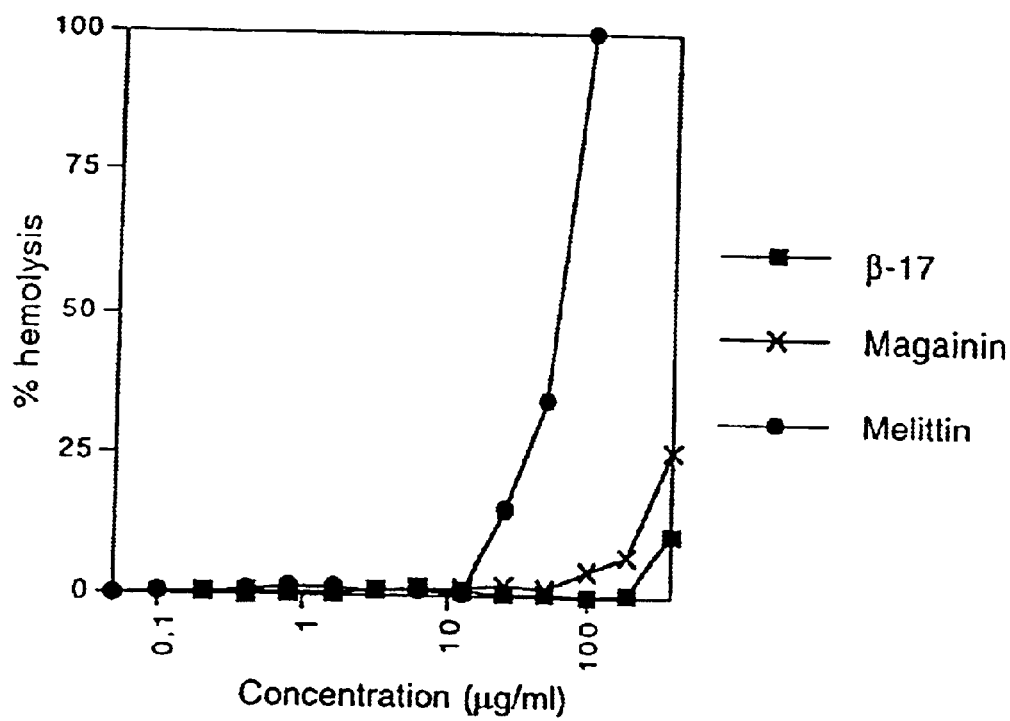
FIG. 17 is a graph depicting the results of a direct hemolysis comparison between melittin (a positive control), a magainin derivative, and β-17 (see Example 11).

Example 11: Therapeutic utility requires that a cationic peptide act selectively against bacterial cells in the presence of human cells. This issue is typically probed by comparing red blood cell lytic activity ("hemolysis") with antimicrobial activity. Magainins display low hemolytic activity, but other natural cationic helix-forming peptides are highly hemolytic. For example, the 26-residue peptide melittin, isolated from honey bee venom, readily lyses both bacterial and human red blood cells. FIG. 17 shows the results of a direct hemolysis comparison between melittin (a positive control), the magainin derivative, and β-17. Significant hemolysis occurs at 50 μg/ml melittin, and hemolysis is complete by 100 μg/ml. In contrast, the magainin derivative displays hemolytic activity only above 100 μg/ml, and β-17 is even less hemolytic than the magainin.

To generate the data shown in FIG. 17, human red blood cells (1% suspension in PBS) were incubated at room temperature for 1 h with a two-fold serial dilution of peptide in PBS. Release of hemoglobin was measured by determining the $OD_{415}$ of the supernatant after centrifugation. Controls consisted of human red blood cells suspended in PBS (zero hemolysis) and suspended in 1% SDS (100% hemolysis).

These results clearly show that the subject compounds with a completely unnatural backbone have a specific and very useful antimicrobial activity.

TABLE 2

Bacteriostatic[a] and Bactericidal[b] Activities of β-17 and (Ala[8,13,18])-Magainin II amide (μg/ml)

| | | E. coli | B. subtilis | E. faecium | S. aureus |
|---|---|---|---|---|---|
| β-17 | MIC | 12.5 | 6.3 | 50 | 25 |
| | MBC | 12.5 | 12.5 | 200 | ~100[c] |
| Magainin | MIC | 25 | 25 | >200 | >100 |
| | MBC | 50 | 50 | >200 | >100 |

[a]Minimal inhibitory concentration (MIC) is defined here as the lowest concentration of peptide required for complete inhibition of growth as determined by optical density at 590 nm. Bacterium in BHI medium (~10$^6$ CFU/ml) were incubated for 6 h at 37° C. with a two-fold dilution series of peptide in medium in a sterile 96-well plate. Microbial growth was determined by the increase in $OD_{590}$ over the 6 h period.
[b]Minimal bactericidal concentration (MBC) refers to the lowest concentration of peptide required for the absence of viable colonies. The bactericidal activities of the MIC, MIC × 2, and MIC × 4 were examined. The well solution was diluted and plated in order to allow a maximum of ~10$^3$ colony-forming units to grow on the agar plate. Plates for $t_0$ contained approximately 1000 colonies. The plates were incubated overnight at 37° C., and colonies were counted for determination of bactericidal activity.
[c]Peptide concentration of 100 μg/ml revealed 10 colonies (~99% killing).

It is understood that the invention is not confined to the particular reagents, reactions, and methodologies described above, but embraces all modified and equivalent forms thereof as come within the scope of the following claims.

What is claimed is:

1. A pharmaceutical composition comprising an antimicrobial-effective amount of a β-amino acid oligomer or polymer wherein each residue of the oligomer or polymer is a β-amino acid residue comprising formula:

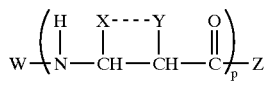

wherein p is an integer greater than 6;

wherein X is independently selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{n+1}$—OR, —$(CH)_{n+1}$—SR, —$(CH_2)_{n+1}$—S(=O)—$CH_2$—R, —$(CH_2)_{n+1}$—S(=O)$_2$—$CH_2$—R, —$(CH_2)_{n+1}$—NRR, —$(CH_2)_{n+1}$—NHC(=O)R, —$(CH_2)_{n+1}$—NHS(=O)$_2$—$CH_2$—R, —$(CH_2)_{n+1}$—O—$(CH_2)_m$—$R^1$, —$(CH_2)_{n+1}$—S—$(CH_2)_m$—$R^1$, —$(CH_2)_{n+1}$—S(=O)—$(CH_2)_m$—$R^1$, —$(CH_2)_{n+1}$—S(=O)$_2$—$(CH_2)_m$—$R^1$, —$(CH_2)_{n+1}$—NH—$(CH_2)_m$—$R^1$, —$(CH_2)_{n+1}$—N—{$(CH_2)_m$—$R^1$}$_2$, —$(CH_2)_{n+1}$—NHC(=O)—$(CH_2)_{n+1}$—$R^1$, and —$(CH_2)_{n+1}$—NHS(=O)$_2$—$(CH_2)_m$—$R^1$;

wherein R is independently selected from the group consisting of hydrogen, $C_1$–$C_6$-alkyl, alkenyl, or alkynyl; mono- or bicyclic aryl, mono- or bicyclic heteraryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^1$ is independently selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane;

wherein Y is independently selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_n$—OR, —$(CH_2)_n$—SR, —$(CH_2)_n$—S(=O)—$CH_2$—R, —$(CH_2)_n$—S(=O)$_2$—$CH_2$—R, —$(CH_2)_n$—NRR, —$(CH_2)_n$—NHC(=O)R, —$(CH_2)_n$—NHS(=O)$_2$—$CH_2$—R, —$(CH_2)_n$—O—$(CH_2)_m$—$R^1$, —$(CH_2)_n$—S—$(CH_2)_m$—$R^1$, —$(CH_2)_n$—S(=O)—$(CH_2)_m$—$R^1$, —$(CH_2)_n$—S(=O)$_2$—$(CH_2)_m$—$R^1$, —$(CH_2)_n$—NH—$(CH_2)_m$—$R^1$, —$(CH_2)_n$—N—{$(CH_2)_m$—$R^1$}$_2$, —$(CH_2)_n$—NHC(=O)—$(CH_2)_m$—$R^1$, and —$(CH_2)_n$—NHS(=O)$_2$—$(CH_2)_m$—$R^1$;

wherein R and $R^1$ are as defined hereinabove; or

X and Y combined, together with the carbon atoms to which they are bonded, independently define a substituted or unsubstituted $C_3$–$C_8$ cycloalkyl, cycloalkenyl or heterocyclic ring having one or more N, O or S atom(s) as the heteroatom(s);

the substituents on carbon atoms of the rings being independently selected from the group consisting of linear or branched $C_1$–$C_6$-alkyl, alkenyl, alkynyl; mono- or bicyclic aryl, mono- or bicyclic heteraryl having up to 5 heteroatoms selected from N, O, and S; mono- or bicyclic aryl-$C_1$–$C_6$-alkyl, mono- or bicyclic heteroaryl-$C_1$–$C_6$-alkyl, and the substituents listed above for X and Y when X and Y are not combined;

the substituents on nitrogen heteroatoms of the rings being independently selected from the group consisting of —S(=O)$_2$—CH$_2$—R, —C(=O)—R, —S(=O)$_2$—(CH$_2$)$_m$—R$^1$, —C(=O)—(CH$_2$)$_{n+1}$—R$^1$; wherein R and R$^1$ are as defined hereinabove;

m is an integer of from 2–6 and n is an integer of from 0–6;

W is hydrogen or an amino-terminal capping group;

Z is hydroxy or a carboxy-terminal capping group;

and further wherein in at least one residue, X and Y are combined in a cyclic moiety; and pharmaceutically-suitable salts thereof; in combination with a pharmaceutically-suitable carrier.

2. The composition according to claim 1, wherein in each residue:

X is selected from the group consisting of hydrogen, linear or branched C$_1$–C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$–C$_6$-alkyl, mono- or bicyclic heteroaryl-C$_1$–C$_6$-alkyl, —(CH$_2$)$_{n+1}$—OR, —(CH$_2$)$_{n+1}$—SR, —(CH$_2$)$_{n+1}$—S(=O)—CH$_2$—R, —(CH$_2$)$_{n+1}$—S(=O)$_2$—CH$_2$—R, —(CH$_2$)$_{n+1}$—NRR, —(CH$_2$)$_{n+1}$—NHC(=O)R, —(CH$_2$)$_{n+1}$—NHS(=O)$_2$—CH$_2$—R, —(CH$_2$)$_{n+1}$—O—(CH$_2$)$_m$—R$^1$, —(CH$_2$)$_{n+1}$—S—(CH$_2$)$_m$—R$^1$, —(CH$_2$)$_{n+1}$—S(=O)—(CH$_2$)$_m$—R$^1$, —(CH$_2$)$_{n+1}$—S(=O)$_2$—(CH$_2$)$_m$—R$^1$, —(CH$_2$)$_{n+1}$—NH—(CH$_2$)$_m$—R$^1$, —(CH$_2$)$_{n+1}$—N—{(CH$_2$)$_m$—R$^1$}$_2$, —(CH$_2$)$_{n+1}$—NHC(=O)—(CH$_2$)$_{n+1}$—R$^1$, and —(CH$_2$)$_{n+1}$—NHS(=O)$_2$—(CH$_2$)$_m$—R$^1$;

Y is selected from the group consisting of hydrogen, linear or branched C$_1$–C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$–C$_6$-alkyl, mono- or bicyclic heteroaryl-C$_1$–C$_6$-alkyl, —(CH$_2$)$_n$—OR, —(CH$_2$)$_n$—SR, —(CH$_2$)$_n$—S(=O)—CH$_2$—R, —(CH$_2$)$_n$—S(=O)$_2$—CH$_2$—R, —(CH$_2$)$_n$—NRR, —(CH$_2$)$_n$—NHC(=O)R, —(CH$_2$)$_n$—NHS(=O)$_2$—CH$_2$—R, —(CH$_2$)$_n$—O—(CH$_2$)$_m$—R$^1$, —(CH$_2$)$_n$—S—(CH$_2$)$_m$—R$^1$, —(CH$_2$)$_n$—S(=O)—(CH$_2$)$_m$—R$^1$, —(CH$_2$)$_n$—S(=O)$_2$—(CH$_2$)$_m$—R$^1$, —(CH$_2$)$_n$—NH—(CH$_2$)$_m$—R$^1$, —(CH$_2$)$_n$—N—{(CH$_2$)$_m$—R$^1$}$_2$—(CH$_2$)$_n$—NHC(=O)—(CH$_2$)$_m$—R$^1$, and —(CH$_2$)$_n$—NHS(=O)$_2$—(CH$_2$)$_m$—R$^1$; and when X and Y are combined to define a cyclic moiety, X and Y combined, together with the carbon atoms to which they are bonded, independently define a substituted or unsubsituted C$_3$–C$_8$ cycloalkyl, cycloalkenyl or heterocyclic ring having one or more N, O or S atom(s) as the heteroatom(s).

3. The composition according to claim 1, wherein in each residue:

X and Y are independently selected from the group consisting of linear or branched C$_1$–C$_6$-alkyl, hydroxy-C$_1$–C$_6$-alkyl, amino-C$_1$–C$_6$-alkyl, aryl-C$_1$–C$_6$-alkyl, heteroaryl-C$_1$–C$_6$-alkyl, and carboxyl-C$_1$–C$_6$-alkyl; and when X and Y are combined to define a cyclic moiety, X and Y combined, together with the carbon atoms to which they are bonded, independently define a substituted or unsubstituted C$_3$–C$_8$ cycloalkyl, cycloalkenyl or heterocyclic ring having one or more N, O or S atom(s) as the heteroatom(s).

4. The composition according to claim 1, wherein in each residue X and Y are combined and X and Y combined, together with the carbon atoms to which they are bonded, independently define a substituted or unsubsituted C$_3$–C$_8$ cycloalkyl, cycloalkenyl or heterocyclic ring having one or more N, O or S atom(s) as the heteroatom(s).

5. The composition according to claim 1, wherein in each residue X and Y are combined and X and Y combined, together with the carbon atoms to which they are bonded, independently define a substituted or unsubsituted C$_5$–C$_6$ cycloalkyl, cycloalkenyl, or heterocyclic ring having one nitrogen atom as the sole heteroatom.

6. The composition according to claim 1, wherein in each residue X and Y are combined and X and Y, together with the carbons to which they are bonded, independently define a substituted or unsubstituted cyclopentyl, substituted or unsubstituted cyclohexyl, unsubstituted or N-substituted piperidinyl, or unsubstituted or N-substituted pyrrolidinyl.

7. The composition according to claim 1, wherein in each residue X and Y are combined and X and Y combined, together with the carbon atoms to which they are bonded, independently define a substituted cyclopentyl, cyclohexyl, pyrrolidinyl, or piperidinyl ring, wherein the substituent is selected from the group consisting of amino, mono- or di-C$_1$–C$_6$-alkylamino, carboxamido, sulfonamido, urea, thio, and C$_1$–C$_6$-alkylthio.

8. The composition according to claim 1, wherein in each residue X and Y are combined and X and Y combined, together with the carbon atoms to which they are bonded, independently define an amino-substituted cyclopentyl, amino-substituted cyclohexyl, N-substituted pyrrolidinyl, or N-substituted piperidinyl ring.

9. The composition according to claim 1, wherein W is selected from the group consisting of hydrogen, formyl, acetyl, tBoc, and Fmoc; and Z is selected from the group consisting of hydroxy, NH$_2$, NH(alkyl), and N(alkyl)$_2$.

10. A method of inhibiting microbial growth in mammals, including humans, the method comprising administering an antimicrobial amount of a composition as recited in claim 1 to a patient in need thereof.

11. The method of claim 10, wherein an amount of composition sufficient to provide a concentration of β-amino acid oligomer or polymer at point of contact with a microbial cell of from 1 μM to 10 mM is administered.

12. The method of claim 10, wherein an amount of composition sufficient to provide a concentration of β-amino acid oligomer or polymer at point of contact with a microbial cell of from 1 μM to 100 μM is administered.

13. A method of inhibiting microbial growth in mammals, including humans, the method comprising administering an antimicrobial amount of a composition as recited in claim 2 to a patient in need thereof.

14. The method of claim 13, wherein an amount of composition sufficient to provide a concentration of β-amino acid oligomer or polymer at point of contact with a microbial cell of from 1 μM to 10 mM is administered.

15. The method of claim 13, wherein an amount of composition sufficient to provide a concentration of β-amino acid oligomer or polymer at point of contact with a microbial cell of from 1 μM to 100 μM is administered.

16. A method of inhibiting microbial growth in mammals, including humans, the method comprising administering an antimicrobial amount of a composition as recited in claim 4 to a patient in need thereof.

17. The method of claim 16, wherein an amount of composition sufficient to provide a concentration of β-amino acid oligomer or polymer at point of contact with a microbial cell of from 1 nM to 10 mM is administered.

18. The method of claim 16, wherein an amount of composition sufficient to provide a concentration of β-amino acid oligomer or polymer at point of contact with a microbial cell of from 1 nM to 1 mM is administered.

19. A β-amino acid oligomer or polymer comprising residues of formula I:

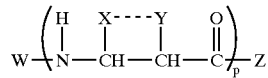

wherein p is an integer greater than 6, and wherein at least two of the residues of formula I are different;

wherein X is independently selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{n+1}$—OR, —$(CH)_{n+1}$—SR, —$(CH_2)_{n+1}$—S(=O)—$CH_2$—R, —$(CH_2)_{n+1}$—S(=O)$_2$—$CH_2$—R, —$(CH_2)_{n+1}$—NRR, —$(CH_2)_{n+1}$—NHC(=O)R, —$(CH_2)_{n+1}$—NHS(=O)$_2$—$CH_2$—R, —$(CH_2)_{n+1}$—O—$(CH_2)_m$—$R^1$, —$(CH_2)_{n+1}$—S—$(CH_2)_m$—$R^1$, —$(CH_2)_{n+1}$—S(=O)—$(CH_2)_m$—$R^1$, —$(CH_2)_{n+1}$—S(=O)$_2$—$(CH_2)_m$—$R^1$, —$(CH_2)_{n+1}$—NH—$(CH_2)_m$—$R^1$, —$(CH_2)_{n+1}$—N—{$(CH_2)_m$—$R^1$}$_2$, —$(CH_2)_{n+1}$—NHC(=O)—$(CH_2)_{n+1}$—$R^1$, and —$(CH_2)_{n+1}$—NHS(=O)$_2$—$(CH_2)_m$—$R^1$;

wherein R is independently selected from the group consisting of hydrogen, $C_1$–$C_6$-alkyl, alkenyl, or alkynyl; mono- or bicyclic aryl, mono- or bicyclic heteraryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^1$ is independently selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane;

wherein Y is independently selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_n$—OR, —$(CH_2)_n$—SR, —$(CH_2)_n$—S(=O)—$CH_2$—R, —$(CH_2)_n$—S(=O)$_2$—$CH_2$—R, —$(CH_2)_n$—NRR, —$(CH_2)_n$—NHC(=O)R, —$(CH_2)_n$—NHS(=O)$_2$—$CH_2$—R, —$(CH_2)_n$—O—$(CH_2)_m$—$R^1$, —$(CH_2)_n$—S—$(CH_2)_m$—$R^1$, —$(CH_2)_n$—S(=O)—$(CH_2)_m$—$R^1$, —$(CH_2)_n$—S(=O)$_2$—$(CH_2)_m$—$R^1$, —$(CH_2)_n$—NH—$(CH_2)_m$—$R^1$, —$(CH_2)_n$—N—{$(CH_2)_m$—$R^1$}$_2$—$(CH_2)_n$—NHC(=O)—$(CH_2)_m$—$R^1$, and —$(CH_2)_n$—NHS(=O)$_2$—$(CH_2)_m$—$R^1$;

wherein R and $R^1$ are as defined hereinabove; or

X and Y combined, together with the carbon atoms to which they are bonded, independently define a substituted or unsubstituted $C_3$–$C_8$ cycloalkyl, cycloalkenyl or heterocyclic ring having one or more N, O or S atom(s) as the heteroatom(s);

the substituents on carbon atoms of the rings being independently selected from the group consisting of linear or branched $C_1$–$C_6$-alkyl, alkenyl, alkynyl; mono- or bicyclic aryl, mono- or bicyclic heteraryl having up to 5 heteroatoms selected from N, O, and S; mono- or bicyclic aryl-$C_1$–$C_6$-alkyl, mono- or bicyclic heteroaryl-$C_1$–$C_6$-alkyl, and the substituents listed above for X and Y when X and Y are not combined;

the substituents on nitrogen heteroatoms of the rings being independently selected from the group consisting of —S(=O)$_2$—$CH_2$—R, —C(=O)—R, —S(=O)$_2$—$(CH_2)_m$—$R^1$, —C(=O)—$(CH_2)_{n+1}$—$R^1$; wherein R and $R^1$ are as defined hereinabove;

m is an integer of from 2–6 and n is an integer of from 0–6;

W is hydrogen or an amino-terminal capping group;

Z is hydroxy or a carboxy-terminal capping group;

and further wherein in at least one residue, X and Y are combined in a cyclic moiety, and salts thereof.

20. The β-amino acid oligomer or polymer according to claim 19, wherein in each residue:

X is selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{n+1}$—OR, —$(CH_2)_{n+1}$—SR, —$(CH_2)_{n+1}$—S(=O)—$CH_2$—R, —$(CH_2)_{n+1}$—S(=O)$_2$—$CH_2$—R, —$(CH_2)_{n+1}$—NRR, —$(CH_2)_{n+1}$—NHC(=O)R, —$(CH_2)_{n+1}$—NHS(=O)$_2$—$CH_2$—R, —$(CH_2)_{n+1}$—O—$(CH_2)_m$—$R^1$, —$(CH_2)_{n+1}$—S—$(CH_2)_m$—$R^1$, —$(CH_2)_{n+1}$—S(=O)—$(CH_2)_m$—$R^1$, —$(CH_2)_{n+1}$—S(=O)$_2$—$(CH_2)_m$—$R^1$, —$(CH_2)_{n+1}$—NH—$(CH_2)_m$—$R^1$, —$(CH_2)_{n+1}$—N—{$(CH_2)_m$—$R^1$}$_2$, —$(CH_2)_{n+1}$—NHC(=O)—$(CH_2)_{n+1}$—$R^1$, and —$(CH_2)_{n+1}$—NHS(=O)$_2$—$(CH_2)_m$—$R^1$; and Y is selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_n$—OR, —$(CH_2)_n$—SR, —$(CH_2)_n$—S(=O)—$CH_2$—R, —$(CH_2)_n$—S(=O)$_2$—$CH_2$—R, —$(CH_2)_n$—NRR, —$(CH_2)_n$—NHC(=O)R, —$(CH_2)_n$—NHS(=O)$_2$—$CH_2$—R, —$(CH_2)_n$—O—$(CH_2)_m$—$R^1$, —$(CH_2)_n$—S—$(CH_2)_m$—$R^1$, —$(CH_2)_n$—S(=O)—$(CH_2)_m$—$R^1$, —$(CH_2)_n$—S(=O)$_2$—$(CH_2)_m$—$R^1$, —$(CH_2)_n$—NH—$(CH_2)_m$—$R^1$, —$(CH_2)_n$—N—{

$(CH_2)_m-R^1\}_2-(CH_2)_n-NHC(=O)-(CH_2)_m-R^1$, and $-(CH_2)_n-NHS(=O)_2-(CH_2)_m-R^1$; and when X and Y are combined to define a cyclic moiety, X and Y combined, together with the carbon atoms to which they are bonded, independently define a substituted or unsubsituted $C_3-C_8$ cycloalkyl, cycloalkenyl or heterocyclic ring having one or more N, O or S atom(s) as the heteroatom(s).

21. The β-amino acid oligomer or polymer according to claim 19, wherein in each residue:

X and Y are independently selected from the group consisting of linear or branched $C_1-C_6$-alkyl, hydroxy-$C_1-C_6$-alkyl, amino-$C_1-C_6$-alkyl, aryl-$C_1-C_6$-alkyl, heteroaryl-$C_1-C_6$-alkyl, and carboxyl-$C_1-C_6$-alkyl; and when X and Y are combined to define a cyclic moiety, X and Y combined, together with the carbon atoms to which they are bonded, independently define a substituted or unsubsituted $C_3-C_8$ cycloalkyl, cycloalkenyl or heterocyclic ring having one or more N, O or S atom(s) as the heteroatom(s).

22. The β-amino acid oligomer or polymer according to claim 19, wherein in each residue X and Y are combined, and wherein X and Y combined, together with the carbon atoms to which they are bonded, independently define a substituted or unsubsituted $C_3-C_8$ cycloalkyl, cycloalkenyl or heterocyclic ring having one or more N, O or S atom(s) as the heteroatom(s).

* * * * *